(12) United States Patent
Hazlehurst et al.

(10) Patent No.: US 7,632,814 B2
(45) Date of Patent: Dec. 15, 2009

(54) HYD1 PEPTIDES AS ANTI-CANCER AGENTS

(75) Inventors: Lori Anne Hazlehurst, Ruskin, FL (US); William S. Dalton, Temple Terrace, FL (US); Anne E. Cress, Tucson, AZ (US); Kit Lam, Davis, CA (US)

(73) Assignees: University of South Florida, Tampa, FL (US); H. Lee Moffitt Cancer Center & Research Institute, Tampa, FL (US); The Arizona Board of Regents, Tucson, AZ (US); The Regents of the University of California, Oakland, CA (US)

( * ) Notice: Subject to any disclaimer, the term of this patent is extended or adjusted under 35 U.S.C. 154(b) by 143 days.

(21) Appl. No.: 11/852,177

(22) Filed: Sep. 7, 2007

(65) Prior Publication Data
US 2008/0108552 A1 May 8, 2008

Related U.S. Application Data

(60) Provisional application No. 60/824,838, filed on Sep. 7, 2006, provisional application No. 60/944,160, filed on Jun. 15, 2007.

(51) Int. Cl.
*A61K 38/00* (2006.01)
(52) U.S. Cl. .......................................... 514/12; 530/300
(58) Field of Classification Search ........................ None
See application file for complete search history.

(56) References Cited

U.S. PATENT DOCUMENTS

| 6,849,712 B1 | 2/2005 | McCarthy et al. |
| 2004/0096906 A1 | 5/2004 | Lam et al. |
| 2006/0019900 A1 | 1/2006 | Lam et al. |

FOREIGN PATENT DOCUMENTS

| WO | WO0162776 | * | 3/2001 |
| WO | WO 2005/045430 A1 | | 5/2005 |

OTHER PUBLICATIONS

Aoudjit F, Vuori K. Integrin signaling inhibits paclitaxel-induced apoptosis in breast cancer cells. *Oncogene*. 2001;20:4995-5004.
Astier A, Manie SN, Avraham H, et al. The related adhesion focal tyrosine kinase differentially phosphorylates p130Cas and the Cas-like protein, p105HEF1. *J Biol Chem*. 1997;272:19719-19724.
Chen Q, Lin TH, Der CJ, Juliano RL. Integrin-mediated activation of MEK and mitogen-activated protein kinase is independent of Ras [corrected]. *J Biol Chem*. 1996;271:18122-18127.
Damiano JS, Cress AE, Hazlehurst LA, Shtil AA, Dalton WS. Cell adhesion mediated drug resistance (CAM-DR): role of integrins and resistance to apoptosis in human myeloma cell lines. *Blood*. 1999;93:1658-1667.
Damiano JS, Hazlehurst LA, Dalton WS. Cell adhesion-mediated drug resistance (CAM-DR) protects the K562 chronic myelogenous leukemia cell line from apoptosis induced by BCR/ABL inhibition, cytotoxic drugs, and gamma-irradiation. *Leukemia*. 2001;15:1232-1239.
Deroock IB, Pennington ME, Sroka TC, et al. Synthetic peptides inhibit adhesion of human tumor cells to extracellular matrix proteins. *Cancer Res*. 2001;61:3308-3313.
Hannigan GE, Leung-Hagesteijn C, Fitz-Gibbon L, et al. Regulation of cell adhesion and anchorage-dependent growth by a new beta 1-integrin-linked protein kinase. *Nature*. 1996;379:91-96.
Hazlehurst LA, Argilagos RF, Dalton WS. β1 integrin adhesion increases Bim protein degradation and confers drug resistance in leukemia cells *British Journal Haematology*. 2006.
Hazlehurst LA, Argilagos RF, Emmons M, et al. Cell adhesion to fibronectin (CAM-DR) influences acquired mitoxantrone resistance in U937 cells. *Cancer Res*. 2006;66:2338-2345.
Hazlehurst LA, Damiano JS, Buyuksal I, Pledger WJ, Dalton WS. Adhesion to fibronectin via beta1 integrins regulates p27kip1 levels and contributes to cell adhesion mediated drug resistance (CAM-DR). *Oncogene*. 2000;19:4319-4327.
Hazlehurst LA, Enkemann SA, Beam CA, et al. Genotypic and phenotypic comparisons of de novo and acquired melphalan resistance in an isogenic multiple myeloma cell line model. *Cancer Res*. 2003;63:7900-7906.
Hazlehurst LA, Valkov N, Wisner L, et al. Reduction in drug-induced DNA double-strand breaks associated with beta1 integrin-mediated adhesion correlates with drug resistance in U937 cells. *Blood*. 2001;98:1897-1903.
Hazlehurst LA, Targeting beta1 Integrins in Multiple Myeloma. Presentation at *Advancing Myeloma Therapy: Translating Laboratory Concepts Into Clinical Reality Symposium held in conjunction with the XI$^{th}$ International Myeloma Symposium*. Jun. 25, 2007.
King WG, Mattaliano MD, Chan TO, Tsichlis PN, Brugge JS. Phosphatidylinositol 3-kinase is required for integrin-stimulated AKT and Raf-1/mitogen-activated protein kinase pathway activation. *Mol Cell Biol*. 1997;17:4406-4418.

(Continued)

*Primary Examiner*—Larry R. Helms
*Assistant Examiner*—Meera Natarajan
(74) *Attorney, Agent, or Firm*—Saliwanchik, Lloyd & Saliwanchik

(57) ABSTRACT

The present invention concerns fragments and variants of the HYD1 peptide; polynucleotides encoding the peptides; host cells genetically modified with the polynucleotides; vectors comprising the polynucleotides; compositions containing these peptides, polynucleotides, vectors, or host cells; and methods of using the peptides, polynucleotides, vectors, and host cells as inhibitors of aberrant cell growth in vitro or in vivo, e.g., as anti-cancer agents for treatment of cancer, such as myeloma. The present invention further includes a method of increasing the efficacy of chemotherapy and radiation therapy, comprising administering an agent that binds β1 integrin to a patient in need thereof. In one embodiment, the β1 integrin binding agent is the HYD1 peptide, or a functional fragment or variant thereof. In another aspect, the invention pertains to a composition (an adhesion trap) comprising a substrate (also referred to as a surface or support) with a HYD1 peptide, or fragment or variant thereof, immobilized to the substrate, and a method of removing circulating tumor cells (CTC) from blood by contacting a subject's blood with the immobilized peptide. Another aspect of the invention concerns a method of identifying modulators of peptide binding. Another aspect of the invention concerns a method for detecting CTC.

16 Claims, 54 Drawing Sheets

OTHER PUBLICATIONS

Lwin T, Hazlehurst LA, Dessureault S, et al. Cell adhesion induces p27Kip1-associated cell-cycle arrest through down-regulation of the SCFSkp2 ubiquitin ligase pathway in mantle cell and other non-Hodgkin's B-cell lymphomas. *Blood*. 2007.

Nefedova Y, Landowski TH, Dalton WS. Bone marrow stromal-derived soluble factors and direct cell contact contribute to de novo drug resistance of myeloma cells by distinct mechanisms. *Leukemia*. 2003;17:1175-1182.

Pennington ME, Lam KS, Cress AE. The use of a combinatorial library method to isolate human tumor cell adhesion peptides. *Mol Divers*. 1996;2:19-28.

Schaller MD, Parsons JT. pp125FAK-dependent tyrosine phosphorylation of paxillin creates a high-affinity binding site for Crk. *Mol Cell Biol*. 1995;15:2635-2645.

Schlaepfer DD, Hanks SK, Hunter T, Van Der Geer P. Integrin-mediated signal transduction linked to Ras pathway by GRB2 binding to focal adhesion kinase. *Nature*. 1994;372:786-791.

Sethi T, Rintoul RC, Moore SM, et al. Extracellular matrix proteins protect small cell lung cancer cells against apoptosis: a mechanism for small cell lung cancer growth and drug resistance in vivo. *Nat Med*. 1999;5:662-668.

Sroka TC, Marek J., Pennington ME, Lam KS The Minimum Element of a Synthetic Peptide Required to Block Prostate Tumor Cell Migration *Cancer Biology & Therapy* 2006; 5: 11: 1556-1562.

Sroka TC, Pennington ME, Cress AE. Synthetic D-amino acid peptide inhibits tumor cell motility on laminin-5. *Carcinogenesis*. 2006.

Van Riet I, De Waele M, Remels L, Lacor P, Schots R, Van Camp B. Expression of cytoadhesion molecules (CD56, CD54, CD18 and CD29) by myeloma plasma cells. *Br J Haematol*. 1991;79:421-427.

Yaccoby S, Barlogie B, Epstein J. Primary myeloma cells growing in SCID-hu mice: a model for studying the biology and treatment of myeloma and its manifestations. *Blood*. 1998;92:2908-2913.

Zhu K, Gerbino E, et al. Farnesyltransferase inhibitor R115777 (Zarnestra, Tipifarnib) synergizes with paclitaxel to induce apoptosis and mitotic arrest and to inhibit tumor growth of multiple myeloma cells. *Blood*. 2005;105:4759-4766.

\* cited by examiner

FIG. 16A-1
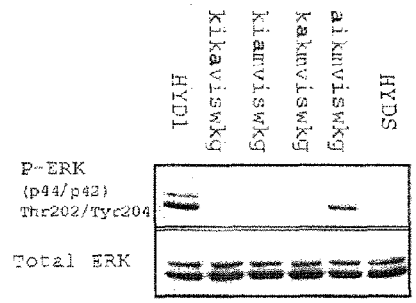
FIG. 16A-2
FIG. 16B
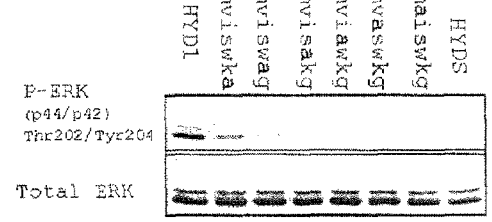
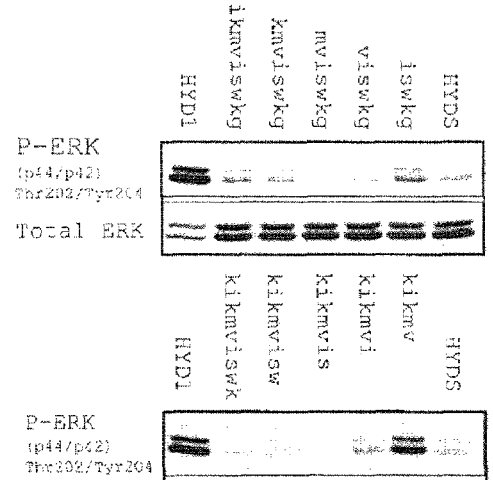
FIG. 16C-1
FIG. 16C-2
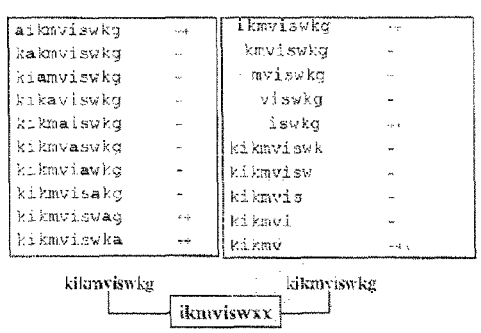

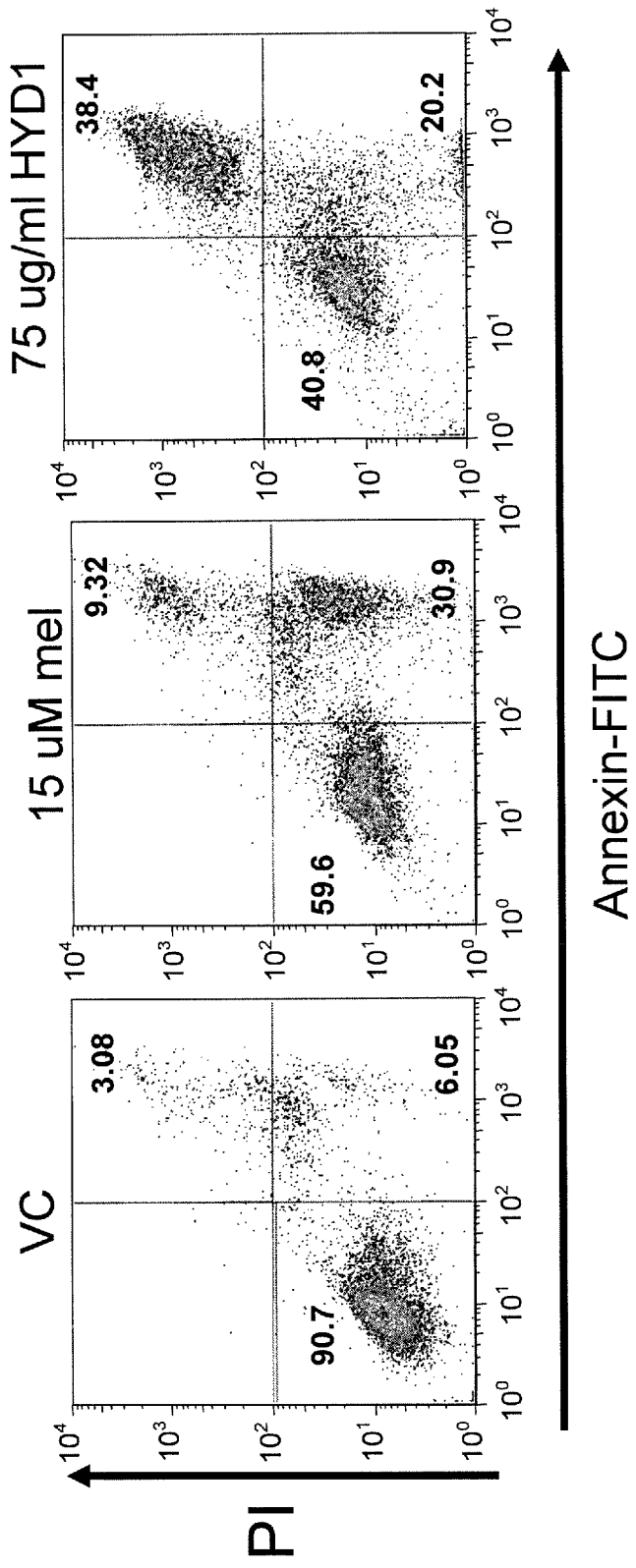

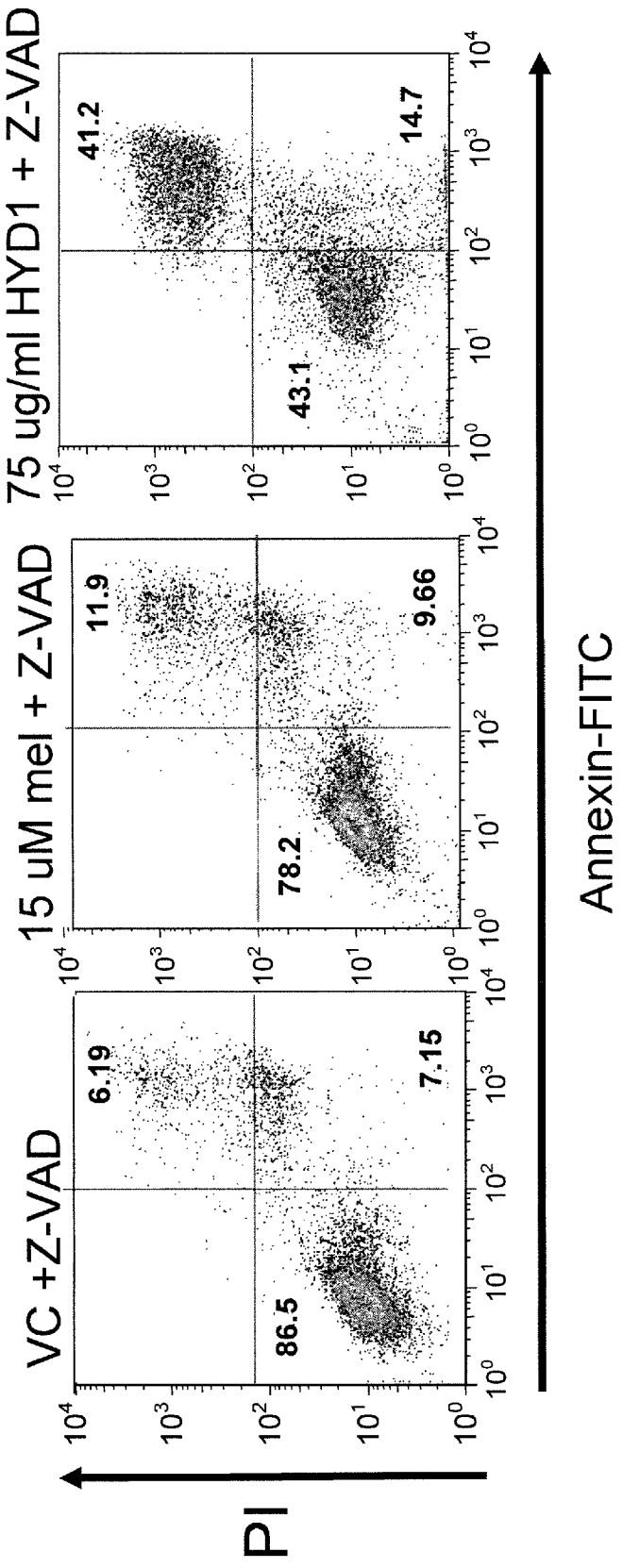

FIG. 23C  15 uM melphalan
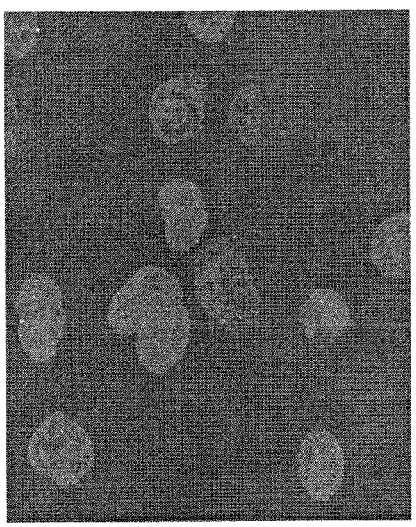
FIG. 23B  100 ug/ml HYD1S
FIG. 23A  VC

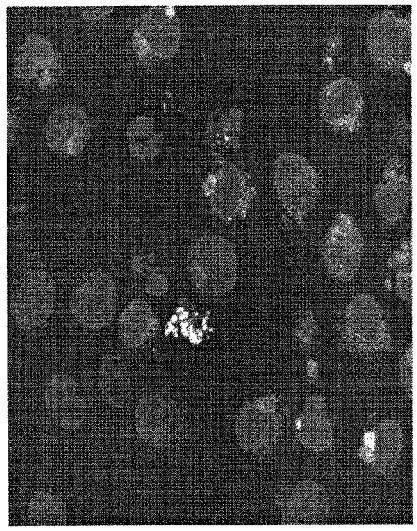
FIG. 23I  20 uM melphalan
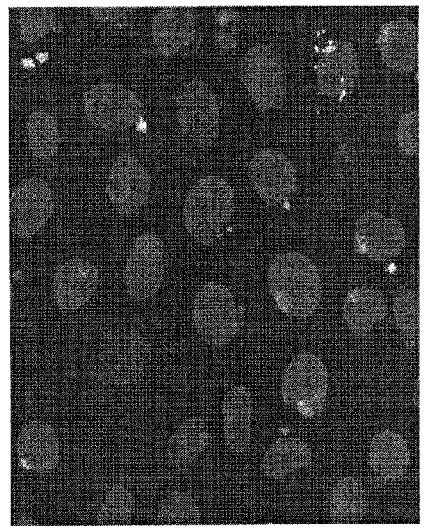
FIG. 23H  100 ug/ml HYD1S
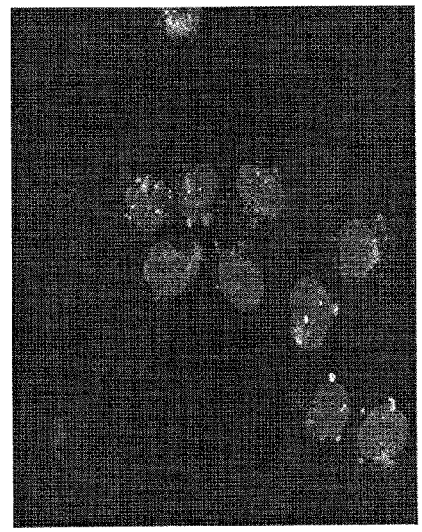
FIG. 23G  VC

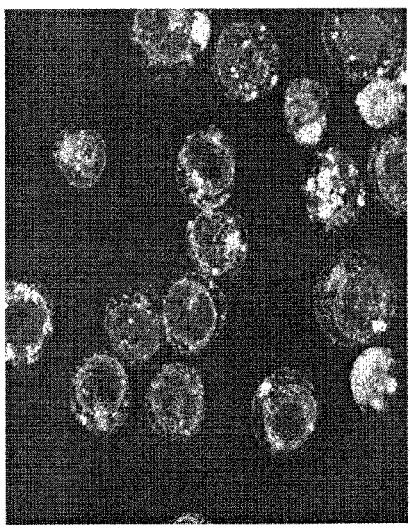
FIG. 23J — 25 ug/ml HYD1
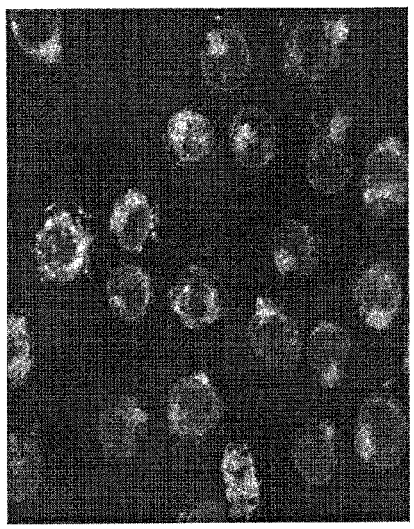
FIG. 23K — 50 ug/ml HYD1
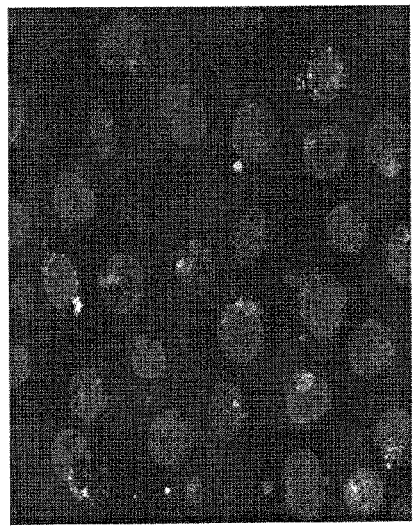
FIG. 23L — 100 ug/ml HYD1

SEQUENCE LISTING

```
<160> NUMBER OF SEQ ID NOS: 50

<210> SEQ ID NO 1
<211> LENGTH: 10
<212> TYPE: PRT
<213> ORGANISM: Artificial Sequence
```

-continued

<220> FEATURE:
<223> OTHER INFORMATION: HYD1 peptide

<400> SEQUENCE: 1

Lys Ile Lys Met Val Ile Ser Trp Lys Gly
1 5 10

<210> SEQ ID NO 2
<211> LENGTH: 10
<212> TYPE: PRT
<213> ORGANISM: Artificial Sequence
<220> FEATURE:
<223> OTHER INFORMATION: HYD1 variant

<400> SEQUENCE: 2

Ala Ile Ala Met Val Ile Ser Trp Ala Gly
1 5 10

<210> SEQ ID NO 3
<211> LENGTH: 10
<212> TYPE: PRT
<213> ORGANISM: Artificial Sequence
<220> FEATURE:
<223> OTHER INFORMATION: HYD1 variant

<400> SEQUENCE: 3

Ala Ile Lys Met Val Ile Ser Trp Ala Gly
1 5 10

<210> SEQ ID NO 4
<211> LENGTH: 10
<212> TYPE: PRT
<213> ORGANISM: Artificial Sequence
<220> FEATURE:
<223> OTHER INFORMATION: HYD1 variant

<400> SEQUENCE: 4

Ala Ile Lys Met Val Ile Ser Trp Lys Gly
1 5 10

<210> SEQ ID NO 5
<211> LENGTH: 7
<212> TYPE: PRT
<213> ORGANISM: Artificial Sequence
<220> FEATURE:
<223> OTHER INFORMATION: HYD1 variant

<400> SEQUENCE: 5

Ala Lys Met Val Ile Ser Trp
1 5

<210> SEQ ID NO 6
<211> LENGTH: 9
<212> TYPE: PRT
<213> ORGANISM: Artificial Sequence
<220> FEATURE:
<223> OTHER INFORMATION: HYD1 variant

<400> SEQUENCE: 6

Ala Lys Met Val Ile Ser Trp Lys Gly
1 5

<210> SEQ ID NO 7
<211> LENGTH: 7
<212> TYPE: PRT
<213> ORGANISM: Artificial Sequence
<220> FEATURE:

```
<223> OTHER INFORMATION: HYD1 variant

<400> SEQUENCE: 7

Ile Ala Met Val Ile Ser Trp
1               5

<210> SEQ ID NO 8
<211> LENGTH: 9
<212> TYPE: PRT
<213> ORGANISM: Artificial Sequence
<220> FEATURE:
<223> OTHER INFORMATION: HYD1 variant

<400> SEQUENCE: 8

Ile Ala Met Val Ile Ser Trp Lys Gly
1               5

<210> SEQ ID NO 9
<211> LENGTH: 7
<212> TYPE: PRT
<213> ORGANISM: Artificial Sequence
<220> FEATURE:
<223> OTHER INFORMATION: HYD1 variant

<400> SEQUENCE: 9

Ile Lys Ala Val Ile Ser Trp
1               5

<210> SEQ ID NO 10
<211> LENGTH: 9
<212> TYPE: PRT
<213> ORGANISM: Artificial Sequence
<220> FEATURE:
<223> OTHER INFORMATION: HYD1 variant

<400> SEQUENCE: 10

Ile Lys Ala Val Ile Ser Trp Lys Gly
1               5

<210> SEQ ID NO 11
<211> LENGTH: 7
<212> TYPE: PRT
<213> ORGANISM: Artificial Sequence
<220> FEATURE:
<223> OTHER INFORMATION: HYD1 variant

<400> SEQUENCE: 11

Ile Lys Met Ala Ile Ser Trp
1               5

<210> SEQ ID NO 12
<211> LENGTH: 9
<212> TYPE: PRT
<213> ORGANISM: Artificial Sequence
<220> FEATURE:
<223> OTHER INFORMATION: HYD1 variant

<400> SEQUENCE: 12

Ile Lys Met Ala Ile Ser Trp Lys Gly
1               5

<210> SEQ ID NO 13
<211> LENGTH: 7
<212> TYPE: PRT
<213> ORGANISM: Artificial Sequence
<220> FEATURE:
<223> OTHER INFORMATION: HYD1 variant
```

```
<400> SEQUENCE: 13

Ile Lys Met Val Ala Ser Trp
1               5

<210> SEQ ID NO 14
<211> LENGTH: 9
<212> TYPE: PRT
<213> ORGANISM: Artificial Sequence
<220> FEATURE:
<223> OTHER INFORMATION: HYD1 variant

<400> SEQUENCE: 14

Ile Lys Met Val Ala Ser Trp Lys Gly
1               5

<210> SEQ ID NO 15
<211> LENGTH: 7
<212> TYPE: PRT
<213> ORGANISM: Artificial Sequence
<220> FEATURE:
<223> OTHER INFORMATION: HYD1 variant

<400> SEQUENCE: 15

Ile Lys Met Val Ile Ala Trp
1               5

<210> SEQ ID NO 16
<211> LENGTH: 9
<212> TYPE: PRT
<213> ORGANISM: Artificial Sequence
<220> FEATURE:
<223> OTHER INFORMATION: HYD1 variant

<400> SEQUENCE: 16

Ile Lys Met Val Ile Ala Trp Lys Gly
1               5

<210> SEQ ID NO 17
<211> LENGTH: 7
<212> TYPE: PRT
<213> ORGANISM: Artificial Sequence
<220> FEATURE:
<223> OTHER INFORMATION: HYD1 variant

<400> SEQUENCE: 17

Ile Lys Met Val Ile Ser Ala
1               5

<210> SEQ ID NO 18
<211> LENGTH: 9
<212> TYPE: PRT
<213> ORGANISM: Artificial Sequence
<220> FEATURE:
<223> OTHER INFORMATION: HYD1 variant

<400> SEQUENCE: 18

Ile Lys Met Val Ile Ser Ala Lys Gly
1               5

<210> SEQ ID NO 19
<211> LENGTH: 7
<212> TYPE: PRT
<213> ORGANISM: Artificial Sequence
<220> FEATURE:
<223> OTHER INFORMATION: HYD1 fragment
```

```
<400> SEQUENCE: 19

Ile Lys Met Val Ile Ser Trp
1               5

<210> SEQ ID NO 20
<211> LENGTH: 9
<212> TYPE: PRT
<213> ORGANISM: Artificial Sequence
<220> FEATURE:
<223> OTHER INFORMATION: HYD1 variant

<400> SEQUENCE: 20

Ile Lys Met Val Ile Ser Trp Ala Gly
1               5

<210> SEQ ID NO 21
<211> LENGTH: 8
<212> TYPE: PRT
<213> ORGANISM: Artificial Sequence
<220> FEATURE:
<223> OTHER INFORMATION: HYD1 variant

<400> SEQUENCE: 21

Lys Met Val Ile Ser Trp Lys Ala
1               5

<210> SEQ ID NO 22
<211> LENGTH: 9
<212> TYPE: PRT
<213> ORGANISM: Artificial Sequence
<220> FEATURE:
<223> OTHER INFORMATION: HYD1 fragment

<400> SEQUENCE: 22

Ile Lys Met Val Ile Ser Trp Lys Gly
1               5

<210> SEQ ID NO 23
<211> LENGTH: 5
<212> TYPE: PRT
<213> ORGANISM: Artificial Sequence
<220> FEATURE:
<223> OTHER INFORMATION: HYD1 fragment

<400> SEQUENCE: 23

Ile Ser Trp Lys Gly
1               5

<210> SEQ ID NO 24
<211> LENGTH: 10
<212> TYPE: PRT
<213> ORGANISM: Artificial Sequence
<220> FEATURE:
<223> OTHER INFORMATION: HYD1 variant

<400> SEQUENCE: 24

Lys Ala Lys Met Val Ile Ser Trp Lys Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: HYD1 variant

<400> SEQUENCE: 25
```

```
Lys Ile Ala Met Val Ile Ser Trp Ala Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: HYD1 variant

<400> SEQUENCE: 26

Lys Ile Ala Met Val Ile Ser Trp Lys Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: HYD1 variant

<400> SEQUENCE: 27

Lys Ile Lys Ala Val Ile Ser Trp Lys Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: HYD1 variant

<400> SEQUENCE: 28

Lys Ile Lys Met Ala Ile Ser Trp Lys Gly
1               5                   10

<210> SEQ ID NO 29
<211> LENGTH: 5
<212> TYPE: PRT
<213> ORGANISM: Artificial Sequence
<220> FEATURE:
<223> OTHER INFORMATION: HYD1 fragment

<400> SEQUENCE: 29

Lys Ile Lys Met Val
1               5

<210> SEQ ID NO 30
<211> LENGTH: 10
<212> TYPE: PRT
<213> ORGANISM: Artificial Sequence
<220> FEATURE:
<223> OTHER INFORMATION: HYD1 variant

<400> SEQUENCE: 30

Lys Ile Lys Met Val Ala Ser Trp Lys Gly
1               5                   10

<210> SEQ ID NO 31
<211> LENGTH: 6
<212> TYPE: PRT
<213> ORGANISM: Artificial Sequence
<220> FEATURE:
<223> OTHER INFORMATION: HYD1 fragment

<400

-continued

```
Lys Ile Lys Met Val Ile
1               5

<210> SEQ ID NO 32
<211> LENGTH: 10
<212> TYPE: PRT
<213> ORGANISM: Artificial Sequence
<220> FEATURE:
<223> OTHER INFORMATION: HYD1 variant

<400> SEQUENCE: 32

Lys Ile Lys Met Val Ile Ala Trp Lys Gly
1               5                   10

<210> SEQ ID NO 33
<211> LENGTH: 7
<212> TYPE: PRT
<213> ORGANISM: Artificial Sequence
<220> FEATURE:
<223> OTHER INFORMATION: HYD1 fragment

<400> SEQUENCE: 33

Lys Ile Lys Met Val Ile Ser
1               5

<210> SEQ ID NO 34
<211> LENGTH: 10
<212> TYPE: PRT
<213> ORGANISM: Artificial Sequence
<220> FEATURE:
<223> OTHER INFORMATION: HYD1 variant

<400> SEQUENCE: 34

Lys Ile Lys Met Val Ile Ser Ala Lys Gly
1               5                   10

<210> SEQ ID NO 35
<211> LENGTH: 8
<212> TYPE: PRT
<213> ORGANISM: Artificial Sequence
<220> FEATURE:
<223> OTHER INFORMATION: HYD1 fragment

<400> SEQUENCE: 35

Lys Ile Lys Met Val Ile Ser Trp
1               5

<210> SEQ ID NO 36
<211> LENGTH: 10
<212> TYPE: PRT
<213> ORGANISM: Artificial Sequence
<220> FEATURE:
<223> OTHER INFORMATION: HYD1 variant

<400> SEQUENCE: 36

Lys Ile Lys Met Val Ile Ser Trp Ala Gly
1               5                   10

<210> SEQ ID NO 37
<211> LENGTH: 9
<212> TYPE: PRT
<213> ORGANISM: Artificial Sequence
<220> FEATURE:
<223> OTHER INFORMATION: HYD1 fragment

<400> SEQUENCE: 37

Lys Ile Lys Met Val Ile Ser Trp Lys
```

<210> SEQ ID NO 38
<211> LENGTH: 10
<212> TYPE: PRT
<213> ORGANISM: Artificial Sequence
<220> FEATURE:
<223> OTHER INFORMATION: HYD1 variant

<400> SEQUENCE: 38

Lys Ile Lys Met Val Ile Ser Trp Lys Ala
1               5                   10

<210> SEQ ID NO 39
<211> LENGTH: 8
<212> TYPE: PRT
<213> ORGANISM: Artificial Sequence
<220> FEATURE:
<223> OTHER INFORMATION: HYD1 fragment

<400> SEQUENCE: 39

Lys Met Val Ile Ser Trp Lys Gly
1               5

<210> SEQ ID NO 40
<211> LENGTH: 5
<212> TYPE: PRT
<213> ORGANISM: Artificial Sequence
<220> FEATURE:
<223> OTHER INFORMATION: HYD1 variant

<400> SEQUENCE: 40

Leu Ser Trp Lys Gly
1               5

<210> SEQ ID NO 41
<211> LENGTH: 7
<212> TYPE: PRT
<213> ORGANISM: Artificial Sequence
<220> FEATURE:
<223> OTHER INFORMATION: HYD1 fragment

<400> SEQUENCE: 41

Met Val Ile Ser Trp Lys Gly
1               5

<210> SEQ ID NO 42
<211> LENGTH: 4
<212> TYPE: PRT
<213> ORGANISM: Artificial Sequence
<220> FEATURE:
<223> OTHER INFORMATION: HYD1 fragment

<400> SEQUENCE: 42

Ser Trp Lys Gly
1

<210> SEQ ID NO 43
<211> LENGTH: 6
<212> TYPE: PRT
<213> ORGANISM: Artificial Sequence
<220> FEATURE:
<223> OTHER INFORMATION: HYD1 fragment

<400> SEQUENCE: 43

Val Ile Ser Trp Lys Gly
1               5

```
<210> SEQ ID NO 44
<211> LENGTH: 10
<212> TYPE: PRT
<213> ORGANISM: Artificial Sequence
<220> FEATURE:
<223> OTHER INFORMATION: HYD1S (scrambled peptide)

<400> SEQUENCE: 44

Trp Ile Lys Ser Met Lys Ile Val Lys Gly
1               5                   10

<210> SEQ ID NO 45
<211> LENGTH: 6
<212> TYPE: PRT
<213> ORGANISM: Artificial Sequence
<220> FEATURE:
<223> OTHER INFORMATION: HYD1 fragment

<400> SEQUENCE: 45

Lys Met Val Ile Ser Trp
1               5

<210> SEQ ID NO 46
<211> LENGTH: 6
<212> TYPE: PRT
<213> ORGANISM: Artificial Sequence
<220> FEATURE:
<223> OTHER INFORMATION: HYD1 variant
<220> FEATURE:
<221> NAME/KEY: misc_feature
<222> LOCATION: (5)..(5)
<223> OTHER INFORMATION: Xaa can be any naturally occurring amino acid

<400> SEQUENCE: 46

Lys Met Val Ile Xaa Trp
1               5

<210> SEQ ID NO 47
<211> LENGTH: 8
<212> TYPE: PRT
<213> ORGANISM: Artificial Sequence
<220> FEATURE:
<223> OTHER INFORMATION: HYD1 fragment

<400> SEQUENCE: 47

Ile Lys Met Val Ile Ser Trp Lys
1               5

<210> SEQ ID NO 48
<211> LENGTH: 9
<212> TYPE: PRT
<213> ORGANISM: Artificial Sequence
<220> FEATURE:
<223> OTHER INFORMATION: HYD1 variant
<220> FEATURE:
<221> NAME/KEY: misc_feature
<222> LOCATION: (8)..(9)
<223> OTHER INFORMATION: Xaa can be any naturally occurring amino acid

<400> SEQUENCE: 48

Ile Lys Met Val Ile Ser Trp Xaa Xaa
1               5

<210> SEQ ID NO 49
<211> LENGTH: 8
<212> TYPE: PRT
<213> ORGANISM: Artificial Sequence
<220> FEATURE:
<223> OTHER INFORMAT

```
<220> FEATURE:
<221> NAME/KEY: misc_feature
<222> LOCATION: (7)..(8)
<223> OTHER INFORMATION: Xaa can be any naturally occurring amino acid

<400> SEQUENCE: 49

Lys Met Val Ile Ser Trp Xaa Xaa
1               5

<210> SEQ ID NO 50
<211> LENGTH: 9
<212> TYPE: PRT
<213> ORGANISM: Artificial Sequence
<220> FEATURE:
<223> OTHER INFORMATION: HYD1 variant
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 50

Xaa Lys Met Val Ile Ser Trp Xaa Xaa
1               5
```

HYD1 PEPTIDES AS ANTI-CANCER AGENTS

CROSS-REFERENCE TO RELATED APPLICATIONS

The present application claims the benefit of U.S. Provisional Application Ser. No. 60/824,838, filed Sep. 7, 2006, and U.S. Provisional Application Ser. No. 60/944,160, filed Jun. 15, 2007, each of which is hereby incorporated by reference herein in its entirety, including any figures, tables, nucleic acid sequences, amino acid sequences, and drawings.

GOVERNMENT SUPPORT

The subject matter of this application has been supported by a research grant from the National Institutes of Health under grant number CA077859. Accordingly, the government has certain rights in this invention.

BACKGROUND OF THE INVENTION

Many tumor types will often initially respond to chemotherapy treatment. However, successful treatment of these diseases is limited by the failure to eliminate minimal residual disease (MRD). Moreover, relapse is often associated with a multi-drug resistant phenotype that contributes to decreased chemotherapy sensitivity and failure of salvage treatment. Acquired drug resistance entails a great deal of genomic complexity, which dramatically increases the difficulty in managing such diseases. The present inventors propose that a viable strategy for enhancing the efficacy of currently used cytotoxics is to identify targets which contribute to de novo drug resistance thereby increasing the efficacy and success of initial therapy intervention and decreasing relapse rates. By definition, de novo drug resistance is represented by mechanisms, which do not require drug selection for the expression of the phenotype. De novo drug-resistant models are in contrast to historical drug-resistant models, which have been based upon unicellular drug selections over time, thereby excluding the impact of tumor cell interaction with the microenvironment on drug response (see FIG. 1).

The present inventors demonstrated that components of the tumor microenvironment influence the response of hematopoietic cell lines to chemotherapeutics and could contribute to de novo resistance. Specifically, it has been shown that adhesion of leukemia and multiple myeloma cell lines to the extracellular matrix component, fibronectin (FN) via β1 integrin, is sufficient to inhibit drug-induced apoptosis. (Hazlehurst L A, et al. *Oncogene.* 2000; 19:4319-4327; Hazlehurst L A, et al. *Cancer Res.* 2003; 63:7900-7906; Hazlehurst L A, et al. *Blood.* 2001; 98:1897-1903; Hazlehurst L A, et al. *Cancer Res.* 2006; 66:2338-2345; Hazlehurst L A, et al. *Cancer Metastasis Rev.* 2001; 20:43-50; Hazlehurst L A, et al. *Cancer Res.* 1999; 59:1021-1028; Hazlehurst L A, et al. *Biochem Pharmacol.* 1995; 50:1087-1094; Hazlehurst L A, et al. *Oncogene.* 2003; 22:7396-7402). More recently, it was shown that the cell adhesion induced drug resistance (CAM-DR) phenotype is operative in clinical samples taken from primary multiple myeloma (Hazlehurst L A, et al. *Cancer Res.* 2003; 63:7900-7906). Together, these data suggest that adhesion of hematopoietic tumor cells to FN could contribute to the failure of currently used cytotoxics to eradicate the entire disease and may facilitate the subsequent emergence of clinical drug resistance.

The emergence of drug-resistant tumor cells remains an obstacle to the successful treatment of many hematopoietic malignancies, including Acute Myeloid Leukemia (AML), Multiple Myeloma, and Chronic Myelogenous Leukemia (CML). Our laboratory, along with others, has previously shown that cell adhesion via β1 integrins is sufficient to cause drug resistance (Chrenek M A, et al. *Breast Cancer Res.* 2001; 3:224-229; Damiano J S, et al. *Blood.* 1999; 93:1658-1667; Damiano J S, et al. *Leukemia.* 2001; 15:1232-1239; de la Fuente M T, et al. *J Leukoc Biol.* 2002; 71:495-502; Hazlehurst L A, et al. *Oncogene.* 2000; 19:4319-4327; Hazlehurst L A, et al. *Cancer Res.* 2003; 63:7900-7906; Hazlehurst L A, et al. *Blood.* 2001; 98:1897-1903; Sethi T, et al. *Nat Med.* 1999; 5:662-668; Sherman-Baust C A, et al. *Cancer Cell.* 2003; 3:377-386).

β1 integrin mediated cell adhesion is a clinically relevant mechanism whereby tumor cells can evade cell death induced by chemotherapy. In support of this hypothesis, the inventors have previously shown that cell adhesion via β1 integrins to the extracellular matrix fibronectin confers a multi-drug resistance phenotype. As indicated above, the inventors have referred to that phenotype as CAM-DR. Moreover, the inventors have validated the CAM-DR phenotype in primary myeloma patient specimens. More recently, the inventors have shown that co-culturing tumor cells with a bone marrow stroma cell whereby tumor cells are in direct contact with the bone marrow stroma cell line confers drug resistance. The present inventors have referred to this phenotype as environmental mediated drug resistance or EMDR. Due to the in vitro findings, the inventors hypothesized that targeting β1 integrin mediated cell adhesion will increase the efficacy of drugs used to treat cancers.

The development of target based drug discovery has provided novel approaches for the treatment of hematopoietic malignancies. However, despite the recent advances in drug discovery it is clear that rationally designed chemotherapeutics such as the BCR-ABL kinase inhibitor imanitib, although effective, do not circumvent the emergence of clinical drug resistance (Buchdunger E, et al. *Cancer Res.* 1996; 56:100-104; Druker B J, et al. *Nat Med.* 1996; 2:561-566; Gorre M E, et al. *Science.* 2001; 293:876-880; Hochhaus A, et al. *Science.* 2001; 293:2163; Sawyers C L. *Science.* 2001; 294:1834). These data support the importance of identifying and targeting drug resistant mechanism(s) as a viable strategy for improving the efficacy of cancer chemotherapy. A cancer cell can employ multiple strategies that ultimately favor survival following cytotoxic insult. These mechanisms include decreased drug uptake, increased drug efflux, alterations in the drug target, drug metabolism, repair of DNA damage, cell cycle checkpoint mediators, and changes in downstream mediators of the apoptotic pathway.

Traditionally, drug resistance mechanisms have been identified and functionally characterized in unicellular models. However, unicellular models lack consideration of host-tumor cell interactions that may participate in the emergence of the drug resistant phenotype. We propose that the initial selection pressure for tumor growth and survival is represented by host-tumor cell interactions and furthermore, these same interactions may participate in modulating drug response and emergence of drug resistance. Indeed, Teicher et al provided experimental data supporting this concept (Teicher B A, et al. *Science.* 1990; 247:1457-1461). These investigators showed that treatment of mice bearing EMT-6 mammary tumors over a six-month period with alkylating agents resulted in the selection of a drug resistance phenotype that was operative only in-vivo. Conversely, the resistance phenotype was not detected in a unicellular tissue culture system indicating the importance of the microenvironment in mediating the expression of a functional drug resistance phenotype. Thus we suggest that in order to identify clinically relevant de-novo drug resistant targets new models must be developed allowing for reconstitution of complex host-tumor cell interactions.

The first model demonstrating the survival effects of cell adhesion was developed by Durand and Sutherland in 1972 (Durand R E, S et al. *Exp Cell Res.* 1972, 71:75-80). In this model, they demonstrated that forcing V79 Chinese hamster cells to grow in a spheroid culture was causative for radiation resistance relative to cells treated as a monolayer. The implication of the spheroid model is that cell-cell contact may enhance survival of tumor cells in response to cytotoxic stimuli. Unlike solid tumors, most hematopoietic tumors do not grow as a spheroid in-vivo. However, as the knowledge of adhesion receptors, ligands and counter-receptors has grown, it is apparent that hematopoietic cells maintain a dynamic relationship with the bone marrow stroma and components of the extracellular matrix. Furthermore, it is well documented that adhesion molecules participate in the growth, differentiation, survival and homing of hematopoietic cells (Bohnsack J F, et al. *Blood.* 1994; 83:543-552; Hamdan H F, et al. *Oncol Res.* 1992; 4:201-207; Potocnik A J, et al. *Immunity.* 2000; 12:653-663; Wang M W, et al. *Cell Growth Differ.* 1998; 9:105-112).

Cellular adhesion taken in context within the entire microenvironment is multifactorial. However, of these adhesion molecules identified in hematopoietic cells, integrins are the best characterized for their role in regulating cell growth, survival, differentiation and homing to the bone marrow. Integrin receptors are comprised of non-covalently associated heterodimeric subunits. The integrin receptors contain both an alpha and beta subunit. To date, 17α and 8β subunits have been identified. Among the integrin family, VLA-4 (α4β1) and VLA-5 (α5β1) integrins are the most commonly reported integrin receptors expressed in AML (Vila L, et al. *Exp Hematol.* 1995; 23:514-518) and multiple myeloma (Cook G, et al. *Acta Haematol.* 1997; 97:81-89).

The inventors' initial observations using cellular adhesion to FN as a model system for investigating CAM-DR was done in multiple myeloma cell lines (Damiano J S, et al. Blood. 1999; 93:1658-1667). Myeloma is a disease that homes to the bone marrow and is characterized by the accumulation of plasma cells in the bone marrow. But multiple myeloma is not the only hematopoietic malignancy in which CAM-DR may contribute to disease progression and drug resistance. It is well accepted that initial chemotherapy of CML and AML results in rapid clearing of detectable disease in the peripheral blood. However, elimination of disease in the bone marrow is a more arduous task, suggesting that de-novo drug resistance associated with the bone marrow microenvironment may contribute to residual disease. Consistent with these clinical observations, the present inventors shown a similar CAM-DR phenotype in CML and AML cell lines, indicating that adhesion mediated drug resistance may impact several malignancies (Damiano J S, et al. *Leukemia.* 2001; 15:1232-1239; Hazlehurst L A, et al. *Blood.* 2001; 98:1897-1903). In addition, Matsunaga et al. recently showed in a mouse model of AML minimal residual disease (MRD) that treatment with a VLA-4 specific antibody and AraC significantly increased survival compared to treatment with AraC alone (Matsunaga T, et al. *Nat. Med.* 2003; 9:1158-1165). The inventors propose that cell adhesion maybe a key determinant of de-novo drug resistance and failure to eliminate MRD in AML.

Despite recent advances in the treatment of multiple myeloma, the disease remains incurable. Due to the inherent resistance associated with myeloma identification of targets contributing to failure to eliminate minimal residual disease remains in area of active research. As indicated above, myeloma typically homes to the bone marrow, and this specialized environment may contribute to failure to eliminate minimal residual disease. The bone marrow microenvironment represents an area that is enriched in deposition of extracellular matrixes. The inventors previously showed that adhesion of myeloma cells to the extrallular matrix fibronectin (FN) inhibits apoptosis induced by mechanistically and structurally diverse chemotherapeutic agents (Damiano J S et al. *Blood,* 1999; 93:1658-1667; Hazlehurst L A et al. *Oncogene,* 2000; 19:4319-4327; Hazlehurst L A et al. *Cancer Res.,* 2003; 63:7900-7906). Moreover, the inventors recently demonstrated that adhesion of primary patient multiple myeloma specimens to FN protects multiple myeloma cells form melphalan induced apoptosis (Hazlehurst L A et al. *Cancer Res.,* 2003; 63:7900-7906). Taken together, our previous data indicates that targeting FN receptors (VLA-4, VLA-5 integrins) and/or signaling may enhance the efficacy of cytotoxic agents used to treat multiple myeloma.

VLA-4 and VLA-5 integrins are the most common integrins expressed on myeloma cells (Van Riet I et al. *Br J. Haematol.,* 1991; 79:421-427). These two integrin receptors are both comprised of a β1 subunit, and experimental evidence indicates that downstream signaling occurs through the β1 integrin cytoplasmic tail region. β1 integrins are reported to activate a complex network of signaling, which includes activation of Mapk, Akt, Fak/Pyk2 and integrin linked kinase or ILK (Astier A et al. *J Biol. Chem.,* 1997; 272:19719-19724; Chen Q et al. *J Biol. Chem.,* 1996; 271:18122-18127; King W G et al. *Mol Cell Biol.,* 1997; 17:4406-4418; Schaller M D and Parsons J T et al. *Mol Cell Biol.,* 1995; 15:2635-2645; Schlaepfer D D et al. *Nature,* 1994; 372:786-791; Hannigan G E et al. *Nature,* 1996; 379:91-96). In addition, the present inventors recently showed that adhesion of myeloma and leukemia cells to FN reduced the levels of the pro-apoptotic Bcl-2 family member Bim (Hazlehurst L A et al. *British Journal Haematology,* 2007; 136(2):269-75).

BRIEF SUMMARY OF THE INVENTION

The inventors have identified peptides capable of inducing cell death in cancer cells. Without being limited by theory, the peptides bind β1 containing integrin and thereby inhibit β1 integrin-mediated adhesion. Treatment with the peptide inhibitors of β1 integrin-mediated adhesion potentiates drug induced cell death in an EMDR model. Together, the data indicate β1 integrins are a critical determinant of EMDR and that binding β1 integrin can increase the efficacy of chemotherapy and radiation therapy, particularly in the bone marrow microenvironment.

Due to the multiplicity of β1 integrin signaling and potential multiple downstream targets that may contribute to drug resistance, it was postulated that targeting the receptor was a reasonable strategy to determine if blocking β1 integrin binding and hence signaling would enhance the efficacy of standard therapy. To this end, the inventors explored the mechanism of action of a β1-integrin inhibitory peptide referred to as HYD1 (DeRoock I B et al. *Cancer Res.,* 2001; 61:3308-3313; Pennington M E et al. *Mol Divers,* 1996; 2:19-28; Sroka T C et al. *Carcinogenesis,* 2006; 27(9):1748-57). HYD1 is a D-amino acid peptide (comprised of all D-amino acids) that was previously shown to block β1 integrin-mediated adhesion of prostate carcinoma cells to FN, laminin 1, laminin 5 and collagen IV. The present inventors have determined that HYD1 does indeed reverse resistance associated with a bone marrow stroma co-culture model. However, an unanticipated result was that HYD1 has activity as a single agent when myeloma cells are cultured in suspension. Furthermore HYD1 enhanced melphalan induced cell death in both suspension and co-culture models. The mechanism of cell death induced by HYD1 is independent of caspase activation and experimental evidence indicates that HYD1 induces autophagy. Finally, using a SCID-Hu model, the inventors show that HYD1 has activity as a single agent in vivo. These results provide the basis using HYD1 in multiple myeloma and other tumors that display the CAM-DR phenotype, including AML, CML, lymphoma breast and lung (Damiano J S et al. *Blood,* 1999; 93:1658-1667; Hazlehurst L A et al. *Oncogene,* 2000; 19:4319-4327; Hazlehurst L A et al. *Cancer Res.,* 2003; 63:7900-7906; Hazlehurst L A et al. *British Journal Haematology,* 2007; 136(2):269-75; Aoudjit F and Vuori K. *Oncogene,* 2001; 20:4995-5004; Damiano J S et al. *Leukemia,* 2001; 15:1232-1239; Hazlehurst L A et al. *Cancer Res.,* 2006; 66:2338-2345; Hazlehurst L A et al. *Blood,* 2001; 98:1897-1903; Sethi T et al. *Nat. Med.,* 1999; 5:662-668; Lwin T et al *Blood,* 2007; 110(5):1631-8).

It is well established that many cancer cells can die through apoptosis or programmed cell death (type I cell death). However, tumor progression and relapse is often associated with tumor cells becoming resistant to apoptotic stimuli. Autophagy ("self-eating") can under the appropriate context result in an alternative mechanism of cell death that is independent of the activation of caspases (type II cell death). Autophagy is characterized by the formation of double membrane containing vesicles that sequester cytoplasm and organelles. These double membrane vesicles are then delivered to the lysosome for bulk degradation of contents.

Most of the anti-cancer agents used clinically target the type I cell death pathway. The results described herein indicate that HYD1 induces cell death though in an autophagic or type II mechanism of cell death. Targeting a type II cell death pathway is attractive as it is currently under utilized in the treatment of cancer, and may be an effective strategy for combining existing chemotherapeutics to enhance tumor cell kill. Indeed, data presented herein showing that HYD1 treatment enhances melphalan cell death in vitro and in vivo suggest that initiating both cell death pathways is an advantageous strategy for enhancing tumor cell kill of conventional chemotherapy.

The present invention concerns isolated peptides, polynucleotides encoding the peptides, compositions containing these peptides or polynucleotides, and methods of using these peptides (or encoding polynucleotides and operably linked promoters) and compositions as inhibitors of β1 integrin mediated adhesion and/or as inhibitors of aberrant cell growth, e.g., as anti-cancer agents through induction of cell death. In one embodiment, the peptide comprises an amino acid sequence selected from among KIKMVISWKG (HYD1; SEQ ID NO:1); AIAMVISWAG (SEQ ID NO:2; HYD8); AIKMVISWAG (SEQ ID NO:3; HYD6); AIKMVISWKG (SEQ ID NO:4; HYD2); AKMVISW (SEQ ID NO:5); AKMVISWKG (SEQ ID NO:6); IAMVISW (SEQ ID NO:7); IAMVISWKG (SEQ ID NO:8); IKAVISW (SEQ ID NO:9); IKAVISWKG (SEQ ID NO:10); IKMAISW (SEQ ID NO:11); IKMAISWKG (SEQ ID NO:12); IKMVASW (SEQ ID NO:13); IKMVASWKG (SEQ ID NO:14); IKMVIAW (SEQ ID NO:15); IKMVIAWKG (SEQ ID NO:16); IKMVISA (SEQ ID NO:17); IKMVISAKG (SEQ ID NO:18); IKMVISW (SEQ ID NO:19); IKMVISWAG (SEQ ID NO:20); KMVISWKA (SEQ ID NO:21); IKMVISWKG (SEQ ID NO:22; HYD18; (-K)HYD1); ISWKG (SEQ ID NO:23); KAKMVISWKG (SEQ ID NO:24); KIAMVISWAG (SEQ ID NO:25; HYD7); KIAMVISWKG (SEQ ID NO:26); KIKAVISWKG (SEQ ID NO:27); KIKMAISWKG (SEQ ID NO:28); KIKMV (SEQ ID NO:29); KIKMVASWKG (SEQ ID NO:30); KIKMVI (SEQ ID NO:31; HYD16); KIKMVIAWKG (SEQ ID NO:32); KIKMVIS (SEQ ID NO:33; HYD15); KIKMVISAKG (SEQ ID NO:34); KIKMVISW (SEQ ID NO:35; HYD14); KIKMVISWAG (SEQ ID NO:36); KIKMVISWK (SEQ ID NO:37; HYD17; HYD1(−G)); KIKMVISWKA (SEQ ID NO:38); KMVISWKG (SEQ ID NO:39; HYD9); LSWKG (SEQ ID NO:40; HYD12); MVISWKG (SEQ ID NO:41; HYD10); SWKG (SEQ ID NO:42; HYD13); VISWKG (SEQ ID NO:43; HYD11); WIKSMKIVKG (SEQ ID NO:44); KMVIXW (SEQ ID NO:46); IKMVISWXX (SEQ ID NO:48); and KMVISWXX (SEQ ID NO:49); wherein X is any amino acid (traditional or non-traditional amino acid). In another embodiment, the peptide consists of the amino acid sequence. In another embodiment, the peptide consists essentially of the amino acid sequence. In another embodiment, the peptide is one listed in the figures herein. In one embodiment, the peptide is one of the variants listed in FIG. 14A-14C, 15A-15C, or 16A-1-16C-2 that is substituted with an alanine at one position, and wherein another residue is substituted in place of the alanine. Preferably, the residue is a conservative substitution.

Preferably, the peptide comprises at least one D-amino acid. More preferably, each amino acid of the peptide is a D-amino acid.

One aspect of the invention concerns a method of treating a proliferation disorder such as cancer in a human or animal subject, comprising administering an effective amount of at least one peptide of the invention to the subject. In one embodiment, the proliferation disorder is cancer. In another embodiment, the proliferation disorder is cancer and the cancer cells are in suspension, e.g., part of a circulating tumor cell (CTC) population, and the peptides kill the CTC. In another embodiment, the peptides of the invention prevent or delay onset of metastasis of the cancer cells (e.g., to the bone). In one embodiment, the disorder is mediated by cells that exhibit the cell adhesion induced drug resistance (CAM-DR) phenotype.

Another aspect of the invention concerns a method of suppressing the growth of malignant cells, comprising contacting the cells in vitro or in vivo with an effective amount of at least one peptide of the invention. In one embodiment, the malignant cells exhibit the CAM-DR phenotype.

Another aspect of the invention concerns a method of inducing apoptosis in malignant cells, comprising contacting the cells in vitro or in vivo with an effective amount of at least one peptide of the invention (or a polynucleotide comprising a nucleic acid sequence encoding the peptide, wherein the polynucleotide is operably linked to a promoter). In one embodiment, the malignant cells are in suspension, e.g., part of a circulating tumor cell (CTC) population, and the peptides kill the CTC. In another embodiment of the in vivo method, the peptides of the invention prevent or delay onset of metastasis (e.g., to the bone). In one embodiment, the malignant cells exhibit the CAM-DR phenotype. Without being bound by theory, it is proposed that the peptides of the invention induce cell death by cell surface binding and activation of a non-caspase dependent cell death mechanism involving autophagy.

Another aspect of the invention concerns a method of inhibiting (e.g., reducing, interfering with, or disrupting) β1 integrin mediated adhesion, comprising contacting cells in vitro or in vivo with an effective amount of at least one peptide of the invention (or a polynucleotide comprising a nucleic acid sequence encoding the peptide, wherein the polynucleotide is operably linked to a promoter).

Another aspect of the invention concerns a method for increasing the efficacy of chemotherapy or radiation therapy in a subject, comprising administering at least one agent that binds β1 integrin or inhibits (e.g., disrupts or reduces) β1 integrin mediated adhesion in the subject. Preferably, the method further comprises administering the chemotherapy and/or radiation treatment to the subject before, during, or after administration of the agent, wherein the effectiveness of the treatment is increased. In one embodiment, the agent is a peptide of the invention or a polynucleotide encoding the peptide. Other examples of agents include VLA-4 antibody (alpha 4 beta 1 integrin), and integrin linked kinase inhibitors.

In another aspect, the invention pertains to an adhesion trap comprising a substrate (surface) with a HYD1 peptide, or fragment or variant thereof, immobilized to the surface, and a method of removing circulating tumor cells (CTC) from blood by contacting a subject's blood with the immobilized peptide.

Another aspect of the invention concerns a method of identifying modulators of peptide binding (a screen for molecules that displace peptide binding), the method comprising providing a candidate agent (such as a chemical compound, antibody, nucleic acid, or peptide); and determining whether the agent inhibits (e.g., disrupts, prevents, or interferes with), the ability of a peptide of the invention (HYD1 or a fragment or variant thereof) to bind to β1 integrin on a cancer cell surface and/or inhibit β1 integrin mediated adhesion, in vitro or in vivo (e.g., in an animal model). Preferably, the peptide is labeled with a detectable moiety (e.g., fluorescently) to facilitate the determining step. The determining step can be carried out by contacting the candidate agent with the cells in the presence of the peptide. Optionally, the peptides may be immobilized on a surface or in suspension.

In another aspect, the invention concerns a method for detecting circulating tumor cells (CTC). Thus, the invention includes an in vitro screening assay for detecting CTC in a biological sample from a subject (such as peripheral blood), comprising obtaining a biological sample from a subject; and determining whether the peptide of the invention binds to cells (β1 integrin on the cell surface) in the sample. Preferably, the peptide is labeled with a detectable moiety (e.g., fluorescently) to facilitate the determining step. The peptide binding can be carried out using flow cytometry analysis or in tandem with CTC detection machines, for example. Optionally, the peptides may be immobilized on a surface, or in suspension. In another embodiment, the peptides of the invention can be tested for potency by determining their ability to prevent or interfere with the binding of labeled ligand to target cells. In this case, the ligand is labeled and incubated in the presence of the test cells and unlabelled peptides.

Another aspect of the invention concerns an in vitro screening test for the presence of malignant cells in a mammalian tissue, the test including: obtaining a sample containing viable cells of the tissue; culturing the sample under conditions promoting growth of the viable cells contained therein; treating the cultured sample with a peptide of the invention; and analyzing the treated sample by a method effective to determine percent apoptosis of cells as an indicator of presence of malignant cells in the sample.

BRIEF DESCRIPTION OF THE DRAWINGS

For a fuller understanding of the invention, reference should be made to the following detailed description, taken in connection with the accompanying drawings, in which:

As shown in FIG. 3A, tumor cells are cultured in regular media (RM). As shown in FIG. 3B, conditioned media is collected from HS-5 cultures (CM). As shown in FIG. 3C, tumor cells are exposed to soluble factors from HS-5 cells—the top chamber of a transwell culture dish (SF). As shown in FIG. 3D, tumor cells are exposed to soluble factors and adherent to HS-5 cells (SF+A).

As shown in FIG. 9A, MM cells are cultured in regular media (RM). As shown in FIG. 9B, MM cells are exposed to soluble factors from HS-5 cells—the top chamber of a transwell culture dish (SF). As shown in FIG. 9C, tumor cells are exposed to soluble factors and adherent to HS-5 cells (SF+A).

FIG. 14A shows the results of alanine substitution analysis of a portion of the HYD1 peptide. Listed in FIG. 14A are the fragment ikmvisw (SEQ ID NO:19) and the variants akmvisw (SEQ ID NO:5), iamvisw (SEQ ID NO:7), ikavisw (SEQ ID NO:9), ikmaisw (SEQ ID NO:11), ikmvasw (SEQ ID NO:13), ikmviaw (SEQ ID NO:15), and ikmvisa (SEQ ID NO:17). FIG. 14B shows the results of systematic truncation of the N and C terminus of the HYD1 peptide. Listed in FIG. 14B are the fragments ikmviswkg (SEQ ID NO:22), kmviswkg (SEQ ID NO:39), mviswkcg (SEQ ID NO:41), viswkg (SEQ ID NO:43), iswkg (SEQ ID NO:23), kikmviswk (SEQ ID NO:37), kikmvisw (SEQ ID NO:35), kikmvis (SEQ ID NO:33), kikmvi (SEQ ID NO:31), and kikmv (SEQ ID NO:29), containing all D-amino acids. FIG. 14C shows a summary of the results, indicating that the minimal element necessary for cell adhesion is kmvixw (SEQ ID NO:46).

FIG. 15A shows the results of alanine substitution analysis of the HYD1 peptide. Listed in FIG. 15A are HYD1, HYDS, and the variants aikmviswkg (SEQ ID NO:4), kakmviswkg (SEQ ID NO:24), kiamviswkg (SEQ ID NO:26), kikaviswkg (SEQ ID NO:27), kikmaiswkg (SEQ ID NO:28), kikmvaswkg (SEQ ID NO:30), kikmviawkg (SEQ ID NO:32), kikmvisakg (SEQ ID NO:34), kikmviswag (SEQ ID NO:36), and kikmviswka (SEQ ID NO:38), containing all D-amino acids. FIG. 15C shows a summary of the results, showing that the element required to maximally block cell migration was xkmviswxx (SEQ ID NO:50), and suggesting that the active sequence for blocking cell migration is kmvisw (SEQ ID NO:45).

FIGS. 16A-1-16C2 show the results of a further truncation and substitution study of the HYD1 peptide, establishing the sequence required for activation of ERK signaling. Listed in FIGS. 16A-1 and 16A-2 are HYD1, HYDS, and the variants aikmviswkg (SEQ ID NO:4), kakmviswkg (SEQ ID NO:24), kiamviswkg (SEQ ID NO:26), kikaviswkg (SEQ ID NO:27), kikmaiswkg (SEQ ID NO:28), kikmvaswkg (SEQ ID NO:30), kikmviawkg (SEQ ID NO:32), kikmvisakg (SEQ ID NO:34), kikmviswag (SEQ ID NO:36), and kikmviswka (SEQ ID NO:38). Listed in FIGS. 16B and 16C-1 are HYD1, HYDS, and the fragments iswkg (SEQ ID NO:23), viswkg (SEQ ID NO:43), mviswkg (SEQ ID NO:41), kmviswkg (SEQ ID NO:39), ikmviswkg (SEQ ID NO:22), kikmv (SEQ ID NO:29), kikmvi (SEQ ID NO:31), kikmvis (SEQ ID NO:33), kikmvisw (SEQ ID NO:35), and kikmviswk (SEQ ID NO:37), containing all D-amino acids. FIG. 16C-2 shows a summary of the results, indicating that activation of ERK signaling required ikmviswxx (SEQ ID NO:48).

FIGS. 20A-20F show that ZVAD-FMK blocks melphalan but not HYD1 induced apoptosis. 200 µM ZVAD-FMK was added to H929 cells for 30 minutes prior to the addition of either 75 µg/ml HYD1S or 15 µM Melphalan. Apoptosis was measured 24 hours after drug treatment by annexin/PI staining and apoptotic cells were detected by FACS analysis. Three independent experiments were performed and shown is a representative experiment.

FIGS. 23A-23L show that H929 cells (FIGS. 23A-23F) and 8266 cells (FIGS. 23G-23L) treated with 100 µg/ml HYD1 for six hours show an increase in number and size of acidic vesicles. Lysosensor green was used to detect acidic compartments and live cell imaging was performed by confocal microscopy. Shown is a representative figure. The experiment was repeated three independent times and similar results were obtained.

In FIGS. 35 and 36, the evaluated peptides included HYD1 (kikmviswkg; SEQ ID NO:1); HYD1S (wiksmkivkg; SEQ ID NO:44), which contained all D-amino acids. The remaining peptides contained all L-amino acids: HYD2 (AIKMVISWKG; SEQ ID NO:4); HYD6 (AIKMVISWAG; SEQ ID NO:3); HYD7 (KIAMVISWAG; SEQ ID NO:25); HYD8 (AIAMVISWAG; SEQ ID NO:2); HYD9 (KMVISWKG; SEQ ID NO:39); HYD10 (MVISWKG; SEQ ID NO:41); HYD11 (VISWKG; SEQ ID NO:43); HYD12 (LSWKG; SEQ ID NO:40); HYD13 (SWKG; SEQ ID NO:42); HYD14 (KIKMVISW; SEQ ID NO:35); HYD15 (KIKMVIS; SEQ ID NO:33); HYD16 (KIKMVI; SEQ ID NO:31); HYD17 (KIKMVISWK; SEQ ID NO:37); and HYD18 (IKMVISWKG; SEQ ID NO:22).

FIG. 36 is a graph showing the effect of HYD1 fragments and variants on apoptosis in H929 cells (same peptides evaluated in FIG. 35). H929 cells were incubated with the indicated D-amino acid peptides or L-amino acid peptides (25 ug/ml) for 24 hrs. Following peptide treatment, apoptotic cells were measured by annexin V staining and FACS analysis.

BRIEF DESCRIPTION OF THE SEQUENCES

Figure 1:
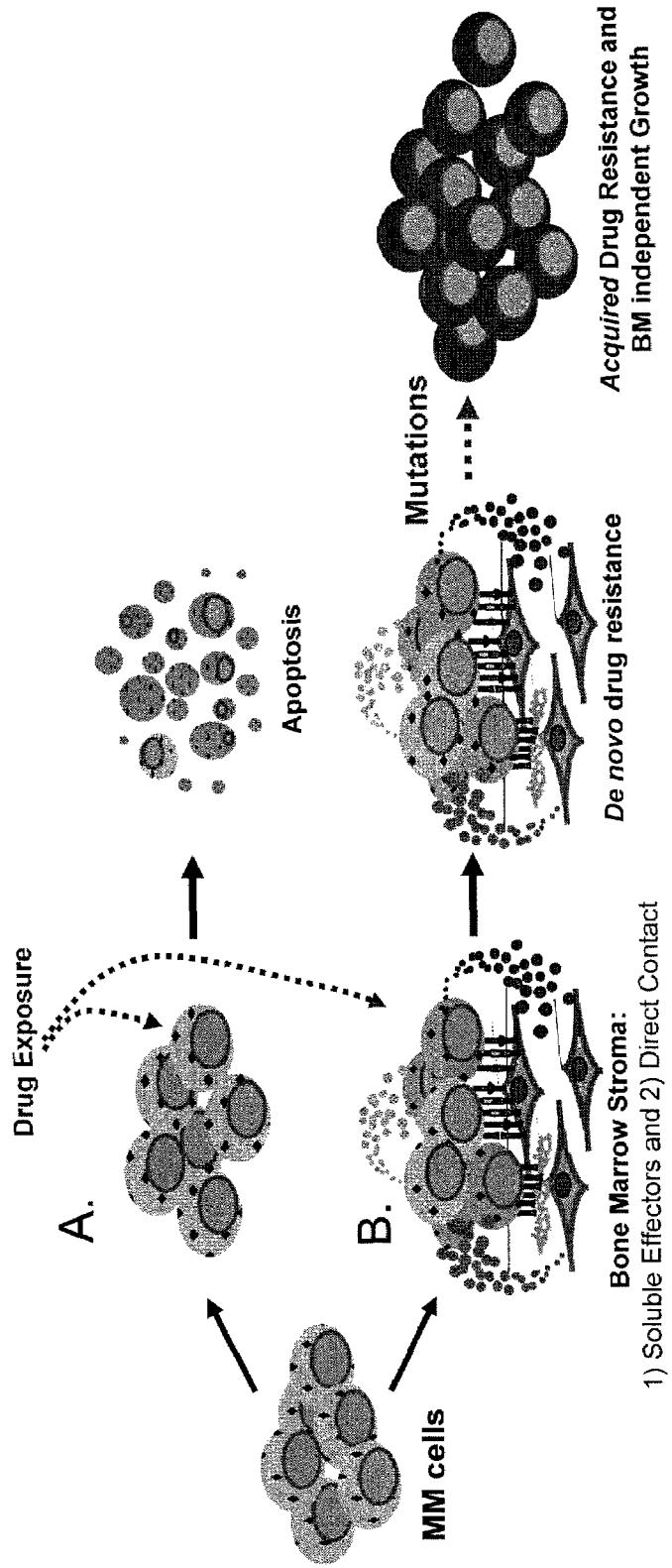
FIG. 1 is a model of the influence of BMS cells on CAM-DR of the tumor cell and acquisition of acquired drug resistance. The inventors hypothesize that at any given point in time a subpopulation of hematopoietic tumor cells adherent to extracellular matrixes deposited by the BMS cells via β1 integrins (A) allows for cell survival following drug exposure relative to cells "distant" from BMS (B). Furthermore, the inventors propose that disruption of β1 integrin mediated tumor cell adhesion will increase the efficacy of cytotoxics and reduce minimal residual disease associated with the treatment of many hematopoietic malignancies.

```
SEQ ID NO:1 is the amino acid sequence
KIKMVISWKG (HYD1).

SEQ ID NO:2 is the amino acid sequence
AIAMVISWAG (HYD8).

SEQ ID NO:3 is the amino acid sequence
AIKMVISWAG (HYD6).

SEQ ID NO:4 is the amino acid sequence
AIKMVISWKG (HYD2).

SEQ ID NO:5 is the amino acid sequence
AKMVISW.

SEQ ID NO:6 is the amino acid sequence
AKMVISWKG.

SEQ ID NO:7 is the amino acid sequence
IAMVISW.

SEQ ID NO:8 is the amino acid sequence
IAMVISWKG.

SEQ ID NO:9 is the amino acid sequence
IKAVISW.

SEQ ID NO:10 is the amino acid sequence
IKAVISWKG.

SEQ ID NO:11 is the amino acid sequence
IKMAISW.

SEQ ID NO:12 is the amino acid sequence
IKMAISWKG.

SEQ ID NO:13 is the amino acid sequence
IKMVASW.

SEQ ID NO:14 is the amino acid sequence
IKMVASWKG.

SEQ ID NO:15 is the amino acid sequence
IKMVIAW.

SEQ ID NO:16 is the amino acid sequence
IKMVIAWKG.

SEQ ID NO:17 is the amino acid sequence
IKMVISA.

SEQ ID NO:18 is the amino acid sequence
IKMVISAKG.

SEQ ID NO:19 is the amino acid sequence
IKMVISW.

SEQ ID NO:20 is the amino acid sequence
IKMVISWAG.

SEQ ID NO:21 is the amino acid sequence
KMVISWKA.
```

-continued

SEQ ID NO:22 is the amino acid sequence IKMVISWKG (HYD18; (-K)HYD1).

SEQ ID NO:23 is the amino acid sequence ISWKG.

SEQ ID NO:24 is the amino acid sequence KAKMVISWKG.

SEQ ID NO:25 is the amino acid sequence KIAMVISWAG (HYD7).

SEQ ID NO:26 is the amino acid sequence KIAMVISWKG.

SEQ ID NO:27 is the amino acid sequence KIKAVISWKG.

SEQ ID NO:28 is the amino acid sequence KIKMAISWKG.

SEQ ID NO:29 is the amino acid sequence KIKMV.

SEQ ID NO:30 is the amino acid sequence KIKMVASWKG.

SEQ ID NO:31 is the amino acid sequence KIKMVI (HYD16).

SEQ ID NO:32 is the amino acid sequence KIKMVIAWKG

SEQ ID NO:33 is the amino acid sequence KIKMVIS (HYD15).

SEQ ID NO:34 is the amino acid sequence KIKMVISAKG.

SEQ ID NO:35 is the amino acid sequence KIKMVISW (HYD14).

SEQ ID NO:36 is the amino acid sequence KIKMVISWAG.

SEQ ID NO:37 is the amino acid sequence KIKMVISWK (HYD 17; HYD1(-G)).

SEQ ID NO:38 is the amino acid sequence KIKMVISWKA.

SEQ ID NO:39 is the amino acid sequence KMVISWKG (HYD9).

SEQ ID NO:40 is the amino acid sequence LSWKG (HYD12).

SEQ ID NO:41 is the amino acid sequence MVISWKG (HYD10).

SEQ ID NO:42 is the amino acid sequence SWKG (HYD13).

SEQ ID NO:43 is the amino acid sequence VISWKG (HYD11).

SEQ ID NO:44 is the amino acid sequence WIKSMKIVKG.

SEQ ID NO:45 is the amino acid sequence KMVISW.

SEQ ID NO:46 is the amino acid sequence KMVIXW.

SEQ ID NO:47 is the amino acid sequence IKMVISWK.

SEQ ID NO:48 is the amino acid sequence IKMVISWXX.

-continued

SEQ ID NO:49 is the amino acid sequence KMVISWXX.

SEQ ID NO:50 is the amino acid sequence XKMVISWXX.

DETAILED DESCRIPTION OF THE INVENTION

The data presented herein show that the HYD1 peptide has anti-tumor activity as a single agent (i.e., with or without the addition of additional anti-cancer agents). HYD1 is a D-amino acid containing peptide (kikmviswkg; SEQ ID NO:1). HYD1 was initially discovered via combinatorial peptide chemistry using a functional adhesion assay as a screening tool. This peptide has been shown to block beta 1 integrin mediated cell adhesion. The present inventors have determined that HYD1 induces apoptosis as a single agent in vitro and in vivo. Furthermore, the mechanism of action is independent of caspase activation and experimental evidence suggests that HYD1 induces autophagy.

HYD1 was observed to induce apoptosis as measured by annexin V positive cells. H929 or 8226 cells were treated with varying doses of HYD1 for 24 hours and dead cells were measured by annexin V positivity as determined by FACS analysis. In addition, HYD1 treatment reduces 8226 MM growth in vivo compared to vehicle control treatment. Tumor burden was measured by circulating lambda levels. On day 28 (before drug treatment), measurements were recorded for each individual mouse and subsequent values obtained weekly are represented as a ratio of day 28 (day X/day 28). N=4 mice per group. HYD1 was administered I.P. at mg/kg daily for 14 days (starting day 28). Melphalan was administered I.P. at 1.5 mg/kg on day 29 and 33.

HYD1 is a peptide that binds and inhibits β1 integrin-mediated adhesion. The present inventors have demonstrated that HYD1 potentiates melphalan-induced cell death. Allowing direct contact between tumor cells and the bone marrow stroma cell line HS-5 is sufficient to confer a multi-drug resistant phenotype. The inventors have demonstrated that HYD1 potentiates meiphalan induced cell death in multiple myeloma cell lines that are co-cultured with the HS-5 cell line.

The present invention provides methods of increasing the efficacy of chemotherapy, comprising administering an agent that binds β1 integrin to a human or animal patient in need thereof. In certain aspects, the binding of β1 integrin by the administered agent inhibits β1 integrin mediated adhesion. The agent can be, for example, a peptide, such as HYD1, or a fragment, variant, or analog thereof. Also provided is a peptide that increases the efficacy of chemotherapy, wherein the peptide consists essentially of the HYD1 peptide, or a fragment, variant, or analog thereof.

The present inventors propose that the bone marrow microenvironment, which is characteristically rich in extracellular matrices provides a sanctuary for hematopoietic tumors to evade cell death induced by chemotherapy. Importantly, the inventors have obtained data showing that inhibiting β1 integrin binding with the addition of an inhibitory peptide (HYD1) enhances melphalan induced apoptosis in multiple myeloma cell lines. The enhancement of melphalan induced cell death caused by HYD1 treatment is most dramatic when myeloma cells are allowed direct contact with the bone marrow stroma cell line HS-5. β1 integrin inhibitory peptides represent good candidates for clinical development.

Additionally, small molecules that compete for peptide binding and are shown to be mechanistically similar to the β1 integrin inhibitory peptides will prove very useful for future clinical development as well.

HYD1 is a peptide that inhibits β1 integrin-mediated adhesion. Recently, the inventors demonstrated that HYD1 potentiates melphalan-induced cell death. Allowing direct contact between tumor cells and the bone marrow stroma cell line HS-5 is sufficient to confer a multi-drug resistant phenotype. The inventors have demonstrated that HYD1 potentiates melphalan induced cell death in multiple myeloma cell lines that are co-cultured with the HS-5 cell line.

Sroka T. C. et al., *Cancer Biology & Therapy*, 5(11), e1-e7, November 2006, is incorporated herein by reference in its entirety, including any figures, tables, nucleic acid sequences, amino acid sequences (e.g., peptides), and drawings.

One aspect of the subject invention provides methods for using the peptides of the invention as inhibitors of β1 integrin mediated adhesion and/or as anti-proliferative agents. Thus, in one embodiment, the method of the invention comprises administering a peptide of the invention to cells in vitro or in vivo in an amount sufficient to achieve the desired result, e.g., reduction of β1 integrin mediated adhesion. In another embodiment, the method comprises administering a peptide of the invention to a human or animal subject in an amount effective to achieve the desired therapeutic result. In one embodiment, more than one peptide of the invention is administered to the cells in vitro or in vivo. In a preferred embodiment, the HYD1 peptide, or a functional fragment or variant thereof, is administered.

In another aspect, the invention pertains to a composition referred to herein as an "adhesion trap" comprising a substrate (also referred to herein as a surface or support) with a HYD1 peptide, or fragment or variant thereof, immobilized to the surface; and a method of removing circulating tumor cells (CTC) from blood by contacting a subject's blood with the immobilized peptide, wherein the immobilized peptide binds CTC present (referred to herein as "adhesion trapping"). Binding of CTC by the immobilized peptide can occur in vitro (including ex vivo) or in vivo (e.g., wherein the adhesion trap is part of an implant or in-dwelling device). Preferably, the binding of CTC occur in vitro and the blood containing a reduced number of CTC (preferably, no CTC) is then returned (recycled) to the patient (similar to a dialysis procedure; machines similar to dialysis machines can be utilized). Optionally, the peptide is labeled with a detectable moiety such that binding of CTC by the peptides will be readily detectable.

Another aspect of the invention concerns a method of identifying modulators of peptide binding (a screen for molecules that displace peptide binding). Agents that are identified as being capable of competing with the HYD1 peptides of the invention for binding to β1 integrin may have utility as cytotoxic agents for research or therapy (e.g., for cancer treatment). The method comprising providing a candidate agent (such as a chemical compound, antibody, nucleic acid, or peptide); and determining whether the agent inhibits (e.g., disrupts, prevents, or interferes with), the ability of a HYD1 peptide of the invention (HYD1 or a fragment or variant thereof) to bind to β1 integrin on a cell surface (e.g., cancer cell surface) and/or inhibit β1 integrin mediated adhesion, in vitro or in vivo (e.g., in an animal model). Preferably, the cell is a cancer cell such as a myeloma cell or a cell of other cancer types (see, for example Table 1). Preferably, the peptide is labeled with a detectable moiety (e.g., a fluorescent tag, such as SAM) to facilitate the determining step. Examples of controls that may be utilized in carrying out the screening method include, but are not limited to, unlabeled HYD1 peptides (HYD1, or a fragment or variant thereof); scrambled peptides (such as HYD1S); β1 integrin blocking antibody; and non-specific surface antigen binding antibody (such as CD138 for myeloma cells). Advantageously, using the screening assay, labeled HYD1 or fragments or variants thereof, can be used to screen candidates such as small molecules, on natural product libraries, in a rapid, high-throughput fashion. Confocal microscopy has shown that FAM-HYD1 binds to the cell surface. Furthermore, this binding can be blocked by a β1 integrin blocking antibody. Fluorescence polarization (FP) analysis can be used to screen small molecule or natural product libraries for discovery of novel compounds that mimic the specific binding and potentially the biological activity of HYD1. The FP assay is based on the extent of depolarization of the free versus bond peptide, which can be accurately measured on commercially available FP plate readers. Briefly, FP analysis is based on the fact that if a small fluorescent molecule binds to a much greater sized receptor the ability of the probe to depolarize is significantly reduced. In summary, a high throughput screen (HTS) can be used to bind small molecules prior to the addition of an HYD1 probe and molecules of interest can be identified by displacement of bond peptide, with a corresponding increase in unbound peptide by FP analysis. An analogous high-throughput binding assay based on fluorescence polarization, which allows screening for small molecules that bind to the STAT3 SH2 domain, is described in Schust J. and Berg T., *Anal Biochem.*, 2004 Jul. 1; 330(1):114-8. In contrast to the assay of the invention, which is based on the binding of labeled HYD1 peptides to β1 integrin, the basis of this assay is the binding of a fluorescein-labeled phosphotyrosine-peptide derived from the interleukin-6 receptor subunit gp130 to unphosphorylated STAT3; however, the assays' operations are similar.

In another aspect, the invention concerns a screening method for detecting circulating tumor cells (CTC). Thus, the invention includes an in vitro screening assay for detecting CTC in a biological sample from a subject (such as peripheral blood), comprising obtaining a biological sample from a subject; and determining whether the peptide of the invention binds to cells (β1 integrin on the cell surface), such as circulating prostate, breast, pancreas, and lung cancer cells. Preferably, the peptide is labeled with a detectable moiety (e.g., a fluorescent tag, such as SAM) to facilitate the determining step. The determining can be carried out by contacting the peptides of the invention with the cells of the sample. For example, if the sample is blood, the blood can be placed in a heparinized tube (to prevent clotting). Any preparatory or purification/enrichment steps to facilitate the determining step will be appreciated by those of ordinary skill in the art. For example, red blood cells can be lysed, and nucleated cells can be centrifuged into a pellet. Examples of controls that may be utilized in carrying out the screening method include, but are not limited to, unlabeled HYD1 peptides (HYD1, or a fragment or variant thereof); scrambled peptides (such as HYD1S); β1 integrin blocking antibody; and non-specific surface antigen binding antibody (such as CD138 for myeloma cells). The peptide binding can be carried out using flow cytometry analysis or in tandem with CTC detection machines, for example. Optionally, the peptides may be immobilized on a surface or in suspension. Preferably, one or more additional tests are carried out before, during, or after the determining step in order to confirm that the CTC are indeed cancer cells. In another embodiment, the peptides of the invention can be tested for potency by determining their ability to prevent or interfere with the binding of labeled ligand to target cells. In this case, the ligand is labeled and incubated in the presence of the test cells and unlabelled peptides. This screening test of the invention can be used to evaluate how well a patient (e.g., a cancer patient) is responding, or will respond, to a particular therapy (e.g., tumor susceptibility to a given therapy). A discussion of the relevance and diagnostic value of CTC in cancer and methods for retrieval and testing of CTC for various markers is provided in Cristofanilli M. and Mendelsohn J., *PNAS USA,* 2006, 103 (46):1703-1704; Smerage J. B. and Hayes, D. F. et al., *British Journal of Cancer,* 2006, 94:8-12; Mesker W. E. et al., *Cellular Oncology,* 2006, 28(4):141-150; and Muller, V. et al., *Clin. Cancer Res.,* 2005, 11(10):3678-3685. The screening method of the invention tests for peptide binding but other markers, such as those described in the aforementioned publications, may be tested for as well.

Another aspect of the invention concerns an in vitro screening test for the presence of malignant cells in a mammalian tissue, the test including: obtaining a biological sample containing viable cells of the tissue from a subject; culturing the sample under conditions promoting growth of the viable cells contained therein; treating the cultured sample with a peptide of the invention; and analyzing the treated sample by a method effective to determine percent apoptosis of cells as an indicator of presence of malignant cells in the sample. This screening test of the invention can be used to evaluate how well a patient (e.g., a cancer patient) is responding, or will respond, to a particular therapy (such as therapy with the HYD1 peptides of the invention).

Optionally, the screening methods further comprise verifying that the subject is suffering from a cancer detected (e.g., by assessing for the presence of one or more cancer symptoms, detecting additional cancer markers, detecting the presence of the cancer through an imaging modality such as X-ray, CT, nuclear imaging (PET and SPECT), ultrasound, MRI) and/or treating the subject for the cancer detected (e.g., by surgery, chemotherapy, and/or radiation).

Examples of detectable moieties usable as labels include, but are not limited to, the following radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags).

The screening assays and adhesion trapping method described above can be carried out on a solid support. The solid supports used may be those which are conventional for the purpose of assaying an analyte in a biological sample, and are typically constructed of materials such as cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. The support comprising immobilized peptide can be brought into contact with a sample in vivo or in vitro (ex vivo). When, according to an embodiment of the invention, the immobilized peptide is to be contacted with a sample without removing the sample from the body (i.e., in vivo), the support should be one which is harmless to the subject and may be in any form convenient for insertion into an appropriate part of the body. For example, the support may be a probe made of polytetrafluoroethylene, polystyrene or other rigid non-harmful plastic material and having a size and shape to enable it to be introduced into a subject. The selection of an appropriate inert support is within the competence of those skilled in the art, as are its dimensions for the intended purpose.

Further examples of substrate materials include agarose, dextran, Sepharose, liposomes, carboxymethyl cellulose polystyrene, filter paper, ion-exchange resin, plastic film, plastic tube, glass beads, polyamine-methyl vinyl ether-maleic acid copolymer, amino acid copolymer, ethylene-maleic acid copolymer, nylon, silk, etc. The substrate may be in the shape of, for example, a tube, test plate, well, beads, disc, sphere, etc. Methods for immobilizing peptides to supports can be utilized. For example, linkers disclosed herein as well as other linkers known in the art can be utilized to immobilize the HYD1 peptides of the invention (HYD1, and functional fragments and variants thereof), for example at the C or N-terminus, to the support.

A contacting step in the screening assays and adhesion trap of the invention can involve contacting, combining, or mixing the sample and the suspended or immobilized peptide such as a reaction vessel, microvessel, tube, microtube, well, multi-well plate, or other solid support. In an embodiment of the invention, the solid support to be contacted with the sample has an absorbent pad or membrane for lateral flow of the liquid medium to be assayed, such as those available from Millipore Corp. (Bedford, Mass.), including but not limited to Hi-Flow Plus™ membranes and membrane cards, and SureWick™ pad materials.

Diagnostic devices useful in carrying out the methods of the invention can be constructed in any form adapted for the intended use. Thus, in one embodiment, the device of the invention can be constructed as a disposable or reusable test strip or stick to be contacted with a biological sample blood for which binding of peptides to cells is to be determined. In another embodiment, the device can be constructed using art recognized micro-scale manufacturing techniques to produce needle-like embodiments capable of being implanted or injected into an anatomical site, for indwelling diagnostic applications. In other embodiments, devices intended for repeated laboratory use can be constructed in the form of an elongated probe. In preferred embodiments, the devices of the invention comprise a solid support (such as a strip or dipstick), with a surface that functions as a lateral flow matrix defining a flow path for a biological sample such as urine, whole blood, serum, plasma, peritoneal fluid, or ascites.

The screening assays and adhesion trap method described herein can be carried out in a rapid, high-throughput fashion. In one embodiment, the assay/method is automated. In the screening assays and adhesion trap method described herein, HYD1, and fragments and variants thereof, may be arrayed on the solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or "physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or -1536 well, plates (or trays). Optionally, in addition to HYD1 peptides, other binding agents may be immobilized on the solid support.

Binding and/or detection of cancer cells such CTC, and other assays that are to be carried out on samples, can be carried out simultaneously or sequentially with the binding and/or detection of other target molecules, and may be carried out in an automated fashion, in a high-throughput format.

Throughout the application, the terms "HYD1" and "HYD-1" are used interchangeably, referring to the same peptide, KIKMVISWKG (SEQ ID NO:1), preferably comprising all D-amino acids (kikmviswkg). Throughout the application, the terms "HYDS" and "HYD1S" are used interchangeably, referring to the same "scrambled" peptide of D-amino acids, wiksmkivkg (SEQ ID NO:44), i.e., scrambled sequence of HYD1, used herein as a control.

As used herein, the terms "treatment" and "treating", and grammatical variations thereof, include therapy and prophylaxis. When used as a therapy, the compounds of the invention, by themselves or in conjunction with other agents, alleviate or reduce one or more symptoms associated with a proliferation disorder (e.g., cancer). Thus, the treatment methods may or may not be curative in nature. When used as a prophylactic treatment, the compounds of the invention, by themselves or in conjunction with other agents, delay the onset of (and may prevent) one or more symptoms associated with a proliferation disorder (e.g., cancer), or may prevent the genesis of the condition.

In one aspect, the method of the invention is a method for treating a proliferation disorder, such as cancer, comprising administering an effective amount of a peptide of the invention to a subject in need thereof.

In another aspect, the method of the invention is a method for inhibiting the growth of cancer cells in vitro or in vivo, comprising administering an effective amount of a peptide of the invention to the cancer cells.

In another aspect, the subject invention provides pharmaceutical compositions comprising at least one isolated peptide of the invention, or a polynucleotide encoding the peptide; and a pharmaceutically acceptable carrier. In one embodiment, the pharmaceutical composition comprises host cells that have been genetically modified to express the polynucleotide encoding the peptide.

By inhibiting the growth of cells proliferating in an aberrant manner, the methods, peptides, and compositions of the present invention can be used to treat a number of cell proliferation disorders, such as cancers, including, but not limited to, leukemias and lymphomas, such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as lung cancer, colon and rectum cancer, breast cancer, prostate cancer, urinary cancers, uterine cancers, bladder cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The methods of the subject invention can be carried out in vivo or in vitro, to inhibit the growth of cells (e.g., cancer cells) in humans and non-human mammals. Treatment for a proliferation disorder can proceed by the peptide's anti-proliferative activity such as pro-apoptotic activity, or by other mechanisms. In one embodiment, the proliferation disorder is one on which the peptide(s) acts by binding to β1 integrin, and/or inhibits β1 integrin signaling, and/or β1 integrin mediated adhesion.

Peptides of the invention having the capability to modulate (e.g., reduce or eliminate) β1 integrin signaling in vitro and/or in vivo, or to inhibit the growth of cancer cells in vitro and/or in vivo by inhibition of β1 integrin signaling or a different mechanism, would be considered to have the desired biological activity in accordance with the subject invention. For therapeutic applications, without being bound by theory, peptides of the subject invention can have the capability to inhibit β1 integrin signaling or β1 integrin mediated adhesion, or to inhibit the growth of cancer cells in vitro and/or in vivo by inhibition of β1 integrin signaling or β1 integrin mediated adhesion or a different mechanism. Treatment for a proliferation disorder can proceed by the peptide's anti-proliferative activity such as pro-apoptotic activity, regardless of underlying mechanism.

In one embodiment, the proliferation disorder to be treated is a cancer producing a tumor characterized by β1 integrin signaling or β1 integrin mediated adhesion. Examples of susceptible cancer types include, but are not limited to, cancer of the breast, pancreas, prostate, melanoma, myeloma, and lung. In another embodiment, the proliferation disorder to be treated is a cancer producing a tumor characterized by the CAM-DR phenotype.

In one embodiment, the proliferation disorder to be treated is characterized by a proliferation of T-cells such as autoimmune disease, e.g., type 1 diabetes, lupus and multiple sclerosis, and pathological states such as graft rejection induced by the presentation of a foreign antigen such as a graft in response to a disease condition (e.g., kidney failure). Other non-malignant diseases characterized by proliferation of cells include cirrhosis of the liver and restenosis.

The methods of the present invention can be advantageously combined with at least one additional treatment method, including but not limited to, chemotherapy, radiation therapy, or any other therapy known to those of skill in the art for the treatment and management of proliferation disorders such as cancer.

While peptides of the invention can be administered to cells in vitro and in vivo as isolated agents, it is preferred to administer these peptides as part of a pharmaceutical composition. The subject invention thus further provides compositions comprising a peptide of the invention in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The peptides of the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pa., Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "analogs" refers to compounds which are substantially the same as another compound but which may have been modified by, for example, adding side groups, oxidation or reduction of the parent structure. Analogs of the HYD1 peptide, and other peptides disclosed herein, can be readily prepared using commonly known standard reactions. These standard reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.*, 1997, 7:1623-1628; Honda, T. et al. *Bioorg. Med. Chem. Lett.*, 1998, 8:2711-2714; Konoike, T. et al. *J. Org. Chem.*, 1997, 62:960-966; Honda, T. et al. *J. Med. Chem.*, 2000, 43:4233-4246; each of which are hereby incorporated herein by reference in their entirety). Analogs, fragments, and variants of the HYD1 peptide exhibiting the desired biological activity (such as induction of apoptosis, cytotoxicity, cytostaticity, induction of cell cycle arrest, etc.) can be identified or confirmed using cellular assays or other in vitro or in vivo assays. For example, assays that detect β1 integrin signaling, β1 integrin mediated adhesion, ERK activation, $G_2$/M cell cycle arrest, and/or reduction of tumor growth may be utilized. Examples of assays to assess β1 integrin signaling, β1 integrin adhesion, and ERK activation are described in Gilcrease, M. S., *Cancer Letters*, 2007, 247(1):1-25; Larsen M. et al., *Current Opinion in Cell Biology*, 2006, 18(5):463-471; Luo B. H. and T. A. Springer, *Current Opinion in Cell Biology*, 2006, 18(5):579-586.

The peptides of the invention are useful for various non-therapeutic and therapeutic purposes. The peptides may be used for reducing aberrant cell growth in animals and humans. Because of such anti-proliferative properties of the peptides, they are useful in reducing unwanted cell growth in a wide variety of settings including in vitro and in vivo. In addition to their use in treatment methods, the peptides of the invention are useful as agents for investigating the role of β1 integrin signaling and/or β1 integrin mediated adhesion in cellular metabolism, and controlling β1 integrin mediated malignant or non-malignant cell growth in vitro or in vivo. They are also useful as standards and for teaching demonstrations.

Therapeutic application of the peptides and compositions comprising them can be accomplished by any suitable therapeutic method and technique presently or prospectively known to those skilled in the art. Further, the peptides of the invention can be used as starting materials or intermediates for the preparation of other useful compounds and compositions.

Peptides of the invention may be locally administered at one or more anatomical sites, such as sites of unwanted cell growth (such as a tumor site, e.g., injected or topically applied to the tumor), optionally in combination with a pharmaceutically acceptable carrier such as an inert diluent. Peptides of the invention may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the peptides may be incorporated into sustained-release preparations and devices.

The active agent (peptides of the invention) may also be administered intravenously or intraperitoneally by infusion or injection. Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating the peptides of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the peptides may be applied in pure-form, i.e., when they are liquids. However, it will generally be desirable to administer them topically to the skin as compositions, in combination with a dermatologically acceptable carrier, which may be a solid or a liquid.

The peptides of the subject invention can be applied topically to a subject's skin to reduce the size (and may include complete removal) of malignant or benign growths. The peptides of the invention can be applied directly to the growth. Preferably, the peptide is applied to the growth in a formulation such as an ointment, cream, lotion, solution, tincture, or the like. Drug delivery systems for delivery of pharmacological substances to dermal lesions can also be used, such as that described in U.S. Pat. No. 5,167,649 (Zook).

Useful solid carriers include finely divided solids such as talc, clay, microcrystalline cellulose, silica, alumina and the like. Useful liquid carriers include water, alcohols or glycols or water-alcohol/glycol blends, in which the peptide can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the peptides to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising a peptide of the invention (or encoding polynucleotide operably linked with a promoter for expression) in combination with a pharmaceutically acceptable carrier. Pharmaceutical compositions adapted for oral, topical or parenteral administration, comprising an amount of a compound of the invention constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Depending upon the disorder or disease condition to be treated, a suitable dose(s) may be that amount that will reduce proliferation or growth of the target cell(s), or induce cell death. In the context of cancer, a suitable dose(s) is that which will result in a concentration of the active agent (the compound of the invention) in cancer tissue, such as a malignant tumor, which is known to achieve the desired response. The preferred dosage is the amount which results in maximum inhibition of cancer cell growth, without unmanageable side effects. Administration of a peptide (or encoding polynucleotide) of the invention can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds of the invention based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

Patients in need of treatment using the methods of the present invention can be identified using standard techniques known to those in the medical or veterinary professions, as appropriate.

As used herein, the terms "cancer" and "cancerous" refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may potentially be treated using the peptides of the present invention are also listed in Table 1.

TABLE 1

Examples of Cancer Types

Acute Lymphoblastic Leukemia, Adult
Acute Lymphoblastic Leukemia, Childhood
Acute Myeloid Leukemia, Adult
Acute Myeloid Leukemia, Childhood
Adrenocortical Carcinoma
Adrenocortical Carcinoma, Childhood
AIDS-Related Cancers
AIDS-Related Lymphoma
Anal Cancer
Astrocytoma, Childhood Cerebellar
Astrocytoma, Childhood Cerebral
Basal Cell Carcinoma
Bile Duct Cancer, Extrahepatic
Bladder Cancer
Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome TABLE 1-continued Examples of Cancer Types Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Unusual Cancers of Childhood
Ureter and Renal Pelvis, Transitional Cell Cancer
Urethral Cancer
Uterine Cancer, Endometrial
Uterine Sarcoma
Vaginal Cancer
Visual Pathway and Hypothalamic Glioma, Childhood
Vulvar Cancer
Waldenström's Macroglobulinemia
Wilms' Tumor
Hairy Cell Leukemia
Head and Neck Cancer
Hepatocellular (Liver) Cancer, Adult (Primary)
Hepatocellular (Liver) Cancer, Childhood (Primary)
Hodgkin's Lymphoma, Adult
Hodgkin's Lymphoma, Childhood
Hodgkin's Lymphoma During Pregnancy
Hypopharyngeal Cancer
Hypothalamic and Visual Pathway Glioma, Childhood
Intraocular Melanoma
Islet Cell Carcinoma (Endocrine Pancreas)
Kaposi's Sarcoma
Kidney (Renal Cell) Cancer
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell

TABLE 1-continued

Examples of Cancer Types

Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. The treatment methods of the invention can be utilized for early, middle, or late stage disease, and acute or chronic disease. In some embodiments, the tumor is characterized as one exhibiting the CAM-DR phenotype.

According to the method of the subject invention, a peptide of the invention can be administered to a patient by itself, or co-administered with one or more other agents such as another compound of the invention, or a different agent or agents. Co-administration can be carried out simultaneously (in the same or separate formulations) or consecutively. Furthermore, according to the method of the subject invention, peptides of the invention can be administered to a patient as adjuvant therapy. For example, peptides of the invention can be administered to a patient in conjunction with chemotherapy.

Thus, the peptides of the invention, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the compounds of the invention, or act towards preventing any potential side effects which may be posed as a result of administration of the compounds. The peptides of the subject invention can be conjugated to a therapeutic agent, as well.

Additional agents that can be co-administered to target cells in vitro or in vivo, such as in a patient, in the same or as a separate formulation, include those that modify a given biological response, such as immunomodulators. For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more agents selected from the group consisting of anti-cancer agents, cytotoxic agents, chemotherapeutic agents, anti-signaling agents, and anti-angiogenic agents.

Peptides as described herein may comprise residues of L-amino acids, D-amino acids, or any combination thereof. In one embodiment, all amino acids of the peptide are D-amino acids. Amino acids may be from natural or non-natural sources, provided that at least one amino group and at least one carboxyl group are present in the molecule. The 20 L-amino acids commonly found in proteins are identified herein by the conventional one-letter abbreviations known in the art, and the corresponding D-amino acids are generally designated by a lower case one letter symbol. Peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions (e.g., methylation, benzylation, t-butylation, tosylation, alkoxycarbonylamino, and the liked). Such modifications and derivatives of a peptide sequence, and others known to those of skill in the art, are herein termed "variants". Preferred derivatives include amino acids having an N-acetyl group (such that the amino group that represents the N-terminus of the linear peptide is acetylated) and/or a C-terminal amide group (i.e., the carboxy terminus of the linear peptide is amidated). Residues other than common amino acids that may be present include, but are not limited to, penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

Functional fragments according to the subject invention can comprise a contiguous span of at least 4 consecutive amino acids of HYD1 (KIKMVISWKG; SEQ ID NO:1), or at least 4 consecutive amino acids of variants of HYD1. Peptides fragments according to the subject invention can be any integer in length from at least 4 consecutive amino acids to 1 amino acid less than a full length peptide (e.g., 1 amino acid less than the full length HYD1 peptide). Thus, in some embodiments, functional fragments may be 4, 5, 6, 7, 8, or 9 amino acids in length (e.g., a span of 4, 5, 6, 7, 8, or 9 consecutive amino acids KIKMVISWKG (SEQ ID NO:1).

Each fragment of the subject invention can also be described in terms of its N-terminal and C-terminal positions. For example, combinations of N-terminal to C-terminal fragments of 6 contiguous amino acids to 1 amino acid less than the full length peptide of are included in the present invention. Thus, a 6 consecutive amino acid fragment could occupy positions selected from the group consisting of 1-6, 2-7, 3-8, 4-9, 5-10, etc. It is noted that all ranges used to describe any embodiment of the present invention are inclusive unless specifically set forth otherwise and that fragments of a given peptide can be any integer in length, provided that the length of the peptide fragment is at least one amino acid shorter than the full-length peptide from which the fragment is derived.

Fragments, as described herein, can be obtained by cleaving the peptides of the invention with a proteolytic enzyme (such as trypsin, chymotrypsin, or collagenase) or with a chemical reagent, such as cyanogen bromide (CNBr). Alternatively, peptide fragments can be generated in a highly acidic environment, for example at pH 2.5. Such peptide fragments may be equally well prepared by chemical synthesis or using hosts transformed with an expression vector according to the invention. The transformed host cells contain a nucleic acid, allowing the expression of these fragments, under the control of appropriate elements for regulation and/or expression of the polypeptide fragments.

In certain preferred embodiments, fragments of the peptides disclosed herein retain at least one property or activity of the full-length peptide from which the fragments are derived. Thus, functional fragments of the invention may have one or more of the following properties or biological activities: 1) specifically bind to antibodies specific for the full-length peptide from which the fragment was derived (such as HYD1); 2) specifically bind β1 integrin; 3) inhibit β1 integrin mediated cell adhesion; 4) induce ERK signaling; 5) cause apoptosis in target cells (e.g., malignant cells), by one or more mechanisms of action. Examples of assays to assess β1 integrin signaling, β1 integrin adhesion, and ERK activation are described in Gilcrease, M. S., *Cancer Letters,* 2007, 247(1): 1-25; Larsen M. et al., *Current Opinion in Cell Biology,* 2006, 18(5):463-471; Luo B. H. and T. A. Springer, *Current Opinion in Cell Biology,* 2006, 18(5):579-586.

Ligands that may find use with the peptides of the present invention can include but not be limited to sugars, lectins, antigens, intercalators, chelators, biotin, digoxygenin and combinations thereof. The particular choice of a dye as a labeling agent or cell uptake facilitator may depend upon physical characteristics such as absorption maxima, emission maxima, quantum yields, chemical stability and solvent solubility. A large number of fluorescent and chemiluminescent compounds have been shown to be useful for labeling proteins and nucleic acids. Examples of compounds that may be used as the dye portion can include but not be limited to xanthene, anthracene, cyanine, porphyrin and coumarin dyes. Examples of xanthene dyes that may be coupled to the peptides of the present invention can include but not be limited to fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4',5'-dichloro-2',7'-dimethoxyfluorescein (JOE), 5-carboxy-2',4',5',7'-tetrachlorofluorescein (ZOE) rhodol, rhodamine, tetramethylrhodamine (TAMRA), 4,7-dichlorotetramethyl rhodamine (DTAMRA), rhodamine X (ROX) and Texas Red. Examples of cyanine dyes that may find use with the peptides of the present invention can include but not be limited to Cy 3, Cy 3.5, Cy 5, Cy 5.5, Cy 7 and Cy 7.5. Other dyes that may find use with the peptides of the present invention can include but not be limited to energy transfer dyes, composite dyes and other aromatic compounds that give fluorescent signals. Chemiluminescent compounds that may be used with the peptides of the present invention can include but not be limited to dioxetane and acridinium esters. It should also be understood that ligands and dyes are not mutually exclusive groups. For instance, fluorescein is a well known example of a moiety that has been used as a fluorescent label and also as an antigen for labeled antibodies.

The peptides (or fragments thereof) of the invention may be monomeric or multimeric (e.g., dimers, trimers, tetramers and higher multimers). Accordingly, the present invention relates to monomers and multimers of the peptides of the invention, their preparation, and compositions containing them. Multimeric peptides of the subject invention can be derived from the same peptide sequence ("homomultimers") or derived from different sequences disclosed herein ("heteromultimers"). A homomultimer may contain peptides having identical or different amino acid sequences; however these sequences are derived from the same original peptide (e.g., HYD1). A heteromultimer refers to a multimeric peptide containing one or more heterologous peptides (i.e., peptides of different proteins) in addition to the peptides of the invention. Thus, a heteromultimer, in the context of the subject invention can refer to a multimeric peptide that contains any combination of peptides of the invention. Alternatively, a heteromultimeric peptide may comprise any peptide of the invention fused to a peptide or other element that forms a hydrophobic, hydrophilic, ionic and/or covalent association.

Multimeric peptides, as set forth herein, may be formed by hydrophobic, hydrophilic, ionic and/or covalent associations and/or may be indirectly linked, by for example, liposome formation. Thus, in one embodiment, multimers of the invention, such as, for example, homodimers or homotrimers, are formed when peptides of the invention contact one another in solution. In another embodiment, heteromultimers of the invention, such as, for example, heterotrimers or heterotetramers, are formed when peptides of the invention contact antibodies to the peptides of the invention (including antibodies to the heterologous polypeptide sequence in a fusion protein of the invention) in solution. In other embodiments, multimers of the invention are formed by covalent associations with and/or between the peptides of the invention. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Other multimeric peptides can be formed by fusing the polypeptides of the invention to a leucine zipper or isoleucine zipper polypeptide sequence. Leucine zipper and isoleucine zipper domains are peptides that promote multimerization of the proteins in which they are found. Non-limiting examples of leucine zipper domains suitable for producing soluble multimeric proteins of the invention are those described in PCT application WO 94/10308, hereby incorporated by reference. Recombinant fusion proteins comprising a peptide of the invention fused to a polypeptide sequence that dimerizes or trimerizes in solution are expressed in suitable host cells, and the resulting soluble multimeric fusion protein is recovered from the culture supernatant using techniques known in the art.

Multimeric polypeptides can also be generated using chemical techniques known in the art. For example, peptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimeric polypeptides can be generated by introducing disulfide bonds between the cysteine residues located within the sequence of the peptides that are being used to construct the multimeric polypeptide (see, e.g., U.S. Pat. No. 5,478,925, which is herein incorporated by reference in its entirety). Further, peptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, other techniques known in the art may be applied to generate liposomes containing the peptides components desired to be contained in the multimer of the invention (see, e.g., U.S. Pat. No. 5,478,925, which is herein incorporated by reference in its entirety).

The peptides expressly provided herein, as well as the fragments thereof, may further comprise linker elements that facilitate the attachment of the fragments to other molecules, amino acids, or polypeptide sequences. The linkers can also be used to attach the peptides, or fragments thereof, to solid support matrices for use in affinity purification protocols. Non-limiting examples of "linkers" suitable for the practice of the invention include chemical linkers (such as those sold by Pierce, Rockford, Ill.), or peptides that allow for the connection combinations of polypeptides (see, for example, linkers such as those disclosed in U.S. Pat. Nos. 6,121,424, 5,843, 464, 5,750,352, and 5,990,275, hereby incorporated by reference in their entirety).

In other embodiments, the linker element can be an amino acid sequence (a peptide linker). In some embodiments, the peptide linker has one or more of the following characteristics: a) it allows for the free rotation of the peptides that it links (relative to each other); b) it is resistant or susceptible to digestion (cleavage) by proteases; and c) it does not interact with the peptides it joins together. In various embodiments, a multimeric construct according to the subject invention includes a peptide linker and the peptide linker is 5 to 60 amino acids in length. More preferably, the peptide linker is 10 to 30, amino acids in length; even more preferably, the peptide linker is 10 to 20 amino acids in length. In some embodiments, the peptide linker is 17 amino acids in length.

Multimeric constructs of the subject invention can also comprise a series of repeating elements, optionally interspersed with other elements. As would be appreciated by one skilled in the art, the order in which the repeating elements occur in the multimeric polypeptide is not critical and any arrangement of the repeating elements as set forth herein can be provided by the subject invention. Thus, a "multimeric construct" according to the subject invention can provide a multimeric polypeptide comprising a series of peptides, or peptide fragments, that are, optionally, joined together by linker elements (either chemical linker elements or amino acid linker elements).

A "variant" or "variant peptide" (or peptide variant) is to be understood to designate peptides exhibiting, in relation to the HYD1 peptide, certain modifications. These modifications can include a deletion, addition, or substitution of at least one amino acid (e.g., one, two, three or more amino acids), a truncation, an extension, a chimeric fusion (fusion protein), a mutation, or polypeptides exhibiting post-translational modifications. These modifications can occur anywhere in the peptide, e.g., one or both ends and/or in the middle. Among these homologous variant peptides, are those comprising amino acid sequences exhibiting between at least (or at least about) 20.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant peptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the peptide sequences of the instant invention. In a preferred embodiment, a variant or modified peptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to the HYD1 peptide. The percent identity is calculated with reference to the full-length polypeptide or the length of the fragment of a particular SEQ ID NO: that is identified. In all instances, variant peptides retain at least one of the biological activities associated with the HYD1 peptide (for example, the ability to: 1) specifically bind to antibodies specific for the full-length peptide from which the fragment was derived (such as HYD1); 2) specifically bind β1 integrin; 3) to inhibit β1 integrin mediated cell adhesion; 4) to induce ERK signaling; 5) cause apoptosis in target cells (e.g., malignant cells), regardless of mechanism of action (e.g., caspase-dependent and/or caspase independent)). Examples of assays to assess β1 integrin signaling, β1 integrin adhesion, and ERK activation are described in Gilcrease, M. S., *Cancer Letters*, 2007, 247(1):1-25; Larsen M. et al., *Current Opinion in Cell Biology*, 2006, 18(5):463-471; Luo B. H. and T. A. Springer, *Current Opinion in Cell Biology*, 2006, 18(5):579-586.

For example, one or more amino acid residues within the sequence can be substituted by another amino acid of a similar polarity which acts as a functional equivalent, resulting in a silent alteration. In one aspect of the present invention, conservative substitutions for an amino acid within the sequence may be selected from other members of the class to which the amino acid belongs (see Table 2). Conservative substitutions also include substitutions by amino acids having chemically modified side chains that do not eliminate the biological function of the resulting variant.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Fusion proteins according to the subject invention comprise one or more heterologous polypeptide sequences (e.g., tags that facilitate purification of the peptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli*," *J. of Experimental Biology* 203:19-28, The Co. of Biologists, Ltd., G.B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. of Chromatography A*. 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B.V.; Smith [1998] "Cookbook for Eukaryotic Protein Expression Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology*, 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

In other embodiments, peptides of the subject invention can be fused to heterologous polypeptide sequences that have adjuvant activity (a polypeptide adjuvant). Non-limiting examples of such polypeptides include heat shock proteins (hsp) (see, for example, U.S. Pat. No. 6,524,825, the disclosure of which is hereby incorporated by reference in its entirety).

Peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.*, 1963, 85:2149, which involves assembling a linear peptide chain on a resin support using protected amino acids. Solid phase peptide synthesis typically utilizes either the Boc or Fmoc strategy, which are well known in the art.

Those of ordinary skill in the art will recognize that, in solid phase synthesis, deprotection and coupling reactions must go to completion and the side-chain blocking groups must be stable throughout the synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

The peptides disclosed here in may be modified by attachment of a second molecule that confers a desired property upon the peptide, such as increased half-life in the body, for example, pegylation. Such modifications also fall within the scope of the term "variant" as used herein.

Covalent attachment of a molecule or solid support may generally be achieved by first reacting the support material with a bifunctional reagent that will also react with a functional group, such as a hydroxyl, thiol, carboxyl, ketone or amino group, on the modulating agent. A preferred method of generating a linkage is via amino groups using glutaraldehyde. A peptide may be linked to cellulose via ester linkages. Similarly, amide linkages may be suitable for linkage to other molecules such as keyhole limpet hemocyanin or other support materials.

Although peptides and other β1 integrin inhibitors as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a peptide or other β1 integrin inhibitor to facilitate targeting to one or more specific tissues. As used herein, a "targeting agent," may be any substance (such as a compound or cell) that, when linked to a peptide or other β1 integrin inhibitor, enhances the transport of the inhibitor to a target tissue, thereby increasing the local concentration of the inhibitor. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site.

For certain embodiments, it may be beneficial to also, or alternatively, link a drug to a peptide or other beta 1-integrin inhibitor. As used herein, the term "drug" refers to any bioactive agent intended for administration to a human or non-human mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more peptides or other beta 1-integrin inhibitors as described herein may be present within a pharmaceutical composition. A pharmaceutical composition comprises one or more peptides or other beta 1-integrin inhibitors in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A peptide may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

Various techniques may be utilized to facilitate delivery of the HYD1 peptides of the invention (and nucleic acids encoding them) to the target cells in vitro (including ex vivo) and in vivo (Cellular Drug Delivery: Principles and Practice, edited by Lu, D. R. and Oie, S., Human Press, Totowa, N.J., 2004). Optionally, it may be desirable to facilitate delivery of the peptides of the invention through the outer cell membrane. Various protein carrier molecules may be coupled to the peptides of the invention to assist penetration through biological membranes. For example, small regions (e.g., 9-16 amino acids) of proteins called protein transduction domains (PTDs) cell penetrating peptides (CPP) possess the ability to traverse biological membranes through protein transduction (Barnett, E. M. et al., *Invest. Opthalmol. Vis. Sci.*, 2006, 47:2589-2595; Schwarze S. R. et al., *Science*, 1999, 285(5433):1569-1572; Wadia, J. S, and Dowdy, S. F., *Advanced Drug Delivery Reviews*, 2005, 57(4): 579-596; Wadia, J. S, and Dowdy, S. F., *Curr. Opin. Biotechnol.*, 2002, 13(1)52-56; Ho A. et al., *Cancer Research*, 2001, 61:474-477; Futaki et al., *J. Biol. Chem.*, 2001, February, 276(8):5836-5840; Cao G. et al., *J. Neurosci.*, 2002, 22(13):5423-5431; Becker-Hapk, M. et al., *Methods*, 2001, 24:247-256; Snyder, E. L. and Dowdy, S. F., *Curr. Opin. Mol. Ther.*, 2001, 3:147-152; Lewin, M. et al., *Nat. Biotechnol.*, 2000, 18:410-414; Tung, C. H. et al., *Bioorg. Med. Chem.*, 2002, 10:3609-3614; Richard, J. P., et al., *J. Biol. Chem.*, Oct. 30, 2002, epub ahead of print). Transduction can occur in a receptor- and transporter-independent fashion that appears to target the lipid bilayer directly. Proteins (peptides) and compounds that are linked to PTDs (e.g., covalently) have the capability to traverse outer cell membranes. Preferably, the delivery peptide is a trans-activating transcriptional activator (TAT) peptide or an Antennapedia (ANT) peptide, or a derivative of either. PTDs can be linked to the peptides of the subject invention for transport across the cell membrane. One well characterized PTD is the human immunodeficiency virus (HIV)-1 Tat peptide (see, for example, U.S. Pat. Nos. 5,804,604; 5,747,641; 5,674,980; 5,670,617; and 5,652,122). Peptides such as the homeodomain of *Drosophila* antennapedia (ANTP) and arginine-rich peptides display similar properties can be employed. VP22, a tegument protein from Herpes simplex virus type 1 (HSV-1), also has the ability to transport proteins across a cell membrane, and may be coupled to the peptides of the invention.

Furthermore, some protein carrier molecules, such as PTDs, may be used to promote efficient delivery of genetic material to cells in vitro (including ex vivo) or in vivo (see, for example, Eguchi A. et al., *J. Biochem.*, 2001 276(28):26204-26210; Torchilin, V. P. et al., *PNAS*, 2001, 98(15):8786-9791). Such molecules can be coupled to viral and non-viral gene delivery vectors for delivery of nucleic acids encoding peptides such as those of the invention (Lehmusvaara S. et al., *BioTechniques*, 2006, 40(5):573-576). TAT-based polyplexes can also been utilized, and should be particularly beneficial in cases that require surface presentation of membrane-active or cell-specific targeting peptides (Manickam D. S. et al., *Journal of Controlled Release*, 2005, 102:293-306). Accordingly, such agents can be coupled to synthetic vectors such as liposomes for delivery of HYD1 peptides or nucleic acids encoding the peptides.

The subject invention also provides polynucleotides comprising nucleotide sequences encoding the peptides of the invention. Polynucleotides can be administered to cells or subjects and expressed in place of the peptides themselves. The subject invention also provides genetic constructs comprising a polynucleotide sequence of the invention. Genetic constructs of the subject invention can also contain additional regulatory elements such as promoters and enhancers and, optionally, selectable markers. In one embodiment, host cells that have been genetically modified with a polynucleotide encoding at least one peptide of the invention are administered to a subject to treat a proliferation disorder and/or to reduce the growth of malignant cells. The polynucleotide is expressed by the host cells, thereby producing the peptides within the subject. Preferably, the host cells are allogeneic or autogeneic to the subject.

Also within the scope of the subject instant invention are vectors or expression cassettes containing genetic constructs as set forth herein or polynucleotides encoding the peptides, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include in the 5'-3' direction of transcription, a transcriptional and translational initiation region, a DNA sequence of the invention, and a transcriptional and translational termination regions. The transcriptional initiation region, the promoter, may be native or analogous, or foreign or heterologous, to the host cell. Additionally, the promoter may be the natural sequence or alternatively a synthetic sequence. By "foreign" is intended that the transcriptional initiation region is not found in the native cell into which the transcriptional initiation region is introduced. As used herein, a chimeric gene comprises a coding sequence operably linked to a transcriptional initiation region that is heterologous to the coding sequence.

Another aspect of the invention provides vectors for the cloning and/or the expression of a polynucleotide sequence taught herein. Vectors of this invention can also comprise elements necessary to allow the expression and/or the secretion of the nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a peptide, fragment, or variant encoded by a polynucleotide sequence disclosed herein comprising the culture of a host cell transformed with a polynucleotide of the subject invention under conditions that allow for the expression of the peptide and, optionally, recovering the expressed peptide.

The disclosed polynucleotide sequences can also be regulated by a second nucleic acid sequence so that the peptide is expressed in a host transformed with the recombinant DNA molecule. For example, expression of a peptide may be controlled by any promoter/enhancer element known in the art. Promoters which may be used to control expression include, but are not limited to, the CMV-IE promoter, the SV40 early promoter region (Bernoist and Chambon, 1981, *Nature* 290: 304-310), the promoter contained in the 3' long terminal repeat of Rous sarcoma virus (Yamamoto, et al., 1980, *Cell* 22:787-797), the herpes simplex thymidine kinase promoter (Wagner et al., 1981, *Proc. Natl. Acad. Sci. U.S.A.* 78:1441-1445), the regulatory sequences of the metallothionein gene (Brinster et al., 1982, *Nature* 296:39-42); prokaryotic vectors containing promoters such as the β-lactamase promoter (Villa-Kamaroff, et al., 1978, *Proc. Natl. Acad. Sci. U.S.A.* 75:3727-3731), or the tac promoter (DeBoer, et al., 1983, *Proc. Natl. Acad. Sci. U.S.A.* 80:21-25); see also "Useful proteins from recombinant bacteria" in *Scientific American*, 1980, 242:74-94; plant expression vectors comprising the nopaline synthetase promoter region (Herrera-Estrella et al., 1983, *Nature* 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, *Nature* 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The vectors according to the invention are, for example, vectors of plasmid or viral origin. In a specific embodiment, a vector is used that comprises a promoter operably linked to a protein- or peptide-encoding nucleic acid sequence contained within the disclosed polynucleotide sequences, one or more origins of replication, and, optionally, one or more selectable markers (e.g., an antibiotic resistance gene). Expression vectors comprise regulatory sequences that control gene expression, including gene expression in a desired host cell. Exemplary vectors for the expression of the peptides of the invention include the pET-type plasmid vectors (Promega) or pBAD plasmid vectors (Invitrogen). Furthermore, the vectors according to the invention are useful for transforming host cells so as to clone or express the polynucleotide sequences of the invention. Examples of suitable viral vectors include lentivirus, adenovirus, adeno-associated virus, and pox virus.

The invention also encompasses the host cells transformed by a vector according to the invention. These cells may be obtained by introducing into host cells a nucleotide sequence inserted into a vector as defined above, and then culturing the cells under conditions allowing the replication and/or the expression of the polynucleotide sequences of the subject invention.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the peptides include, and are not limited to, those taught in U.S. Pat. Nos. 6,319,691, 6,277, 375, 5,643,570, or 5,565,335, each of which is incorporated by reference in its entirety, including all references cited within each respective patent.

Furthermore, a host cell strain may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

Methods of introducing polynucleotides into individuals for expression are well-known to the skilled artisan. For example, DNA can be injected into skeletal muscle or other somatic tissues (e.g., intramuscular injection). Cationic liposomes or biolistic devices, such as a gene gun, can be used to deliver DNA. Alternatively, iontophoresis and other means for transdermal transmission can be used for the introduction of DNA into an individual.

Viral vectors for use in the subject invention can have a portion of the viral genome that is deleted to introduce new genes without destroying infectivity of the virus. The viral vector of the present invention is, typically, a non-pathogenic virus. At the option of the practitioner, the viral vector and/or promoter can be selected so as to infect a specific cell or tissue type (e.g., tissue-specific promoters). Alternatively, a viral vector can be selected that is able to infect any cell in the individual. General strategies for construction of vaccinia virus expression vectors are known in the art (see, for example, Smith and Moss Bio Techniques November/December, 306-312, 1984; U.S. Pat. No. 4,738,846 (hereby incorporated by reference in its entirety).

Compositions comprising the subject polynucleotides can include appropriate nucleic acid vaccine vectors (plasmids), which are commercially available (e.g., Vical, San Diego, Calif.) or other nucleic acid vectors (plasmids), which are also commercially available (e.g., Valenti, Burlingame, Calif.). Alternatively, compositions comprising viral vectors and polynucleotides according to the subject invention are provided by the subject invention. In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science*, Mack Publishing Company, Easton, Pa.

EXEMPLIFIED EMBODIMENTS

The invention includes but is not limited to the following embodiments:

Embodiment 1

An isolated peptide that is a fragment or variant of KIKMVISWKG (HYD1; SEQ ID NO:1).

Embodiment 2

The isolated peptide of embodiment 1, selected from among AIAMVISWAG (SEQ ID NO:2; HYD8); AIKMVISWAG (SEQ ID NO:3; HYD6); AIKMVISWKG (SEQ ID NO:4; HYD2); AKMVISW (SEQ ID NO:5); AKMVISWKG (SEQ ID NO:6); IAMVISW (SEQ ID NO:7); IAMVISWKG (SEQ ID NO:8); IKAVISW (SEQ ID NO:9); IKAVISWKG (SEQ ID NO:10); IKMAISW (SEQ ID NO:11); IKMAISWKG (SEQ ID NO:12); IKMVASW (SEQ ID NO:13); IKMVASWKG (SEQ ID NO:14); IKMVIAW (SEQ ID NO:15); IKMVIAWKG (SEQ ID NO:16); IKMVISA (SEQ ID NO:17); IKMVISAKG (SEQ ID NO:18); IKMVISW (SEQ ID NO:19); IKMVISWAG (SEQ ID NO:20); KMVISWKA (SEQ ID NO:21); IKMVISWKG (SEQ ID NO:22; HYD18; (-K)HYD1); ISWKG (SEQ ID NO:23); KAKMVISWKG (SEQ ID NO:24); KIAMVISWAG (SEQ ID NO:25; HYD7); KIAMVISWKG (SEQ ID NO:26); KIKAVISWKG (SEQ ID NO:27); KIKMAISWKG (SEQ ID NO:28); KIKMV (SEQ ID NO:29); KIKMVASWKG (SEQ ID NO:30); KIKMVI (SEQ ID NO:31; HYD16); KIKMVIAWKG (SEQ ID NO:32); KIKMVIS (SEQ ID NO:33; HYD15); KIKMVISAKG (SEQ ID NO:34); KIKMVISW (SEQ ID NO:35; HYD14); KIKMVISWAG (SEQ ID NO:36); KIKMVISWK (SEQ ID NO:37; HYD17; HYD1(-G)); KIKMVISWKA (SEQ ID NO:38); KMVISWKG (SEQ ID NO:39; HYD9); LSWKG (SEQ ID NO:40; HYD12); MVISWKG (SEQ ID NO:41; HYD10); SWKG (SEQ ID NO:42; HYD13); VISWKG (SEQ ID NO:43; HYD11); WIKSMKIVKG (SEQ ID NO:44); KMVIXW (SEQ ID NO:46); IKMVISWXX (SEQ ID NO:48); and KMVISWXX (SEQ ID NO:49); wherein X is any amino acid.

Embodiment 3

The isolated peptide of embodiment 1 or 2, wherein the peptide is modified by the addition of biotin, cystein, or carboxyfluorescein (FAM) to the C-terminus or N-terminus of the peptide.

Embodiment 4

The isolated peptide of any of embodiments 1-3, wherein the peptide comprises at least one D-amino acid.

Embodiment 5

An isolated polynucleotide comprising a nucleic acid sequence encoding the peptide of any of embodiment 1-4.

Embodiment 6

A pharmaceutical composition comprising at least one peptide or polynucleotide according to any of embodiments 1-5; and a pharmaceutically acceptable carrier.

Embodiment 7

A vector comprising a polynucleotide according to embodiment 5.

Embodiment 8

A host cell genetically modified to express a polynucleotide according to any of embodiments 1-5.

Embodiment 9

A method of treating a proliferation disorder in a subject, comprising administering an effective amount of at least one isolated peptide, or a polynucleotide encoding the at least one peptide, to the subject, wherein the at least one peptide is the HYD1 peptide, or a functional fragment or variant thereof.

Embodiment 10

The method of embodiment 9, wherein the at least one peptide is selected from among KIKMVISWKG (HYD1; SEQ ID NO:1); AIAMVISWAG (SEQ ID NO:2; HYD8); AIKMVISWAG (SEQ ID NO:3; HYD6); AIKMVISWKG (SEQ ID NO:4; HYD2); AKMVISW (SEQ ID NO:5); AKM- VISWKG (SEQ ID NO:6); IAMVISW (SEQ ID NO:7); IAMVISWKG (SEQ ID NO:8); IKAVISW (SEQ ID NO:9); IKAVISWKG (SEQ ID NO:10); IKMAISW (SEQ ID NO:1); IKMAISWKG (SEQ ID NO:12); IKMVASW (SEQ ID NO:13); IKMVASWKG (SEQ ID NO:14); IKMVIAW (SEQ ID NO:15); IKMVIAWKG (SEQ ID NO:16); IKMVISA (SEQ ID NO:17); IKMVISAKG (SEQ ID NO:18); IKMVISW (SEQ ID NO:19); IKMVISWAG (SEQ ID NO:20); KMVISWKA (SEQ ID NO:21); IKMVISWKG (SEQ ID NO:22; HYD18; (-K)HYD1); ISWKG (SEQ ID NO:23); KAKMVISWKG (SEQ ID NO:24); KIAMVISWAG (SEQ ID NO:25; HYD7); KIAMVISWKG (SEQ ID NO:26); KIKAVISWKG (SEQ ID NO:27); KIKMAISWKG (SEQ ID NO:28); KIKMV (SEQ ID NO:29); KIKMVASWKG (SEQ ID NO:30); KIKMVI (SEQ ID NO:31; HYD16); KIKMVI-AWKG (SEQ ID NO:32); KIKMVIS (SEQ ID NO:33; HYD15); KIKMVISAKG (SEQ ID NO:34); KIKMVISW (SEQ ID NO:35; HYD14); KIKMVISWAG (SEQ ID NO:36); KIKMVISWK (SEQ ID NO:37; HYD17; HYD1(-G)); KIKMVISWKA (SEQ ID NO:38); KMVISWKG (SEQ ID NO:39; HYD9); LSWKG (SEQ ID NO:40; HYD12); MVISWKG (SEQ ID NO:41; HYD10); SWKG (SEQ ID NO:42; HYD13); VISWKG (SEQ ID NO:43; HYD11); WIKSMKIVKG (SEQ ID NO:44); KMVIXW (SEQ ID NO:46); IKMVISWXX (SEQ ID NO:48); and KMVISWXX (SEQ ID NO:49); wherein X is any amino acid.

Embodiment 11

The method of embodiment 9 or 10, wherein the at least one peptide is modified by the addition of biotin, cystein, or carboxyfluorescein (FAM) to the C-terminus or N-terminus of the peptide.

Embodiment 12

The method of any of embodiments 9-11, wherein the at least one peptide comprises at least one D-amino acid.

Embodiment 13

The method of any of embodiments 9-12, wherein the proliferation disorder is cancer.

Embodiment 14

The method of any of embodiments 9-13, wherein the at least one peptide is administered locally at the site of the proliferation disorder.

Embodiment 15

The method of any of embodiments 9-14, wherein the proliferation disorder is cancer, and wherein the at least one peptide induces cell death in circulating tumor cells.

Embodiment 16

The method of any of embodiments 9-15, wherein the proliferation disorder is cancer, and wherein the at least one peptide prevents or delays onset of metastasis to bone.

Embodiment 17

The method of any of embodiments 9-13, wherein the subject is not suffering from the proliferation disorder, and wherein the at least one peptide is administered to delay onset of the proliferation disorder.

Embodiment 18

The method of any of embodiments 9-17, wherein the subject is human.

Embodiment 19

The method of any of embodiments 9-18, wherein the proliferation disorder is a drug resistant cancer.

Embodiment 20

The method of any of embodiments 9-19, further comprising administering at least one anti-cancer agent to the subject before, during, or after said administering of the at least one peptide.

Embodiment 21

A method of suppressing the growth of, or inducing apoptosis in, malignant cells, said method comprising contacting the cells with an effective amount of at least one peptide, or polynucleotide encoding the at least one peptide, wherein the at least one peptide is the HYD1 peptide, or a functional fragment or variant thereof.

Embodiment 22

The method of embodiment 21, wherein the at least one peptide is selected from among those of embodiment 10.

Embodiment 23

The method of embodiment 21 or 22, wherein the at least one peptide is modified by the addition of biotin, cystein, or carboxyfluorescein (FAM) to the C-terminus or N-terminus of the peptide.

Embodiment 24

The method of any of embodiment 21-23, wherein the at least one peptide comprises at least one D-amino acid.

Embodiment 25

The method of any of embodiment 21-24, wherein said contacting is carried out in vitro.

Embodiment 26

The method of any of embodiments 21-24, wherein said contacting is carried out in vivo.

Embodiment 27

A method of increasing the efficacy of chemotherapy or radiation therapy in a subject, comprising administering at least one agent that binds β1 integrin or inhibits β1 integrin mediated adhesion in the subject.

Embodiment 28

The method of embodiment 27, wherein the at least one agent is an isolated HYD1 peptide (KIKMVISWKG; SEQ ID NO:1), or a functional fragment or variant thereof.

Embodiment 30

The method of embodiment 27 or 28, wherein the at least one agent is at least one peptide selected from among those of embodiment 10.

Embodiment 31

The method of any of embodiments 27-30, wherein the peptide is modified by the addition of biotin, cystein, or carboxyfluorescein (FAM) to the C-terminus or N-terminus of the peptide.

Embodiment 32

The method of any of embodiments 27-31, wherein the peptide comprises at least one D-amino acid.

Embodiment 33

A composition comprising a support and a plurality of peptides immobilized on said support, wherein the peptides comprise a HYD1 peptide (KIKMVISWKG; SEQ ID NO:1), or a functional fragment or variant thereof.

Embodiment 34

A method of removing circulating tumor cells (CTC) from blood, comprising contacting a subject's blood with a composition comprising a support and a plurality of peptides immobilized on said support, wherein the peptides comprise a HYD1 peptide (KIKMVISWKG; SEQ ID NO:1), or a functional fragment or variant thereof.

Embodiment 35

A method for identifying modulators of peptide binding, comprising providing a candidate agent; and determining whether the agent inhibits the ability of a labeled peptide to bind to β1 integrin on a cancer cell surface in vitro or in vivo, wherein the peptide is HYD1 peptide (KIKMVISWKG; SEQ ID NO:1), or a functional fragment or variant thereof.

Embodiment 36

A method for detecting circulating tumor cells (CTC), comprising obtaining a biological sample from a subject; and determining whether a labeled peptide binds to cells in the sample, wherein the peptide comprises a HYD1 peptide (KIKMVISWKG; SEQ ID NO:1), or a functional fragment or variant thereof.

Embodiment 37

An method for detecting malignant cells in a mammalian tissue, the method comprising:
  obtaining a sample containing viable cells of said tissue;
  culturing said sample under conditions promoting growth of the viable cells contained therein;
  treating the cultured sample with at least one peptide; and
  analyzing the treated sample by a method effective to determine percent apoptosis of cells as an indicator of presence of malignant cells in the sample, wherein the at least one peptide is the HYD1 peptide (KIKMVISWKG; SEQ ID NO:1), or a functional fragment or variant thereof.

DEFINITIONS

As used herein, the terms "administering" or "administer" is defined as the introduction of a substance into cells in vitro or into the body of an individual and includes oral, nasal, ocular, rectal, vaginal and parenteral routes. Compositions (e.g., peptides or polynucleotides encoding the peptides) may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN), or orally. For example, the peptides or nucleic acids can be administered by direct injection into a tumor, or systemically, into the circulatory system, to kill circulating tumor cells (CTC).

In the context of the instant invention, the terms "oligopeptide", "polypeptide", "peptide" and "protein" can be used interchangeably; however, it should be understood that the invention does not relate to the peptides in natural form, that is to say that they are not in their natural environment but that the polypeptides may have been isolated or obtained by purification from natural sources or obtained from host cells prepared by genetic manipulation (e.g., the peptides, or fragments thereof, are recombinantly produced by host cells, or by chemical synthesis). Peptides according to the instant invention may also contain non-natural amino acids, as will be described below. The terms "oligopeptide", "polypeptide", "peptide" and "protein" are also used, in the instant specification, to designate a series of residues of any length, typically L-amino acids, connected one to the other, typically by peptide bonds between the α-amino and carboxyl groups of adjacent amino acids. Linker elements can be joined to the polypeptides of the subject invention through peptide bonds or via chemical bonds (e.g., heterobifunctional chemical linker elements) as set forth below. Additionally, the terms "amino acid(s)" and "residue(s)" can be used interchangeably.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state.

As used herein, the terms "treat" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a peptide of the invention may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., proliferation disorder) prior to administration of the peptide of the invention.

As used herein, the term "(therapeutically) effective amount" refers to an amount of the compound of the invention or other agent (e.g., a drug) effective to treat a disease or disorder in a mammal. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; reduce β1 integrin signaling in the target cells, and/or relieve, to some extent, one or more of the symptoms associated with the cancer. To the extent the administered peptide prevents growth of and/or kills existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" of the compound of the invention refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells, in vitro or in vivo, unless otherwise specified.

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). In one embodiment, the anti-cancer agent administered before, during, after administration of the peptide or encoding polynucleotide of the invention is melphalen.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{86}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with the compounds of the invention are listed in Table 3. In a preferred embodiment, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 3

Examples of Chemotherapeutic Agents 13-cis-Retinoic Acid
2-Amino-6-Mercaptopurine
2-CdA
2-Chlorodeoxyadenosine
5-fluorouracil
5-FU
6-TG
6-Thioguanine
6-Mercaptopurine
6-MP
Accutane
Actinomycin-D
Adriamycin
Adrucil
Agrylin
Ala-Cort
Aldesleukin
Alemtuzumab
Alitretinoin
Alkaban-AQ
Alkeran
All-transretinoic acid
Alpha interferon
Altretamine
Amethopterin
Amifostine
Aminoglutethimide
Anagrelide
Anandron
Anastrozole
Arabinosylcytosine
Ara-C
Aranesp
Aredia
Arimidex
Aromasin
Arsenic trioxide
Asparaginase
ATRA
Avastin
BCG
BCNU
Bevacizumab
Bexarotene
Bicalutamide
BiCNU
Blenoxane
Bleomycin
Bortezomib
Busulfan
Busulfex
C225
Calcium Leucovorin
Campath
Camptosar
Camptothecin-11
Capecitabine
Carac
Carboplatin
Carmustine
Carmustine wafer
Casodex
CCNU
CDDP
CeeNU
Cerabidine
cetuximab
Chlorambucil TABLE 3-continued Examples of Chemotherapeutic Agents Cisplatin
Citrovorum Factor
Cladribine
Cortisone
Cosmegen
CPT-11
Cyclophosphamide
Cytadren
Cytarabine
Cytarabine liposomal
Cytosar-U
Cytoxan
Dacarbazine
Dactinomycin
Darbepoetin alfa
Daunomycin
Daunorubicin
Daunorubicin hydrochloride
Daunorubicin liposomal
DaunoXome
Decadron
Delta-Cortef
Deltasone
Denileukin diftitox
DepoCyt
Dexamethasone
Dexamethasone acetate
dexamethasone sodium phosphate
Dexasone
Dexrazoxane
DHAD
DIC
Diodex
Docetaxel
Doxil
Doxorubicin
Doxorubicin liposomal
Droxia
DTIC
DTIC-Dome
Duralone
Efudex
Eligard
Ellence
Eloxatin
Elspar
Emcyt
Epirubicin
Epoetin alfa
Erbitux
*Erwinia* L-asparaginase
Estramustine
Ethyol
Etopophos
Etoposide
Etoposide phosphate
Eulexin
Evista
Exemestane
Fareston
Faslodex
Femara
Filgrastim
Floxuridine
Fludara
Fludarabine
Fluoroplex
Fluorouracil
Fluorouracil (cream)
Fluoxymesterone
Flutamide
Folinic Acid
FUDR
Fulvestrant
G-CSF
Gefitinib
Gemcitabine TABLE 3-continued Examples of Chemotherapeutic Agents Gemtuzumab ozogamicin
Gemzar
Gleevec
Lupron
Lupron Depot
Matulane
Maxidex
Mechlorethamine
Mechlorethamine Hydrochlorine
Medralone
Medrol
Megace
Megestrol
Megestrol Acetate
Melphalan
Mercaptopurine
Mesna
Mesnex
Methotrexate
Methotrexate Sodium
Methylprednisolone
Mylocel
Letrozole
Neosar
Neulasta
Neumega
Neupogen
Nilandron
Nilutamide
Nitrogen Mustard
Novaldex
Novantrone
Octreotide
Octreotide acetate
Oncospar
Oncovin
Ontak
Onxal
Oprevelkin
Orapred
Orasone
Oxaliplatin
Paclitaxel
Pamidronate
Panretin
Paraplatin
Pediapred
PEG Interferon
Pegaspargase
Pegfilgrastim
PEG-INTRON
PEG-L-asparaginase
Phenylalanine Mustard
Platinol
Platinol-AQ
Prednisolone
Prednisone
Prelone
Procarbazine
PROCRIT
Proleukin
Prolifeprospan 20 with Carmustine implant
Purinethol
Raloxifene
Rheumatrex
Rituxan
Rituximab
Roveron-A (interferon alfa-2a)
Rubex
Rubidomycin hydrochloride
Sandostatin
Sandostatin LAR
Sargramostim
Solu-Cortef
Solu-Medrol
STI-571
Streptozocin

TABLE 3-continued

Examples of Chemotherapeutic Agents

Tamoxifen
Targretin
Taxol
Taxotere
Temodar
Temozolomide
Teniposide
TESPA
Thalidomide
Thalomid
TheraCys
Thioguanine
Thioguanine Tabloid
Thiophosphoamide
Thioplex
Thiotepa
TICE
Toposar
Topotecan
Toremifene
Trastuzumab
Tretinoin
Trexall
Trisenox
TSPA
VCR
Velban
Velcade
VePesid
Vesanoid
Viadur
Vinblastine
Vinblastine Sulfate
Vincasar Pfs
Vincristine
Vinorelbine
Vinorelbine tartrate
VLB
VP-16
Vumon
Xeloda
Zanosar
Zevalin
Zinecard
Zoladex
Zoledronic acid
Zometa
Gliadel wafer
Glivec
GM-CSF
Goserelin
granulocyte - colony stimulating factor
Granulocyte macrophage colony stimulating factor
Halotestin
Herceptin
Hexadrol
Hexalen
Hexamethylmelamine
HMM
Hycamtin
Hydrea
Hydrocort Acetate
Hydrocortisone
Hydrocortisone sodium phosphate
Hydrocortisone sodium succinate
Hydrocortone phosphate
Hydroxyurea
Ibritumomab
Ibritumomab Tiuxetan
Idamycin
Idarubicin
Ifex
IFN-alpha
Ifosfamide
IL - 2
IL - 11
Imatinib mesylate

TABLE 3-continued

Examples of Chemotherapeutic Agents

Imidazole Carboxamide
Interferon alfa
Interferon Alfa-2b (PEG conjugate)
Interleukin - 2
Interleukin-11
Intron A (interferon alfa-2b)
Leucovorin
Leukeran
Leukine
Leuprolide
Leurocristine
Leustatin
Liposomal Ara-C
Liquid Pred
Lomustine
L-PAM
L-Sarcolysin
Meticorten
Mitomycin
Mitomycin-C
Mitoxantrone
M-Prednisol
MTC
MTX
Mustargen
Mustine
Mutamycin
Myleran
Iressa
Irinotecan
Isotretinoin
Kidrolase
Lanacort
L-asparaginase
LCR As used herein, the term "tumor" refers to all neoplastic cell growth and proliferation, whether malignant or benign, and all pre-cancerous and cancerous cells and tissues. For example, a particular cancer may be characterized by a solid tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The peptides of the invention are capable of inducing apoptosis in tumor cells and reducing tumor cell growth. The peptides of the invention (or nucleic acids encoding them) can be administered locally at the site of a tumor (e.g., by direct injection) or remotely. The peptides of the invention can induce cell death in circulating tumor cells (CTC) in a subject, e.g., by administering the peptides or encoding nucleic acids intravenously. Furthermore, the peptides of the invention can prevent or reduce onset of metastasis to other tissues, e.g., to the bone.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

The term "vector" is used to refer to any molecule (e.g., nucleic acid, plasmid, or virus) usable to transfer coding sequence information (e.g., nucleic acid sequence encoding the HYD1 peptide or a fragment or variant thereof), such as to a host cell. A vector typically includes a replicon in which another polynucleotide segment is attached, such as to bring about the replication and/or expression of the attached segment. The term includes expression vectors, cloning vectors, and the like. Thus, the term includes gene expression vectors capable of delivery/transfer of exogenous nucleic acid sequences into a host cell. The term "expression vector" refers to a vector that is suitable for use in a host cell (e.g., a patient's cell, tissue culture cell, cells of a cell line, etc.) and contains nucleic acid sequences which direct and/or control the expression of exogenous nucleic acid sequences. Expression includes, but is not limited to, processes such as transcription, translation, and RNA splicing, if introns are present. Nucleic acid sequences can be modified according to methods known in the art to provide optimal codon usage for expression in a particular expression system. The vector may include elements to control targeting, expression and transcription of the nucleic acid sequence in a cell selective manner as is known in the art. It should be noted that often the 5'UTR and/or 3'UTR of the gene may be replaced by the 5'UTR and/or 3'UTR of the expression vehicle. The vector can include a promoter for controlling transcription of the exogenous material and can be either a constitutive or inducible promoter and/or a tissue-specific promoter, to allow selective transcription. The expression vector can also include a selection gene.

A "coding sequence" is a polynucleotide sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art (See, e.g., Sambrook et al., Molecular Cloning: A Laboratory Manual, Second Edition, 1989; DNA Cloning, Vols. I and II, D. N. Glover ed., 1985). Optionally, the polynucleotides of the present invention, and composition and methods of the invention that utilize such polynucleotides, can include non-coding sequences.

The term "operably-linked" is used herein to refer to an arrangement of flanking control sequences wherein the flanking sequences so described are configured or assembled so as to perform their usual function. Thus, a flanking control sequence operably-linked to a coding sequence may be capable of effecting the replication, transcription and/or translation of the coding sequence under conditions compatible with the control sequences. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a polypeptide will typically have its own operably-linked promoter sequence.

The terms "transfection" and "transformation" are used interchangeably herein to refer to the insertion of an exogenous polynucleotide into a host cell, irrespective of the method used for the insertion, the molecular form of the polynucleotide that is inserted, or the nature of the cell (e.g., prokaryotic or eukaryotic). The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome.

As used herein, the term "pharmaceutically acceptable salt or prodrug" is intended to describe any pharmaceutically acceptable form (such as an ester, phosphate ester, salt of an ester or a related group) of a compound of the invention, which, upon administration to a subject, provides the mature or base compound (e.g., a HYD1 peptide). Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The terms "link" or "join" refers to any method known in the art for functionally connecting peptides, including, without limitation, recombinant fusion, covalent bonding, disulfide bonding, ionic bonding, hydrogen bonding, and electrostatic bonding.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

As used in this specification, the singular forms "a", "an", and "the" include plural reference unless the context clearly dictates otherwise. Thus, for example, a reference to "a compound" includes more than one such compound. A reference to "a peptide" includes more than one such peptide, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Experimental controls are considered fundamental in experiments designed in accordance with the scientific method. It is routine in the art to use experimental controls in scientific experiments to prevent factors other than those being studied from affecting the outcome. For example, the specification and the scientific literature available to those skilled in the art at the time the application was filed describe a number of ways that one can contact a test agent (e.g., a potential ligand of β1 integrin binding) with a host cell expressing the integrin and, optionally, determine whether the test agent modulates modulates (e.g., inhibits) βintegrin mediated adhesion.

Following are examples that illustrate materials, methods, and procedures for practicing the invention. The examples are illustrative and should not be construed as limiting.

Materials and Methods

Cell Culture and Drugs. H929, 8226 and HS-5 cells were obtained from the American Type Culture Collection (Rockville, Md.). 8226 and H929 cells were grown in suspension in RPMI 1640 media (Cellgro, Fischer Scientific Pittsburgh, Pa.), supplemented with 10% fetal bovine serum (Omega Scientific, Turzana Calif.), penicillin (100 ug/ml), streptomycin (100 ug/ml) and 2 mM L-glutamine (GIBCO-BRL, Grand Island, N.Y.). For H929 cells, 0.05 mM 2-mercaptoethanol was added to the culture media. HS-5 cells were grown as a monolayer in RPMI 1640 media (Cellgro), supplemented with 10% fetal bovine serum (Omega), penicillin (100 ug/ml), streptomycin (100 ug/ml) and 2 mM L-glutamine (GIBCO-BRL, Grand Island, N.Y.). Cells were maintained at 37° C. in 5% $CO_2$/95% air atmosphere and underwent passage twice weekly.

Drugs and antibodies. Melphalan was obtained from Sigma (St. Louis, Mo.) and was dissolved in acid ethanol at 10 mg/ml. The integrin blocking antibodies included α4 blocking antibody (P4G9, Dako, Carpinteria Calif.), α5 blocking antibody (P1D6, Dako), and β1 blocking antibody (AB IIB, was provide by Dr. Doug Cress). HYD1 and HYD1S d-amino acid peptides, were synthesized by Global Peptides (Fort Collins, Colo.).

Quantification of cell adhesion to fibronectin. Briefly, 8226 or H929 myeloma cells were pre-incubated with varying concentrations of either HYD1 or the scrambled peptide (HYD1S) for 30 minutes prior to allowing cells to attach to FN for two hours. Cell adhesion was detected by crystal violet staining as previously described (Damiano J S et al. *Blood,* 1999; 93:1658-1667; Hazlehurst L A et al. *Oncogene,* 2000; 19:4319-4327).

Quantification of cell adhesion to HS-5 bone marrow stroma cells. Adhesion of 8226 or H929 cells to the HS-5 bone marrow stromal cells was performed as previously described (Nefedova Y et al. *Leukemia,* 2003; 17:1175-1182). Briefly, HS-5 cells were plated at a density of 500,000 cell/ml in a 96 well plate overnight. The following day 8226 cells, were labeled with 1 μM of the fluorescent dye CMFDA (Molecular Probes) for 30 minutes in the dark. The labeled myeloma cells were then washed three times and incubated an additional 45 minutes to allow unbound dye to diffuse out of cells. Cells were then counted and placed at a density of one million cells per ml and varying concentrations of peptide were added for 30 minutes prior to addition of 100 μl of cells to either HS-5 or BSA coated plates. Cells were allowed to adhere for two hours and unbound cells were washed with three gentle washes and total fluorescence was detected by a Victor plate reader, at 485 nm excitation and 535 nm emission. The experiment was performed in quadruplicate and repeated in 3 independent experiments.

Detection of Apoptosis. A flow cytometric assay measuring Annexin V/PI staining was used to measure apoptotic cells following 24 hours of peptide exposure as previously described (Damiano J S et al. *Blood,* 1999; 93:1658-1667). The assay was performed in triplicate and 3 independent experiments were performed. Caspase 3 and 8 activity was measured at 6 and 24 hrs post peptide treatment per manufactures' instructions (BD Biosciences, San Jose, Calif.). The caspase assays were performed in triplicate and repeated twice.

Lysosensor staining. 35 mm glass bottom microwell dishes were incubated with 10 ul Cell-tak (BD biosciences San Jose, Calif.) and 290 ul 0.5M sodium bicarbonate (Sigma) for 30 minutes. The plates were aspirated and 200,000H929 or 8226 cells were plated. Cells were then treated with either water (VC), 100 μg/ml HYD1 or 100 μg/ml HYD1S for 6 hours. After the 6-hour incubation, the plates were aspirated and washed once with warm media. Media containing 1 μM lysosensor DND-189 (Molecular Probes, Carlsbad Calif.) and 20 μM Hoechst 33342 (Molecular Probes) was added and samples were incubated for an additional 30 minutes. Samples were analyzed with a Leica DMI6000 inverted TCS SP5 confocal scanner (Leica Microsystems, Germany). 405 Diode and Argon laser lines were applied to excite the samples and tunable filters were used to minimize the crosstalk between fluorochromes. Gain, offset, and pinhole setting were identical for all samples within the treatment group. Image sections at 0.3 μM were captured with photomultiplier detectors and maximum projections were prepared with the LAS AF software version 1.6.0 build 1016 (Leica Microsystems, Germany).

Trafficking of LC3. LC3 cDNA and pK1-IRES-puro vector were kindly provided by Dr. Noboru Mizushima (Tokyo Medical and Dental University, Japan) and Dr. Gary Reuther (H. Lee Moffitt Cancer Center & Research Institute), respectively. For stable transfection of GFP-LC3 in X, a cDNA encoding GFP-LC3 was subcloned into the Xho I and EcoR I sites of the pK1-IRES-puro vector. The plasmid was then transfected into Phoenix-ampho cells using the calcium phosphate technique. The supernatant containing the recombinant retrovirus was collected 48 hr after transfection and used for infection into 8226 and H929 cells. The stable transfectants were selected with 1 μg/ml of puromycin for 4 days.

35 mm glass bottom microwell dishes were prepared as described above. The plates were aspirated and 200,000H929/LC3 or 8226/LC3 cells were plated. Cells were treated with either VC, 100 μg.ml HYD1 or 100 μg/ml HYD1S for 6 hours. After the 6 hour incubation, plates were aspirated and washed once with warm media. Media containing 20 μM Hoechst 33342 (Molecular Probes) was added to the plates and samples were incubated for 30 minutes. Samples were viewed with a Leica DMI6000 inverted microscope, TCS SP5 confocal scanner, and a 100×/1.40NA Plan Apochromat oil immersion objective (Leica Microsystems, Germany). 405 Diode and Argon laser lines were applied to excite the samples and tunable filters were used to minimize the crosstalk between fluorochromes. Gain, offset, and pinhole setting were identical for all samples within the treatment group. Image sections at 0.3 μm were captured with photomultiplier detectors and maximum projections were prepared with the LAS AF software version 1.6.0 build 1016

(Leica Microsystems, Germany). Signal intensity was measured using Pro Plus version 5.0.1.11 (Media Cybernetics Inc., Silver Spring, Md.).

Co-culture model. HS-5/GFP cells were plated at a density of 500,000 cells per ml and incubated overnight. Myeloma cells were incubated with vehicle control (water), 50 µg/ml HYD1 or 50 µg/ml HYD1S 30 minutes prior to the addition of myeloma cells (400,000 cell/ml) to either control plates or plates containing HS-5 cells. Myeloma cells were incubated with HS-5 cells for three hours prior to the addition of melphalan. Apoptotic cells were measured in GFP negative myeloma cells, by annexin PE staining and FACS analysis (n=9). ANOVO was performed to determine significance between conditions.

Electron Microscopy. H929 cells were treated for four hours with either 100 µg/ml HYD1 or HYD1S. After peptide treatment, the samples were fixed overnight in 2.5% glutaraldehyde in 0.1M phosphate buffer, pH 7.2 overnight at four degrees. Following fixation, the cells were rinsed 2 times for 10 minutes each in 0.1M phosphate buffer, pH 7.2, at 4° C. The cells were loosely pelleted in microcentrifuge tubes at 500×G for 3 minutes. The buffer was removed from the cells and replaced with 1% osmium tetroxide in the above buffer at 4° C. The cells were resuspended and post-fixed for 1 hour, then loosely pelleted and rinsed in the above buffer. This step was repeated for a total of 3 rinses of 5 minutes each, with the cells being resuspended after each buffer change. Cells were dehydrated through a graded series of acetone, 30%, 50%, 70%, and 95% acetone in water, 5 minutes per change with loose pelleting at 750×G for 5 minutes, then resuspension for each step. The cells were then dehydrated through three changes of 100% acetone, 10 minutes per change, with a 5 minute pelleting step at 1000×G, followed by resuspension in each step. The samples were then suspended in and infiltrated with a 1:1 mixture of 100% acetone:embedding medium for 1 hour while under vacuum. Following this step, the cells were pelleted at 300×G for 5 minutes, and then re-suspended in 100% embedding medium. Samples were infiltrated with 100% embedding medium for 1 hour under vacuum. Cells were then pelleted at 7800×G for 5 minutes, re-suspended in a fresh change of embedding medium, and placed back under vacuum for another hour. This step was repeated one more time. The cells were left in the last change of embedding medium until the end of the day, and then pelleted for 15 minutes at 7800×G. A fresh change of embedding medium was made without disturbing the pellets, and the medium was polymerized in a 70° C. oven for two days. Pellets were sectioned with a Reichert E ultramicrotome. Thick sections (0.5µ) were picked up and mounted on glass slides and stained with 1% toluidine blue stain. Thin sections (80-90 nm) were picked up on 100 mesh copper grids, stained with 8% aqueous uranyl acetate for 10 minutes, and Reynold's lead citrate for 5 minutes. Thin sections were examined with a Philips CM10 transmission electron microscope at 60 kV. Representative cells were photographed, and photographs printed and scanned.

SCID-Hu model. The SCID-Hu model was performed as previously described (Zhu K et al. *Blood,* 2005; 105:4759-4766). Briefly, SCID/Beige mice 4-6 weeks old were purchased from Taconic (Germantown, N.Y.). Fetal tissue (18-23 weeks) was obtained from Advance Bioscience Resource (Alameda, Calif.) in compliance with state and federal government regulations. Two bones were surgically implanted in the mammary fat pad of 6-8 week old female SCID mice. Following six weeks of bone engraftment 50,000 8226 or H929 cells were injected directly into the bone and tumor was allowed to engraft for 4 weeks. At 28 days, baseline tumor burden was quantified in the sera using either a lambda (8226) or kappa (H929) ELISA kit per manufacture instructions (Bethyl, Montgomery, Tex.) and mice were randomized into treatment groups. For HYD1 groups mice were treated with either 2 mg/kg or 8 mg/kg, (i.p.) daily as indicated. Mice receiving melphalan were given two i.p. injections of 1.5 mg/kg on day 29 and 32. Tumor burden was assessed weekly by measuring kappa or lambda levels in the sera.

Example 1

HS-5 Model of Drug Resistance

A model which perhaps more closely resembles the tumor microenvironment is one based on the response of tumor cells to chemotherapy in a bone marrow stroma model. Fortney et al, showed that co-culture of B lineage tumor cells with bone marrow stroma resulted in reduced apoptosis induced by etoposide and Ara-C. Although the exact mechanism has not been fully elucidated, the CAM-DR phenotype correlated with reduced activation of caspase 3, suggesting inhibition of the apoptotic pathway (Fortney J E, et al. *Leuk Res.* 2001; 25:901-907). In this stroma model, cytoprotection required direct cell-cell contact, as drug resistance could not be conferred by the addition of stromal cell conditioned media. The drug resistant phenotype could be reversed by an anti-VCAM-1 antibody suggesting that the VCAM-1 receptor, VLA-4 is conferring resistance in this stroma model. It is difficult to interpret studies using blocking β1 integrin on drug resistance when cells are adhered to FN as an adherent population is no longer available to test. However, cell adhesion to the bone marrow stroma cells is multifactorial thus tumor cells will remain adherent despite the addition of a β1 inhibitory peptide. In summary, in the HS-5 co-culture model, drug sensitivity can be tested for by blocking β1 integrin binding without quantitatively disrupting cell-cell contact. The HS-5 BMS cell line appears to be fibroblastoid and secrete significant levels of soluble growth factors (Roecklein B A, et al. *Blood.* 1995; 85:997). Moreover, the present inventors have data showing that co-culturing myeloma cell lines with a bone marrow stroma cell line (HS-5) confers resistance to melphalan, dexamthesone and topoisomerase II inhibitors.

Example 2

β1 Integrin Inhibitory Peptide

Several peptides that inhibited β1 integrin mediated adhesion of DU145 prostate cancer cells to fibronectin, laminin and collagen IV have been shown using combinatorial peptide libraries and a functional binding assays (DeRoock I B, et al. *Cancer Res.* 2001; 61:3308-3313). The lead candidates isolated from the functional screens were the D-amino acid peptides referred to as RZ-3 (kmviywkag) and HYD-1 (kikmviswkg). A scrambled derivative of HYD-1 referred to as HYD1S (wiksmkivkg) was shown not to inhibit cell adhesion to extracellular matrixes. The data show that HYD-1, but not the scrambled peptide, blocks cellular adhesion of myeloma cells to fibronectin. Furthermore, the data show that pretreatment with the HYD1 peptide potentiates melphalan induced apoptosis. The blocking peptides are only 10 amino acids in length and thus it is reasonable to assume that small molecules may be developed that will bind the peptide site residing on β1 integrin. In addition, by labeling the peptide (e.g., fluorescently), an efficient screen for blocking peptide binding is made available.

Example 3

Target Validation

Figure 2:
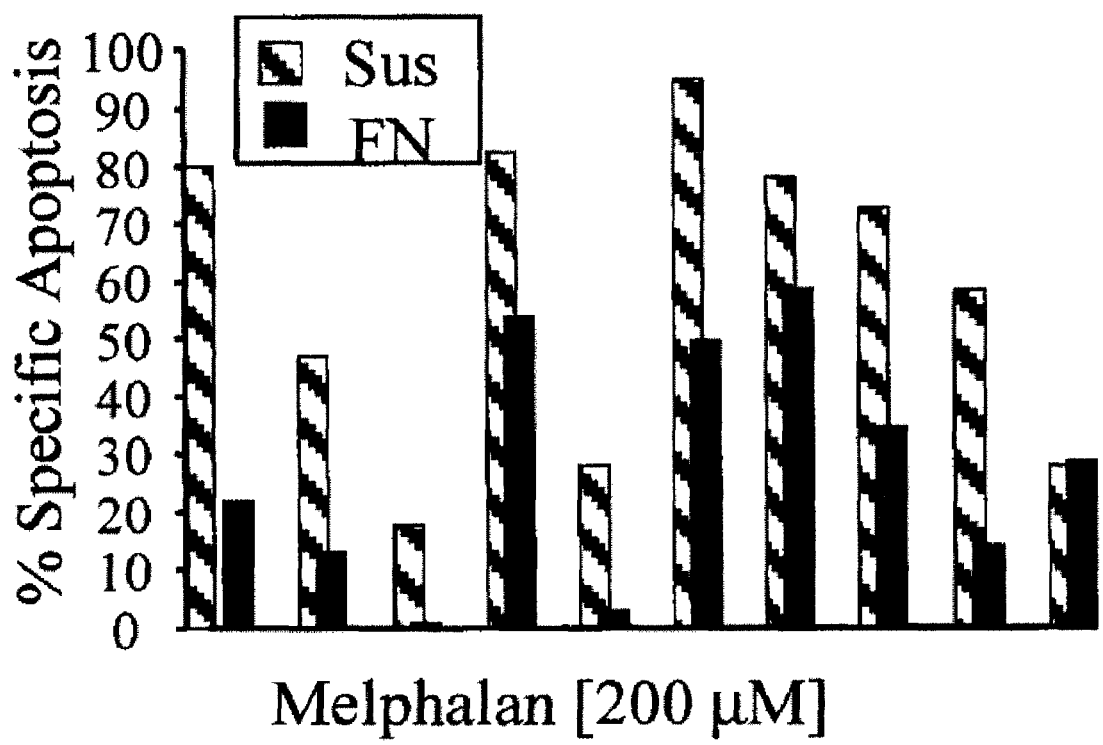
FIG. 2 is a graph showing adhesion of 9 out of 10 multiple myeloma primary patient specimens to FN confers resistance to melphalan induced cell death.

It has been reported that β1-integrin mediated adhesion of 8226 cells and K562 cells to FN blocked cell death induced by the alkylating agent melphalan (Damiano J S, et al. *Blood.* 1999; 93:1658-1667; Hazlehurst LA, et al. *Cancer Res.* 2003; 63:7900-7906). In order to determine whether the CAM-DR phenotype is a potential mechanism of clinical de novo drug resistance, melphalan-induced cell death was recently measured in primary myeloma patient specimens (See FIG. 2). Plasma cells were identified by either positive Kappa or Lambda staining, and apoptotic myeloma cells were identified by the Tunnel assay. Ten individual patients were tested and as shown in FIG. 2. 9 out of 10 patient specimens were protected from melphalan induced cell death when adherent to FN compared to suspension cultures. The mean percent apoptosis of plasma cells obtained from bone marrow aspirates and adhered to FN prior to treatment with 200 μM melphalan was 27.7% (95% LCI 17.6 and 95% UCI=32.8) compared to 55.6% (95% LCI=44.1% and UCI=67.2%) apoptosis for plasma cells treated in suspension cultures (p<0.01, Students T-test). These data further support the potential of β1 integrin as a target for increasing the efficacy of currently used cytotoxics.

Figures 3A, 3B, 3C, 3D:
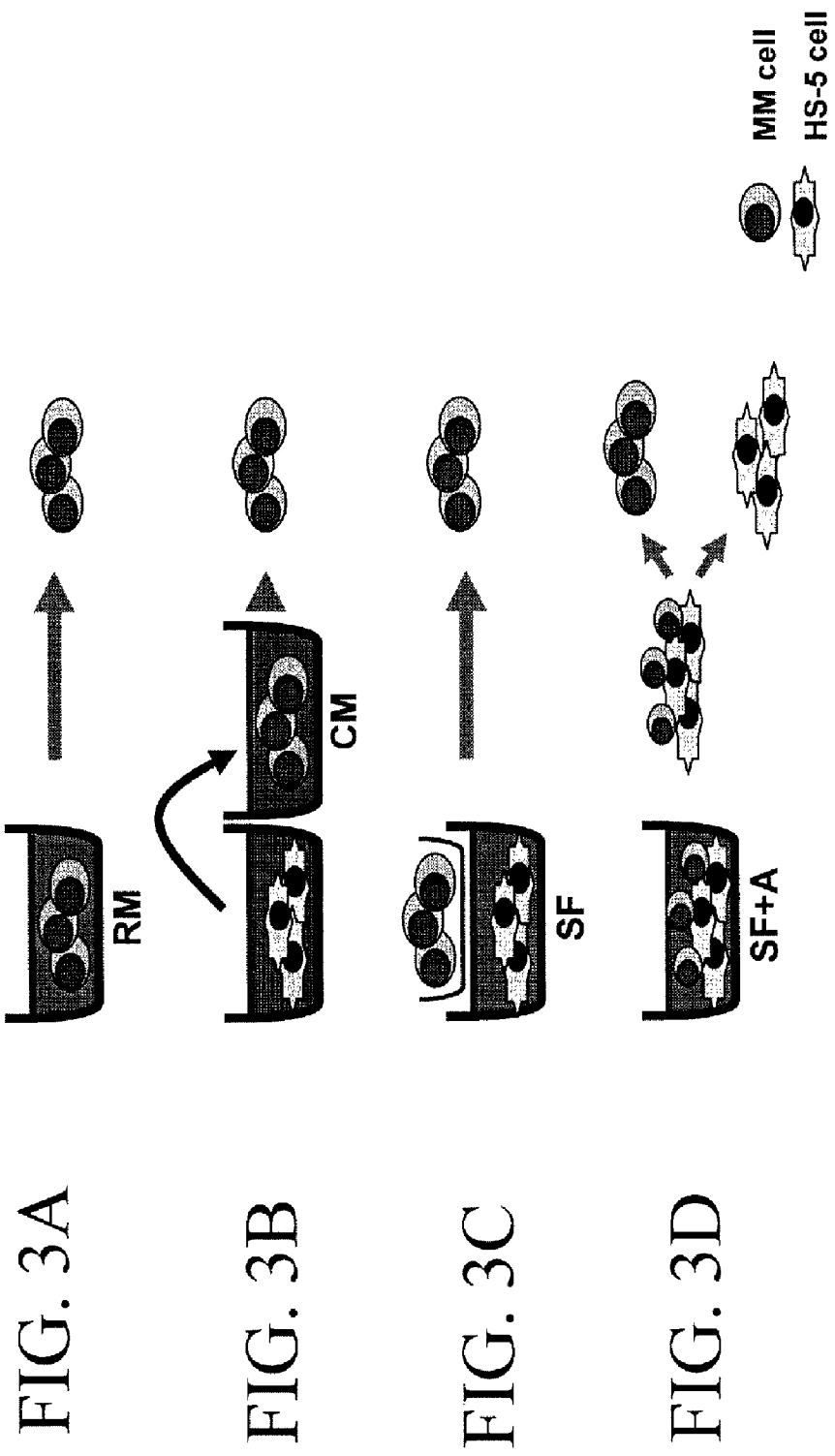
FIGS. 3A-D are a series of illustrations showing BMS models of drug resistance.
Figure 4A:
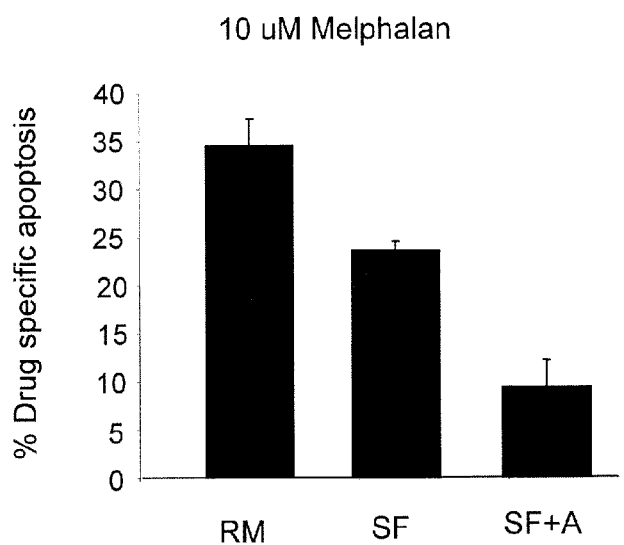
FIGS. 4A-4E are a series of graphs showing that the BMS model protects myeloma MM1.S cells from melphalan (FIG. 4A), mitoxantrone (FIG. 4B), and dexamethasone (FIGS. 4C-4E) induced cell death. SF+A model confers the highest levels of resistance to cell death induced by either mitoxantrone or melphalan. CM protects from dexamethasone but not melphalan induced apoptosis.
Figure 4B:
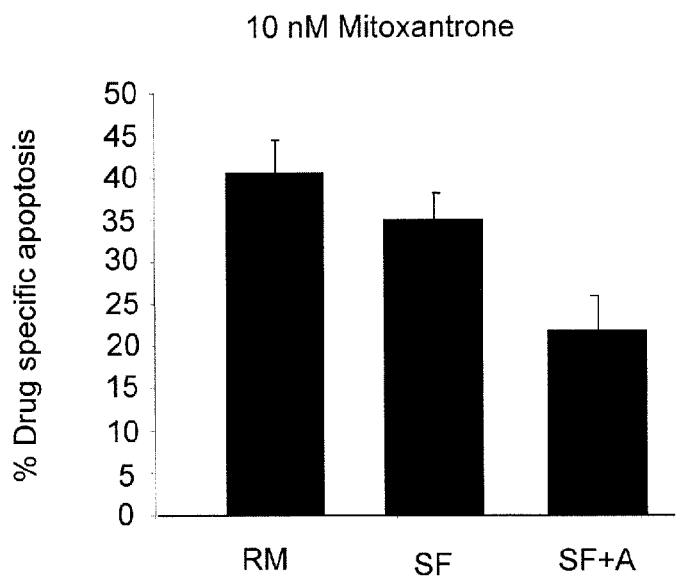
Figure 4C:
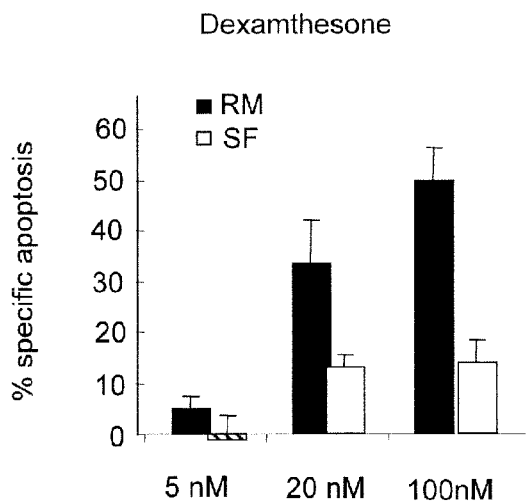
Figure 4D:
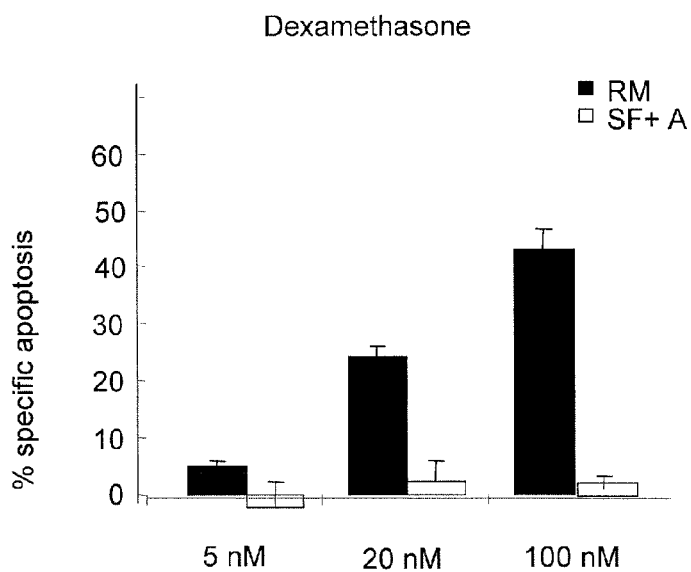
Figure 4E:
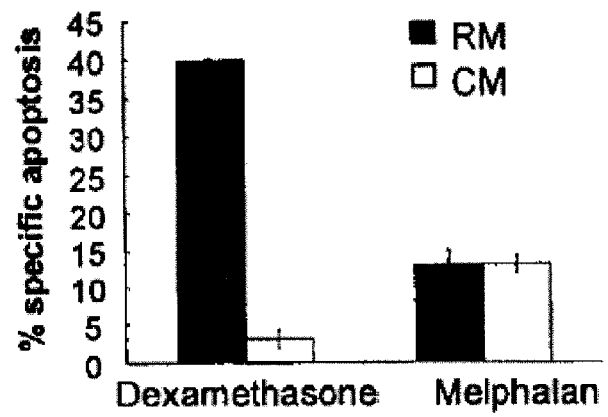

The CAM-DR phenotype is tested by removing unadhered cells before the addition of drug. Because adhesion of hematopoietic tumor cell lines to FN can be entirely blocked by either the addition of the β1 blocking antibodies or the β1 integrin inhibitory peptide, this makes it technically difficult to test for reversal of CAM-DR in the FN adhesion model. For this reason, the inventors chose to test for the reversal of drug resistance in adherent cells by using a bone marrow stroma (BMS) model (HS-5 cell line). In the BMS model of drug resistance, cell-cell adhesion is mediated by multiple adhesion moieties and thus the addition of a β1 blocking antibody is not sufficient to block tumor cell adhesion to the BMS cell line. The BMS model system is described in FIGS. 3A-D. These models have facilitated the availability of four discrete hematopoietic tumor populations. The first tumor population (FIG. 3A) is maintained in a traditional suspension culture in RPMI media containing 10% FBS (RM). Conditioned media is prepared by adding fresh RPMI media containing 10% FBS to HS-5 cells which are 75% confluent. After three hours, the media is then collected, centrifuged and stored at −70 for up to one month. This tumor cell culture condition is referred to as CM (FIG. 3B). The third tumor cell population consists of placing HS-5 cells in the bottom chamber and tumor cell in a top chamber that is separated by a membrane allowing for diffusion of soluble factors (see FIG. 3C). This condition is distinct from CM because it considers dynamic soluble interactions between the tumor cell and BMS cells (see FIG. 3D). Finally, as shown in FIG. 3D, the fourth culture condition considers both cell adhesion and soluble interactions of tumor cells and BMS cells. As shown in FIGS. 4A-E, using HS-5 cells as the stromal layer in the BMS model is sufficient to confer resistance to melphalan, mitoxantrone and dexamethasone induced cell death. Regardless of the cytotoxic agent used, the levels of drug resistance are greatest for myeloma cells which are adherent to the BMS. Finally as shown in FIG. 4E, conditioned media is sufficient to protect MM1.S cells from dexamethasone-induced apoptosis but not melphalan induced apoptosis. Thus, for DNA damaging agents, such as mitoxantrone and melphalan, soluble factors produced by the HS-5 cell line does not confer significant levels of resistance.

Example 4

β1 Inhibitory Peptide

Figure 5:
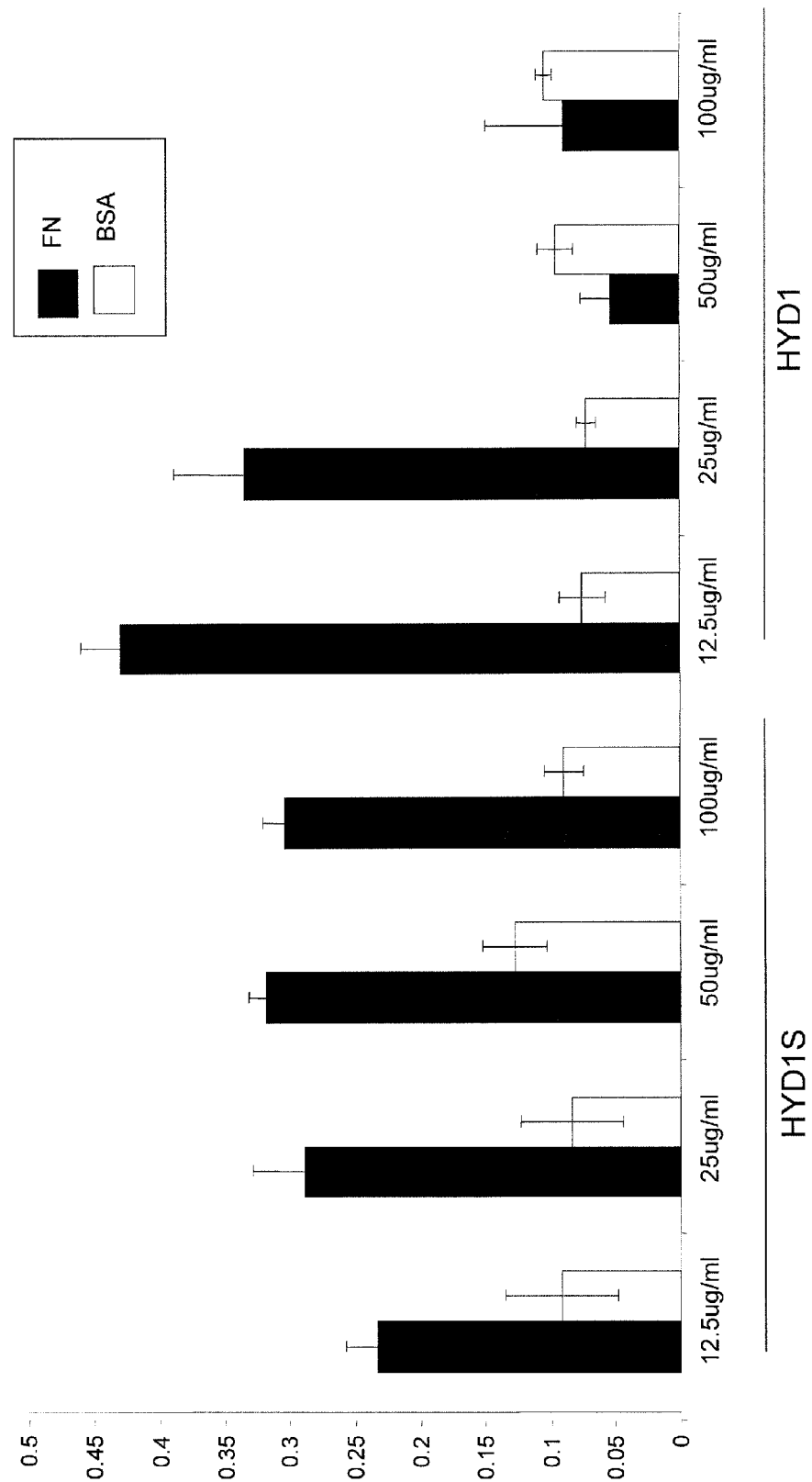
FIG. 5 is a graph showing that HYD1 but not the scrambled peptide inhibits cell adhesion of 8226 myeloma cells to FN.
Figure 6:
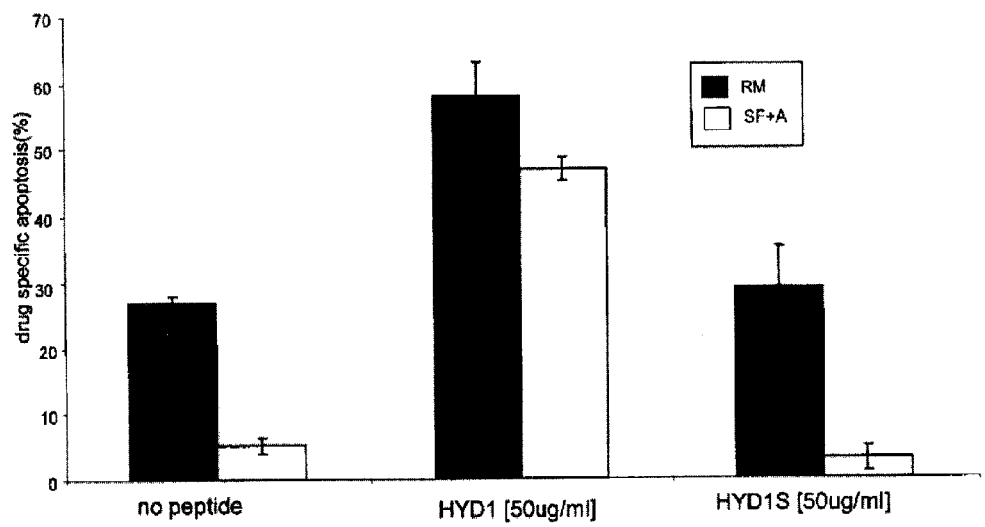
FIG. 6 is a graph showing that treatment of H929 cells with HYD1 but not the scrambled peptide (HYD1S) reverses resistance associated with co-culturing tumor cells with the BMS cell line HS-5.
Figure 7:
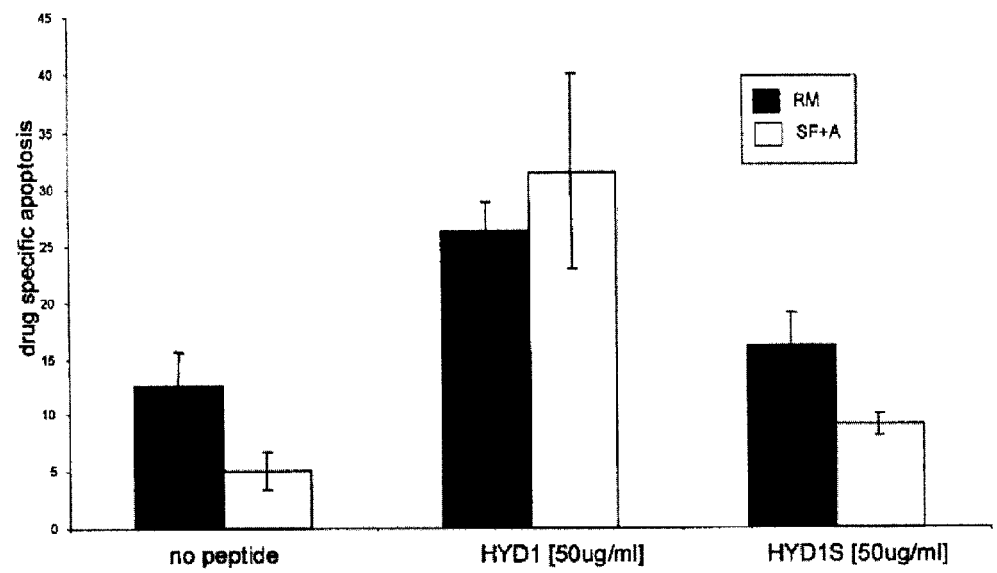
FIG. 7 is a graph showing that treatment of 8226 cells with HYD1 but not the scrambled peptide (HYD1S) reverses resistance associated with co-culturing tumor cells with the BMS cell line HS-5.
Figure 8:
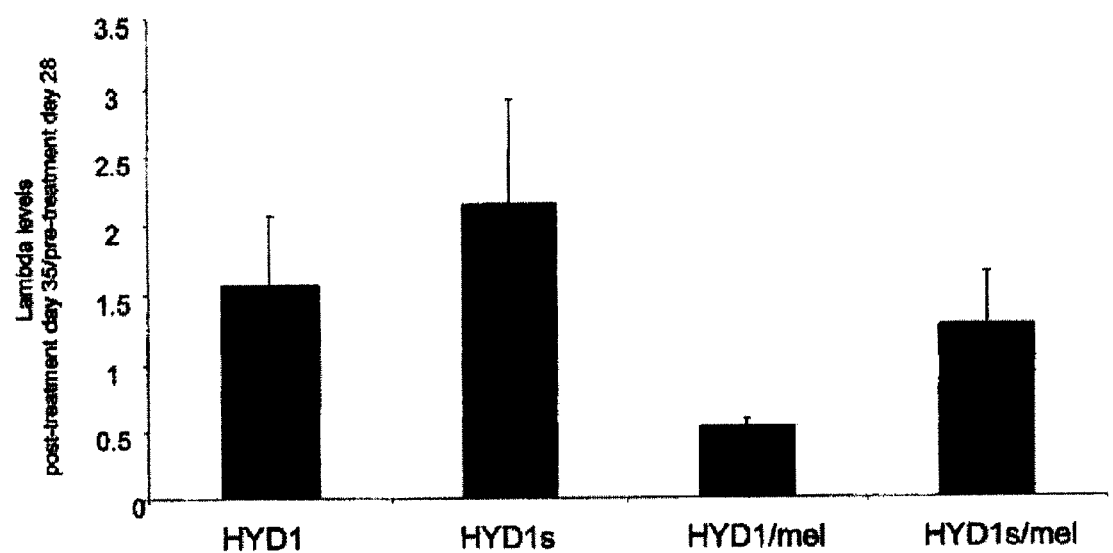
FIG. 8 is a graph showing that HYD1 enhances melphalan induced cell death of myeloma cells in the SCID-Hu in-vivo model. 8226 cells (50,000 cells per mice) were engrafted into implanted human bone for 28 days. Following tumor engraftment, mice were treated with either 2 mg/Kg HYD1 or HYD1S (I.P. daily). Appropriate mice were treated with 1.5 mg/kg melphalan (mel) on day 29 and day 33 (I.P. injections). Tumor burden was measured by lambda levels on day 28 and day 35 (n=3 mice per group).

As shown in FIG. 5, HYD1 but not HYD1S blocks cell adhesion of myeloma cells to the extracellular matrix FN. Briefly, 8226 myeloma cells were pre-incubated with varying concentrations of either HYD1 or the scrambled HYD1S peptide for 30 minutes prior to allowing cells to attach to FN for two hours. Following two hours of cell adhesion, the amount of cells adherent to FN was measured. The next objective was to determine whether treatment of tumor cells with HYD1 results in potentiation of melphalan induced cell death in the BMS co-culture model (SF+A). As shown in FIGS. 6 and 7, and consistent with the inventors' previous data, co-culturing myeloma cells with HS-5 cells (SF+A model) inhibits melphalan induced cell death compared to cells cultured in regular RPMI media containing 10% FBS (RM). Furthermore, treatment with HYD1 potentiates melphalan-induced apoptosis most dramatically in the SF+A model (drug specific apoptosis=melphalan induced apoptosis minus either no peptide, HYD1 only treatment or HYD1S only treatment). For these studies, the HYD1 and HYD1S were pre-incubated with the peptide for 30 minutes, and then cells and culture media containing the peptide were placed into the S-5 culture dish. Myeloma cells were co-cultured for an additional 3 hours with HS-5 cells before the addition of melphalan. Twenty-four hours after drug treatment, apoptosis was measured by Annexin V-PE positive events by FACS analysis. The HS-5 cells constitutively express GFP and thus it is possible to gate GFP negative cells only (myeloma cells) for the apoptotic analysis. Treatment with HYD1 did not result in detachment of the HS-5 cells as myeloma cells remained visibly attached to the HS-5 cells suggesting that multiple adhesion moieties regulate cell-cell attachment in the SF+A model system. Surprisingly, HYD1 also increased melphalan-induced apoptosis in suspension cells. Earlier reports have indicated that myeloma cell lines express and secrete soluble fibronectin (van Riet I, et al. *Br J. Haematol.* 1994; 87:258-265).

Example 5

Effects of HYD1 on Cell Adhesion

As shown in FIG. 5, HYD1 (kikmviswkg; SEQ ID NO:1), but not the scrambled version of HYD1S (wiksmkivkg; SEQ ID NO:44), blocks cell adhesion of myeloma cells to the extracelullar matrix firborenectin (FN). Briefly, 8226 myeloma cells were pre-incubated with varying concentrations of either HYD1 or the scrambled HYD1S peptide for 30 minutes prior to allowing cells to attach to FN for two hours.

Example 6

Effects of HYD1 on a Bone Marrow Stroma Model of Drug Resistance

Figure 9A:
FIGS. 9A-9C show an illustration of the BMS models of drug resistance.
Figure 9B:
Figure 9C:
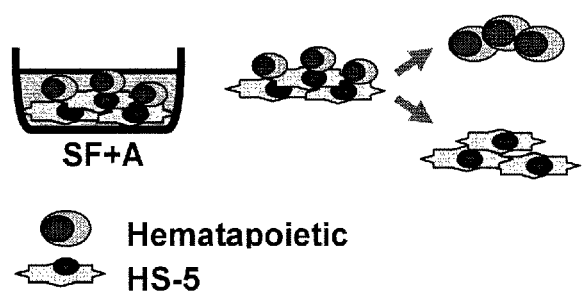
Figure 10A:
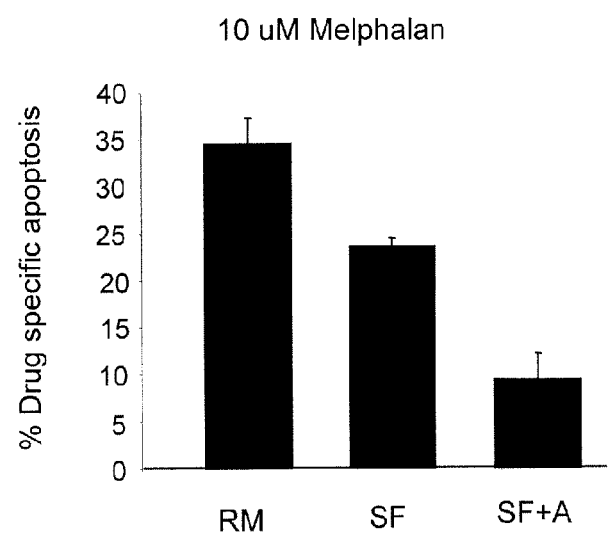
FIGS. 10A-10E are a series of graphs showing that the BMS model protects MM1.S cells from melphalan (FIG. 10A), mitoxantrone (FIG. 10B), dexamethasone (FIGS. 10C and 10D), and velcade (FIG. 10E) induced cell death.
Figure 10B:
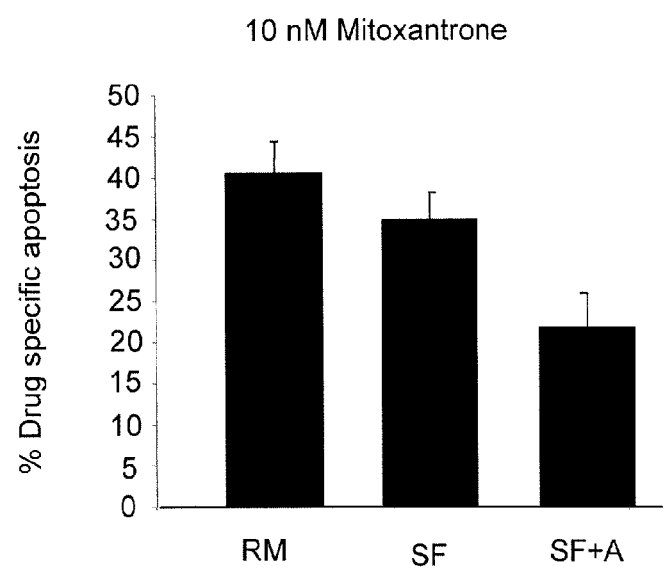
Figure 10C:
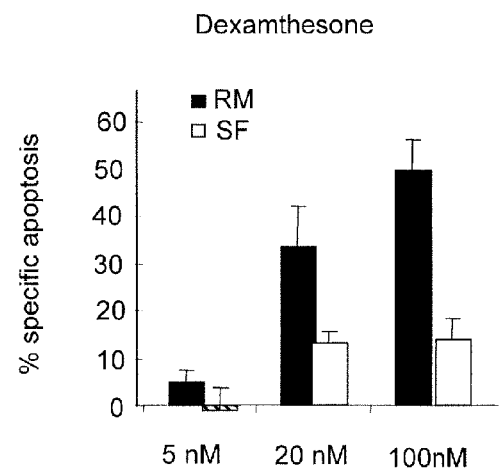
Figure 10D:
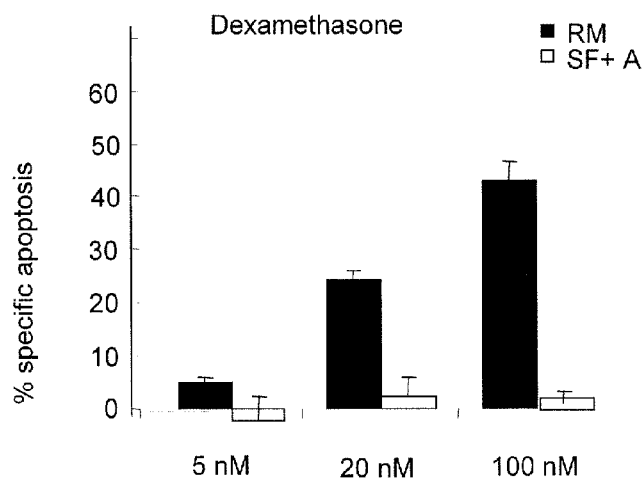
Figure 10E:
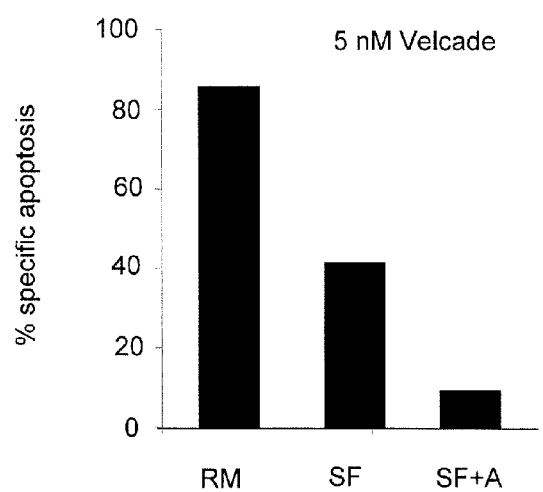

To test the hypothesis that HYD1 potentiates β1 integrin mediated drug resistance in the bone marrow microenvironment, a bone marrow stroma (BMS) model of drug resistance was developed. The BMS model systems are described in FIGS. 9A-C. These models have allowed three discrete hematopoietic tumor populations. The first MM population (FIG. 9A) is maintained in a traditional suspension culture in RPMI media containing 10% FBS (RM). The second MM cell population consists of placing HS-5 cells in the bottom chamber and MM cells in a top chamber that is separated by a membrane allowing for diffusion of soluble factors (see FIG. 9B). Finally, as shown in FIG. 9C, the third culture condition considers both cell adhesion and soluble interactions of MM cells and BMS cells. As shown in FIGS. 10A-E, using HS-5 cells as the stromal layer in the BMS model is sufficient to confer resistance to melphalan, mitoxantrone, velcade and dexamethasone induced cell death. Regardless of the cytotoxic agent used, the SF+A model, which allows for direct cell contact confers the greatest levels of drug resistance.

Figure 11:
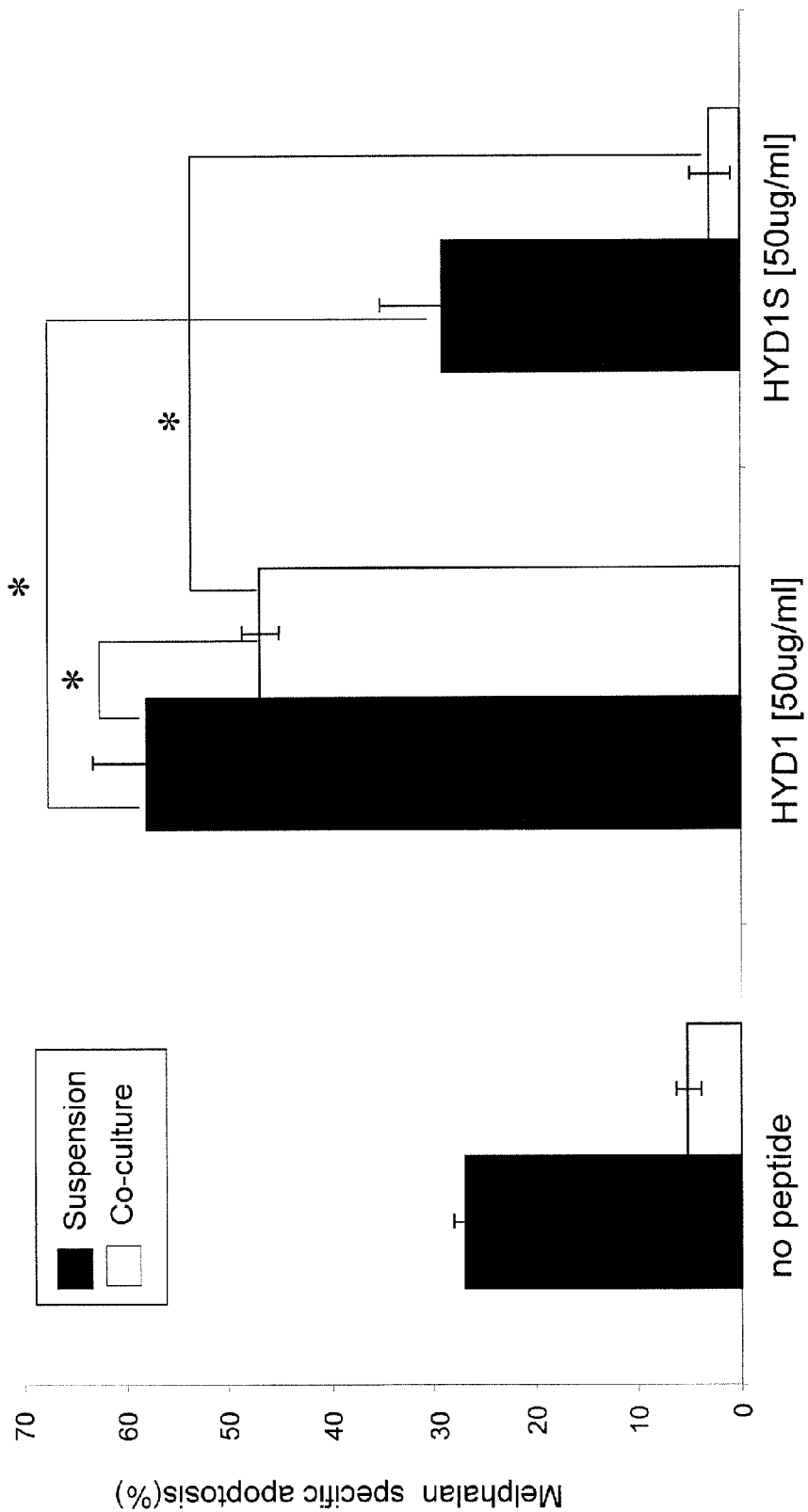
FIG. 11 is a graph showing that treatment of H929 cells with HYD1 but not the scrambled peptide (HYD1S) potentiates melphalan-induced cell death and decreases the resistance associated with the BMS co-culture model (*p<0.0125 p values corrected for multiple testing using Bonferroni-Holm Correction n=9).
Figure 12:
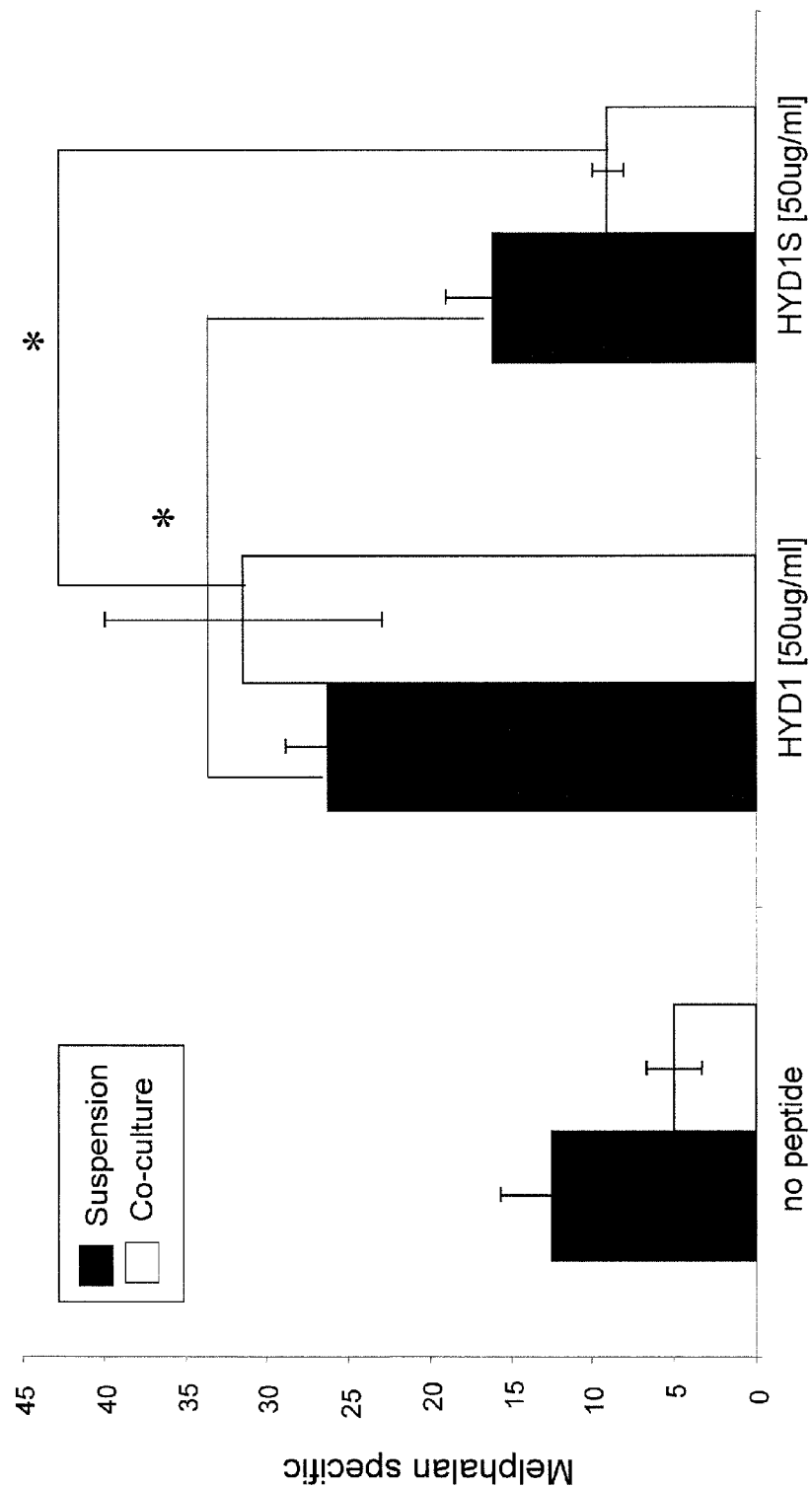
FIG. 12 is a graph showing that treatment of 8226 cells with HYD1 but not the scrambled peptide (HYD1S) potentiates melphalan-induced cell death and reverses resistance associated with co-culturing tumor cells with the BMS cell line HS-5 (*p<0.0125 p values corrected for multiple testing using Bonferroni-Holm Correction n=9).

As shown in FIGS. 11 and 12, co-culturing myeloma cells with HS-5 cells (SF+A model) inhibits melphalan induced cell death compared to cells that are cultured in suspension with RPMI media containing 10% FBS (RM). Importantly, treatment with HYD1 potentiates melphalan-induced apoptosis in the SF+A model ($p<0.05$ for 8226 and H929 cells). HYD1 treatment also increased melphalan-induced apoptosis in both H929 and 8226 cells cultured in suspension ($p<0.05$). 8226 cells treated with HYD1, showed no significant differences in melphalan induced apoptosis when co-cultured in the HS-5 (SF+A) model compared to cells cultured in suspension ($p>0.05$). These data indicate that cell adhesion mediated drug resistance has been reversed in the BMS drug resistant model. Earlier reports have indicated that myeloma cell lines express and secrete soluble fibronectin.

Figure 13:
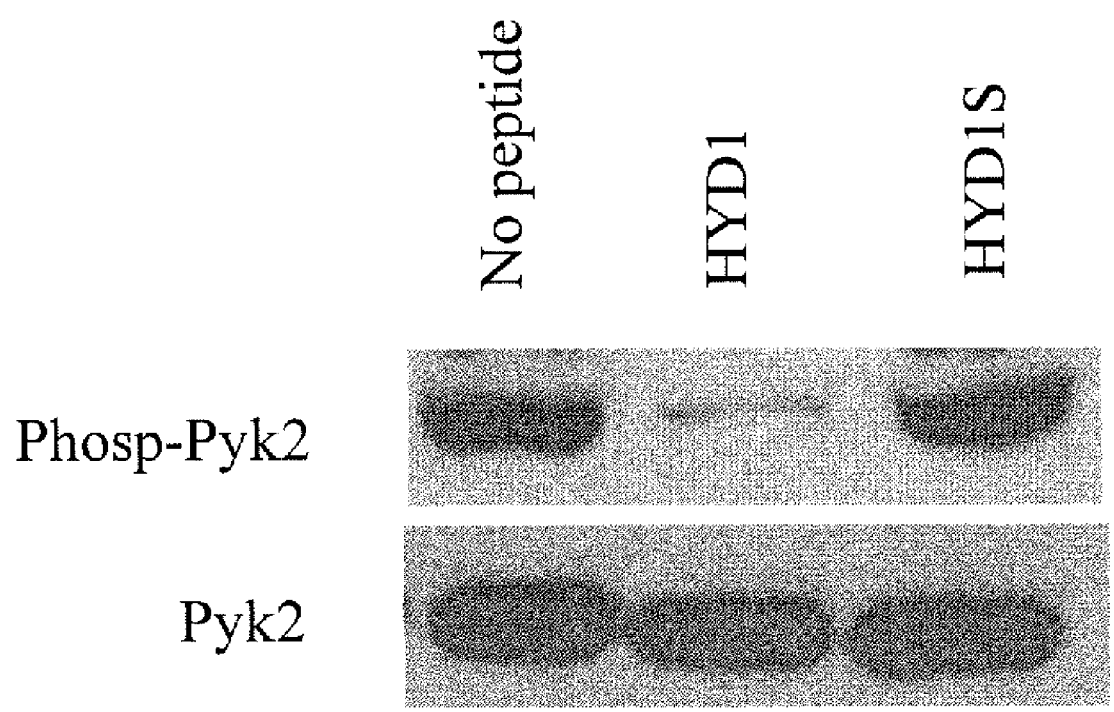
FIG. 13 illustrates that the HYD1 peptide inhibits phospho Pyk2 levels in H929 cells grown as a suspension culture.

Based upon the observation that HYD1 increased melphalan induced apoptosis in suspension cultures, whether treatment with HYD1 inhibits phosphorylation of a downstream mediator of β1 integrin signaling (Pyk2) in suspension cultures was investigated. As shown in FIG. 13, treating H929 cells with HYD1 but not HYD1S reduces phospho Pyk2 levels in H929 myeloma cells cultured in suspension. Taken together, these data suggest that MM cell lines may contain basal activation of β1 integrins in suspension cultures, perhaps as a result of secretion and the subsequent coating of FN on the cell surface of MM cells or via Example 7

Minimal Element of HYD1 to Support Cell Adhesion is kmvixw (SEQ ID NO:46)

Defining the minimal region of HYD1 necessary to potentiate drug-induced apoptosis in suspension and adherent cultures is of interest. Below is a study to determine the minimal HYD1 sequence required to block prostate tumor cell migration. Similar studies as those outlined below and using the same peptide sequences will be used to determine the minimal amino acid sequence required for potentiation of drug induced apoptosis.

Figure 14A:
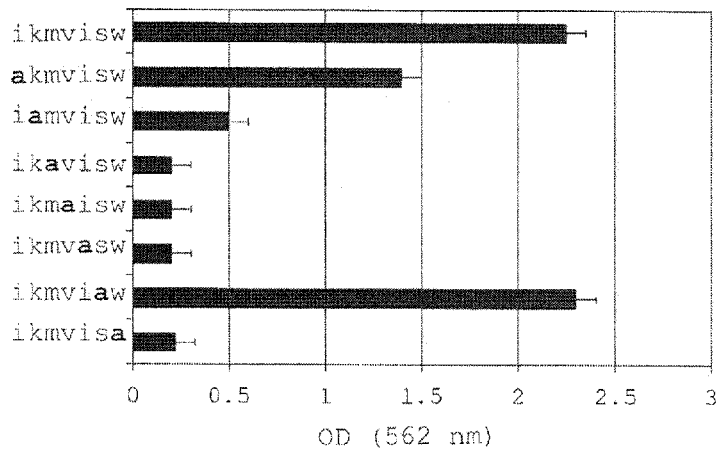
FIGS. 14A-14C show results of a truncation and substitution study of the HYD1 peptide (kikmviswkg; SEQ ID NO:1), establishing the minimal element of HYD1 to support cell adhesion.
Figure 14B:
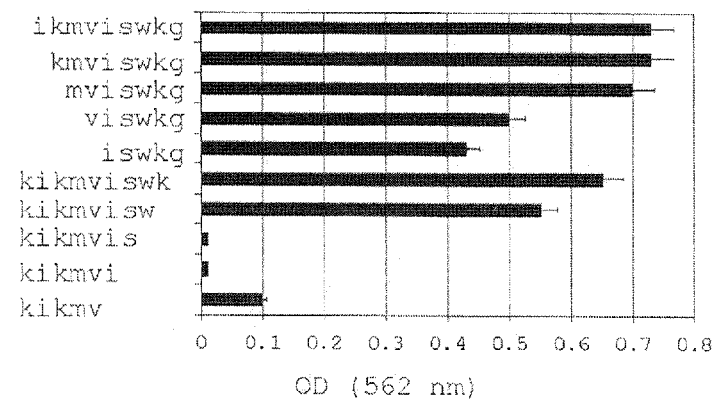
Figure 14C:
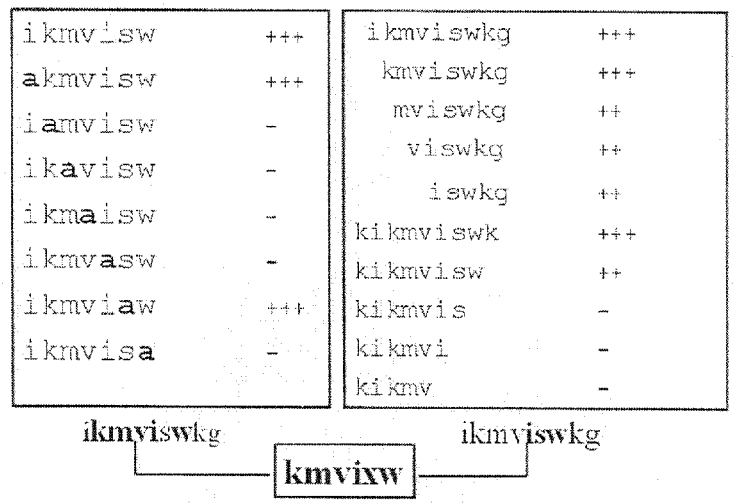

To determine the minimal element of immobilized HYD1 required for cell adhesion, the N and C terminus was systematically truncated one amino acid at a time (FIG. 14A). Most of the adhesion activity was retained with the deletion of lys-glycine from the C-terminus. However, the peptide no longer supported cell adhesion if the next residue, tryptophan was removed. Deletion of the N-terminus on the other hand, was tolerated very well until the third residue, methionine, was removed, leading to gradual decrease in cell binding. When HYD1 was truncated from both termini, it was found that ikmvisw (SEQ ID NO:19) peptide retained full cell adhesion activities. Alanine substitution analysis of this peptide indicated that the N-terminal isoleucine and one serine in the C-terminal region were not critical amino acids for cell adhesion (FIG. 14B). Taken together (FIG. 14C), these data show that the minimal element necessary for cell adhesion is kmvixw (SEQ ID NO:46).

Example 8

Blocking Migration Required xkmviswxx (SEQ ID NO:50)

Figure 15A:
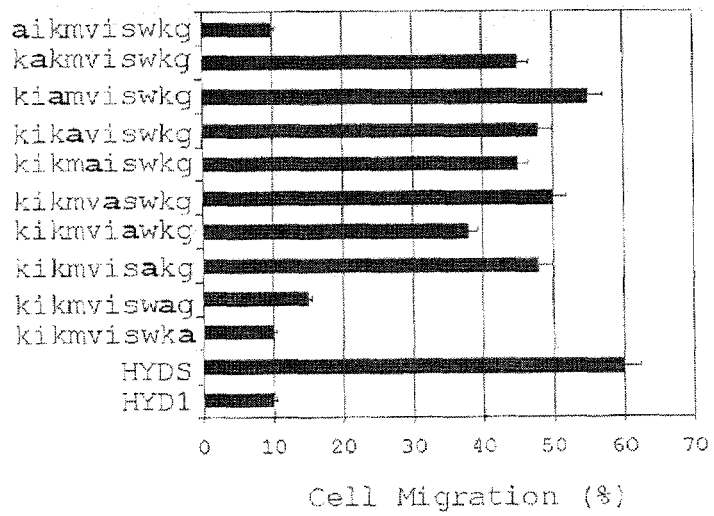
FIGS. 15A-15C show the results of a truncation and substitution study of the HYD1 peptide, establishing the active sequence for blocking cell migration.

HYD1 completely blocks random haptotaxis on laminin 322 (laminin 5). This response to the peptide is independent of disrupting adhesion to laminin 322 (laminin 5) since the cells were grown on a ligand before treatment with the peptide. Alanine-substitution analysis of HYD1 revealed that the N-terminal lysine and the final two C-terminal residues, a lysine and glycine, were not critical residues for blocking haptotaxis (FIG. 15A). All other alanine-substitution mutants resulted cell migration, i.e., a loss of peptide activity. These data suggest that the active sequence for blocking cell migration was kmvisw (SEQ ID NO:45).

Figure 15B:
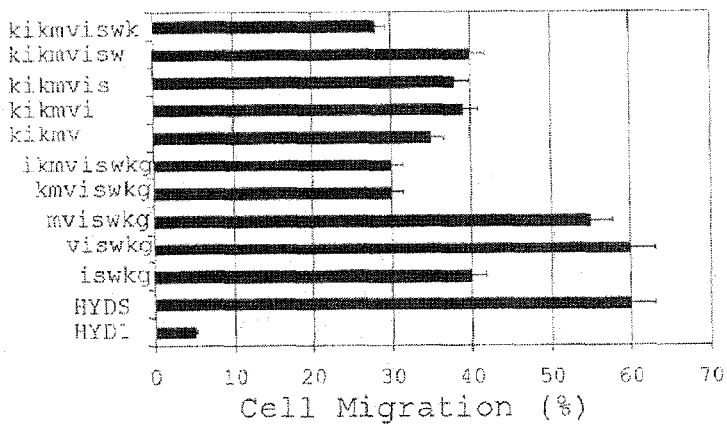
Figure 15C:
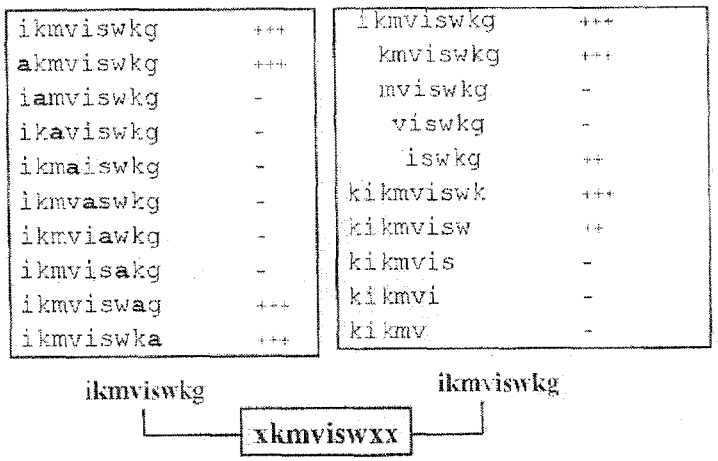

Analysis using the deletion variants of HYD1 showed that minimal deletion from either end of the peptide resulted in at least partial loss of activity (FIG. 15B). Using the negative control scrambled peptide, HYDS (SEQ ID NO:44), to indicate 100% cell migration, several truncated peptides including, ikmviswkg (SEQ ID NO:22), kmviswkg (SEQ ID NO:39), and kikmviswk (SEQ ID NO:37) were effective at blocking cell migration by approximately 50%. These data are consistent with the results found in the adhesion assays in that both the N- and C-terminal regions of HYD1 are responsible for its bioactivity. Taken together (FIG. 15C), these data show that the minimal element necessary to maximally block cell migration on laminin 322 (laminin 5) is xkmviswxx (SEQ ID NO:50).

Example 9

Activation of ERK Signaling Required ikmviswxx (SEQ ID NO:48)

HYD1, when introduced as a soluble ligand, completely blocks random hapotaxis on laminin 322 and enhanced cellular signals are coupled with the loss of cell motility. HYD1 induces activation of ERK that is maximal at 10 min post-treatment. Using this endpoint as an indicator of HYD1 bioactivity, the truncated and alanine-substituted variants of HYD1 were tested for their ability to activate ERK. Activation of ERK at 10 minutes post-treatment was conserved with alanine-substitution only at the N-terminal lysine and C-terminal glycine (FIG. 16A-1). All other alanine-substitution resulted in a loss of ERK activation, suggesting that the interior residues, ikmviswk (SEQ ID NO:47), are critical. Deletion analysis of HYD1 revealed that both N- and C-terminal regions are involved in activation of ERK (FIG. 16A-2). Specifically, the N-terminal 5 amino acid residues, kikmv (SEQ ID NO:29), and the C-terminal 5 amino acid residues, iswkg (SEQ ID NO:23), alone induced partial activation of ERK. The N-terminal region, kikmv (SEQ ID NO:29), induced a stronger signal than iswkg (SEQ ID NO:23). In addition, some of the truncated mutants were able to partially activate ERK (FIG. 16A-2); however, the amount of activation was substantially reduced in comparison to the full-length peptide. These data showed that both the N- and C-terminal regions of HYD1 contained an element that can induce ERK activation. Taken together (FIG. 16C-2), the results (FIGS. 16A-1, 16A-2, 16B, 16C-1) indicate that activation of ERK signaling required ikmviswxx (SEQ ID NO:48).

Example 10

HYD1 as a Synthetic Adhesion Ligand for A6 Containing Stem Cells

Other groups have recently shown that the A6 integrin contributes to hematopoietic stem and progenitor cell homing to the bone marrow. Experimentally, blocking A6 by a function blocking antibody profoundly inhibited bone marrow homing of long-term multi-lineage engrafting stem cells. This receptor was also important in the short-term repopulating stem cells (*Blood*, 107:3503-3510 (2006)). These results, coupled with the knowledge that tumor cells also home to the bone and interact with the bone extracellular laminin matrix, suggests that HYD1 (which inhibits tumor cell adhesion to laminin) can be used either to block homing to the bone or be used to retrieve tumor cells as they circulate in the blood.

The present inventors have shown that adhesion of hematopoietic tumor cell lines via β1 integrins can be blocked by HYD1. In addition, HYD1 has been demonstrated bind to the cell surface. Furthermore, binding of HYD1 to the cell surface is blocked by the addition of antibodies that recognize the external domain of the β1 integrin receptor[31]. Finally, the inventors have obtained data showing that treatment of myeloma cell lines with HYD1 reverses drug resistance associated with co-culturing tumor cells with a bone marrow stroma cell line.

Example 11

Cell Adhesion

Figure 30A:
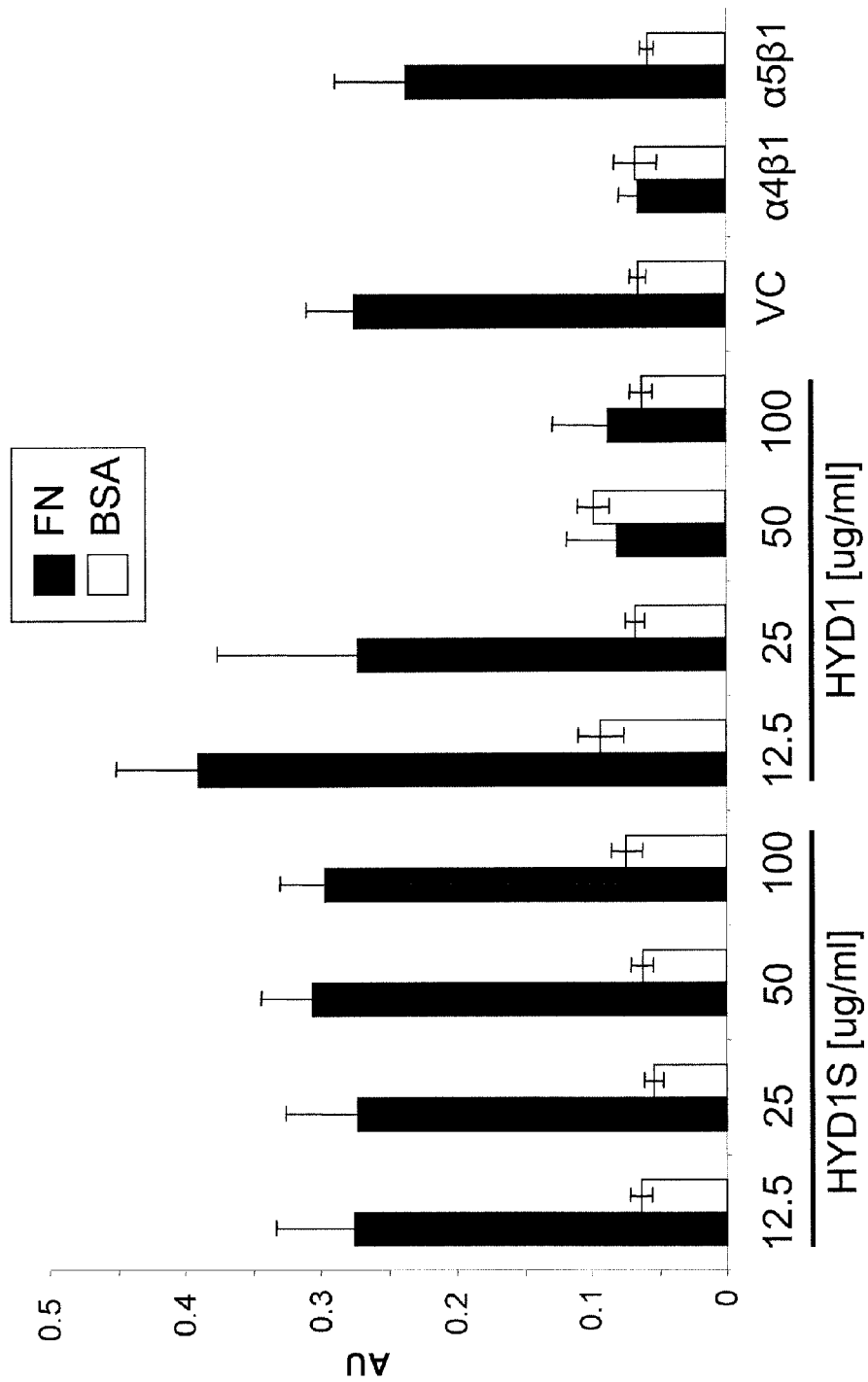
FIGS. 30A and 30B are graphs showing that HYD1 but not the scrambled derivative HYD1S inhibited cell adhesion of both 8226 and H929 cells to FN. Varying concentrations of either HYD1, HYD1S, or a 1:100 dilution of either α4β1 or α5β1 integrin functional blocking antibodies was added to either (FIG. 30A) 8226 cell or (FIG. 30B) H929 cells for 30 minutes prior to adding cells to either FN or BSA coated wells. Cells were allowed to adhere for 2 hours and adherent cells were measured by crystal violet staining at 540 nm. Shown is the mean and standard deviation of a representative experiment performed in quadruplicate. Three independent experiments were performed and similar results were obtained.
Figure 30B:
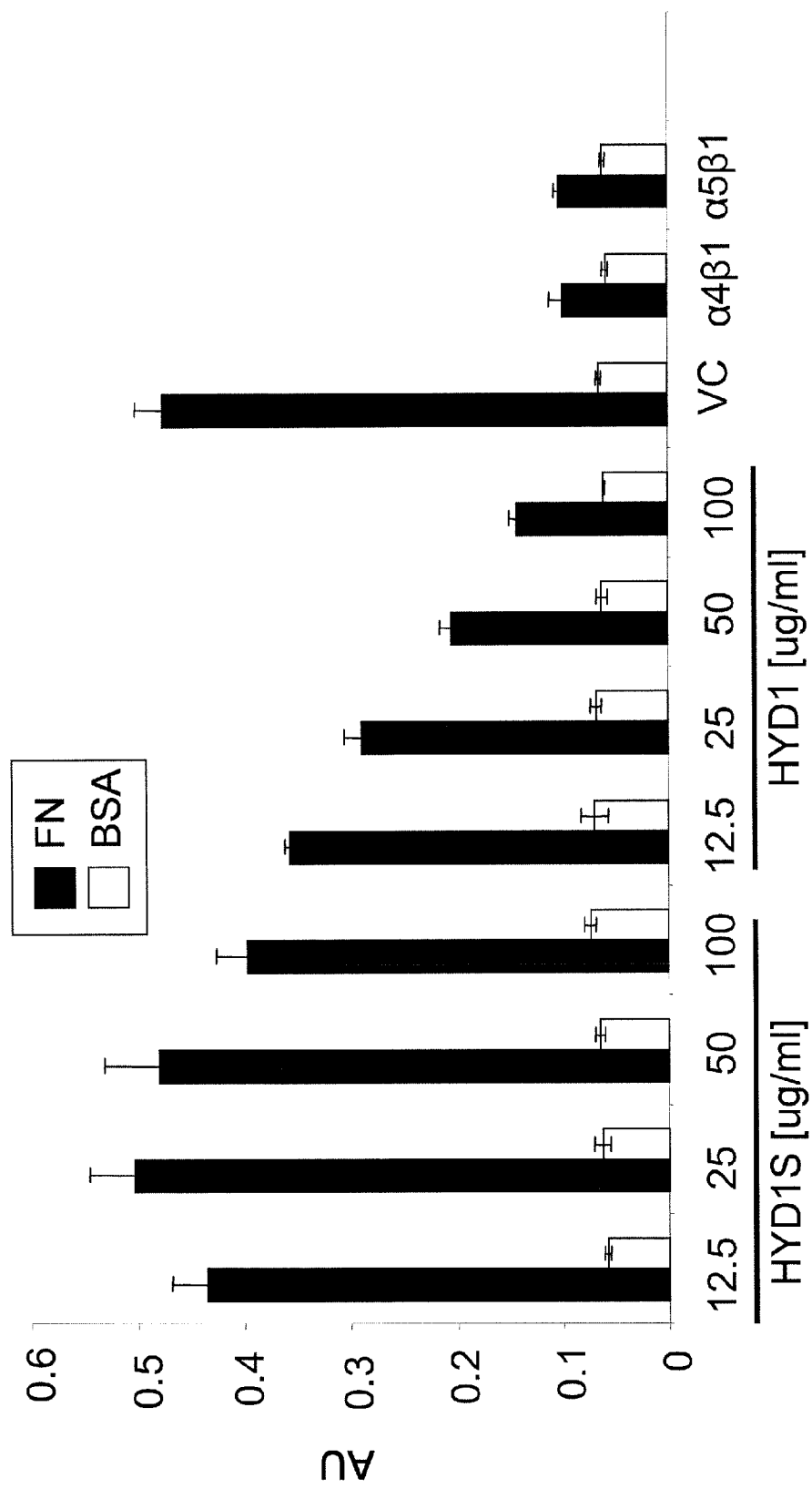

HYD1 was previously shown to inhibit adhesion of DUH-H prostate carcinoma cells (selected from DU145 cells using FACS to select cells expressing high levels of α6 integrin) to various extracellular matrixes including fibronectin (FN), laminin 1, laminin 5, and collagen V (DeRoock I B et al. *Cancer Res.*, 2001; 61:3308-3313). The first objective was to determine whether HYD1 blocks cell adhesion of myeloma cell lines to FN. As shown in FIGS. 30A and 30B, HYD1 but not HYD1S blocks adhesion of 8226 and H929 cells to the extracellular matrix FN in a dose dependent manner.

Figure 31A:
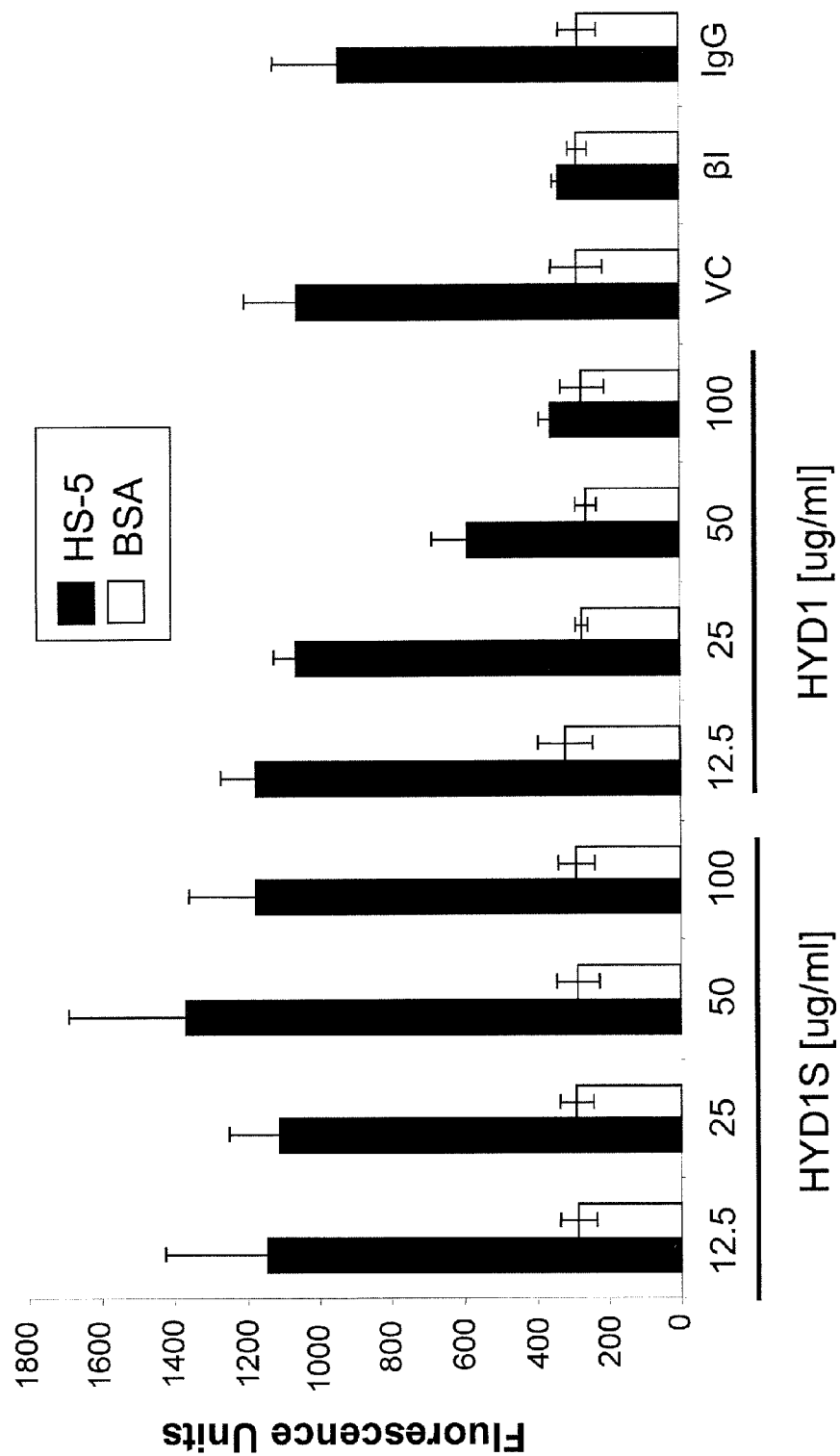
FIGS. 31A and 31B are graphs showing that HYD1 blocks adhesion of 8226 but not H929 cells to the bone marrow stroma cell line HS-5. Varying concentrations of either HYD1, HYD1S or a 1:100 dilution of a β1 integrin functional blocking antibody was added to either (FIG. 31A) CMFDA labeled 8226 cells or (FIG. 31B) CMFDA labeled H929 cells for 30 minutes prior to adding fluorescently labeled cells to either HS-5 or BSA coated wells for two hours. Unadhered cells were gently removed and adherent cells were quantified by total fluorescence. The independent experiments were performed and similar results were obtained.
Figure 31B:
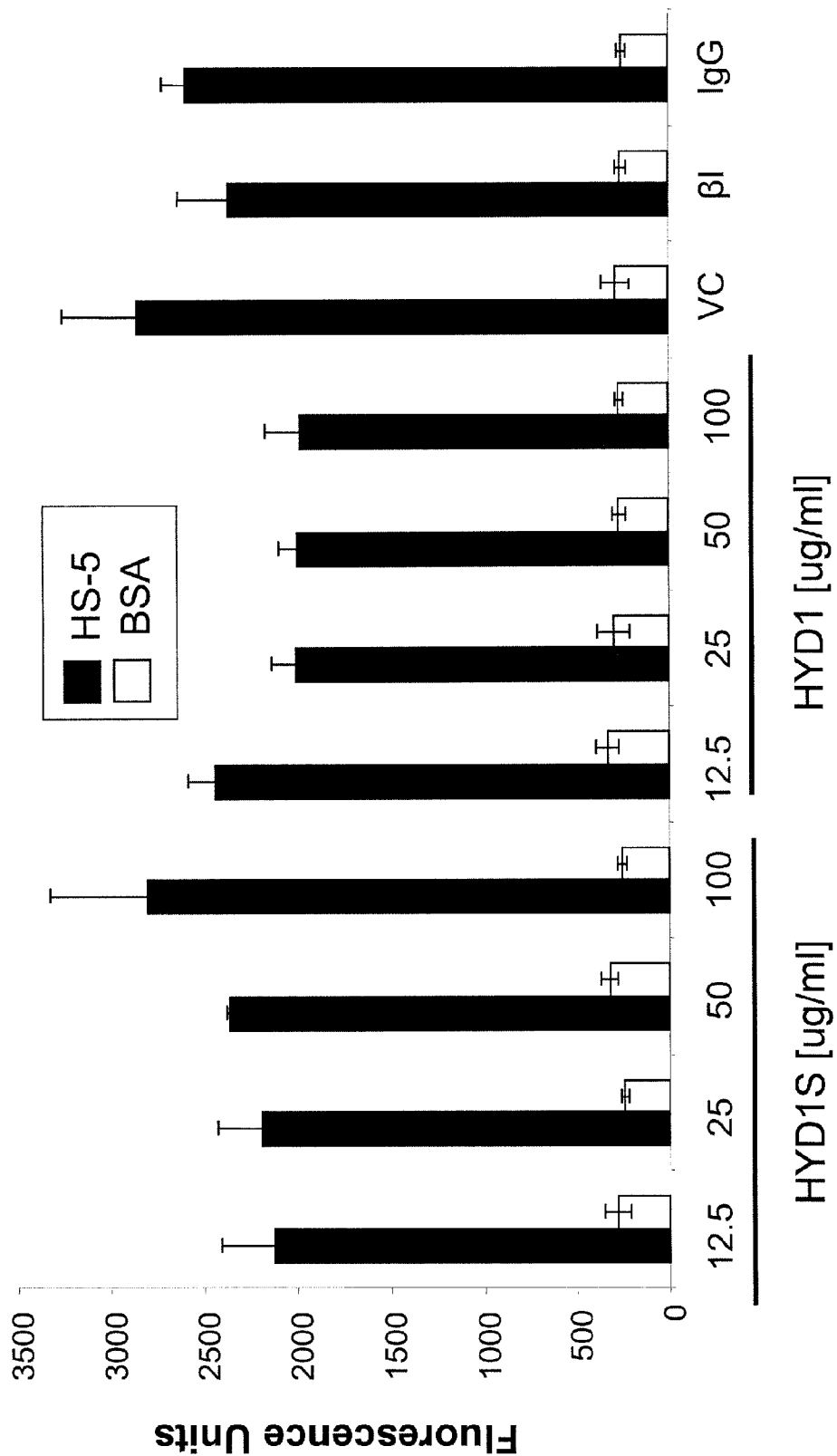

It was expected that adhesion of myeloma cells to bone marrow stroma cells would likely be multifactorial. This premise was tested directly by labeling MM cells with the fluorescent dye CMFDA and measured MM cell attachment to HS-5 cells in the presence of varying concentrations of HYD1, HYD1S or a 1:100 dilution of a functional β1 blocking antibody. As shown in FIGS. 31A and 31B, HYD1 partially blocked 8226 cells from binding to HS-5 cells, while having no effect on the H929 cells. The results obtained with HYD1 treatment in the two cell lines were similar with what was observed with the β1 blocking antibody.

Example 12

In Vitro Activity of HYD1

Figure 17:
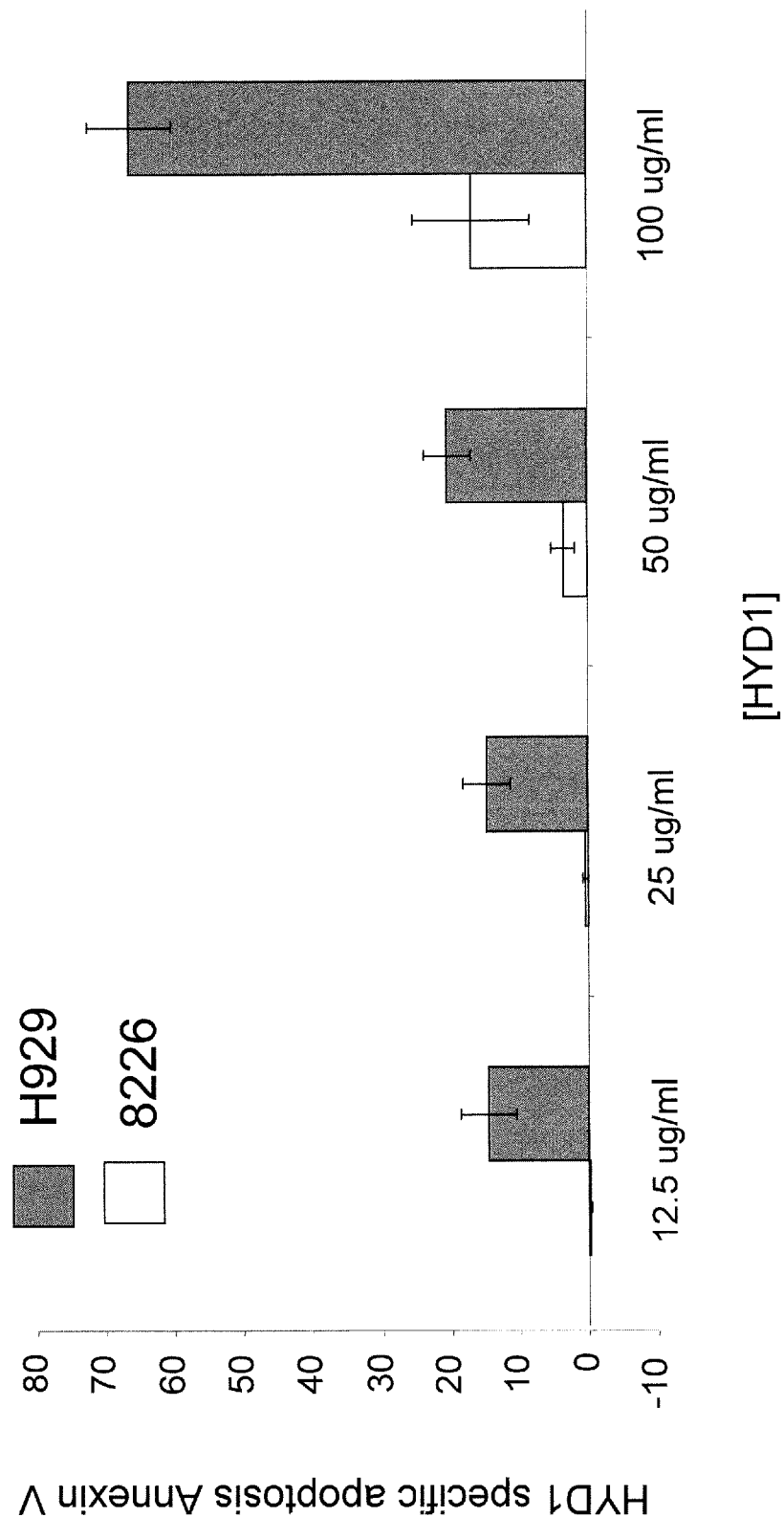
FIG. 17 is a graph showing that HYD1 induces apoptosis as a single agent in 8226 and H929 cells cultured in suspension. 8226 and H929 cells were either treated with varying concentrations of HYD1 or vehicle control (equal volume sterile double distilled water) for 24 hours and apoptotic cells were detected by FACS analysis of annexin V positive cells. HYD1 specific apoptosis equals cell death due to peptide minus any apoptosis detected in control cells.
Figure 18A:
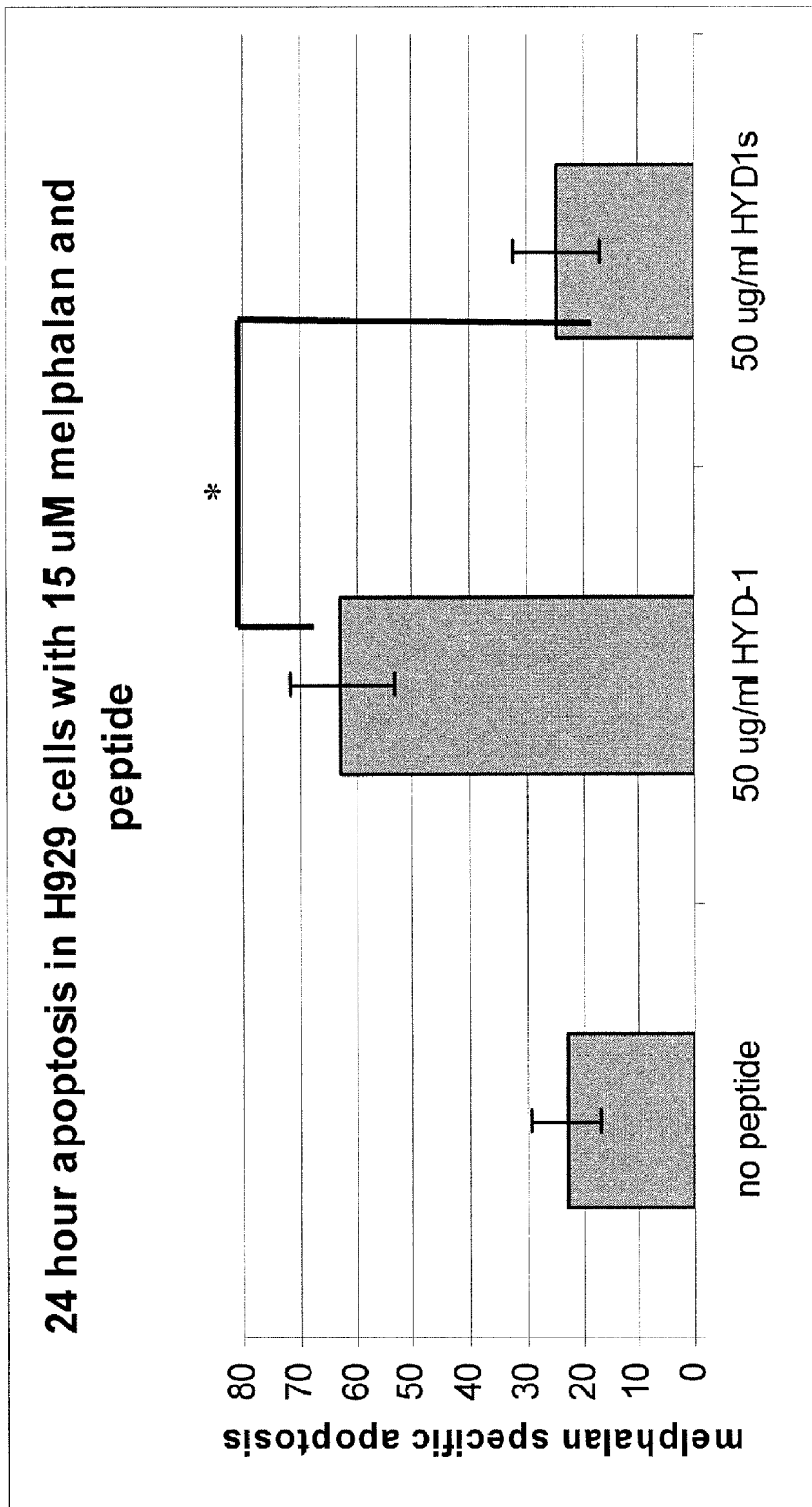
FIG. 18A is a graph showing 24-hour apoptosis in H929 cells with 15 µM melphalan and HYD1 peptide.
Figure 18B:
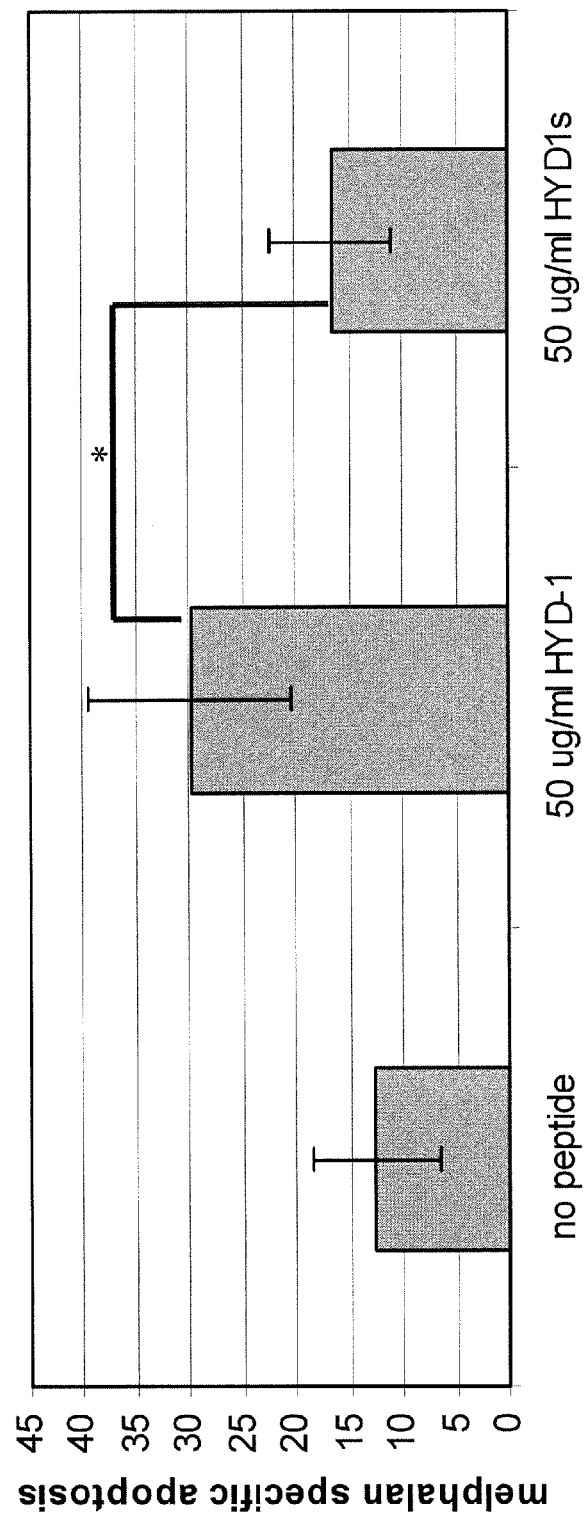
FIG. 18B is a graph showing 24-hour apoptosis in 8226 cells treated with 20 µM melphalan and HYD1 peptide.
Figure 19:
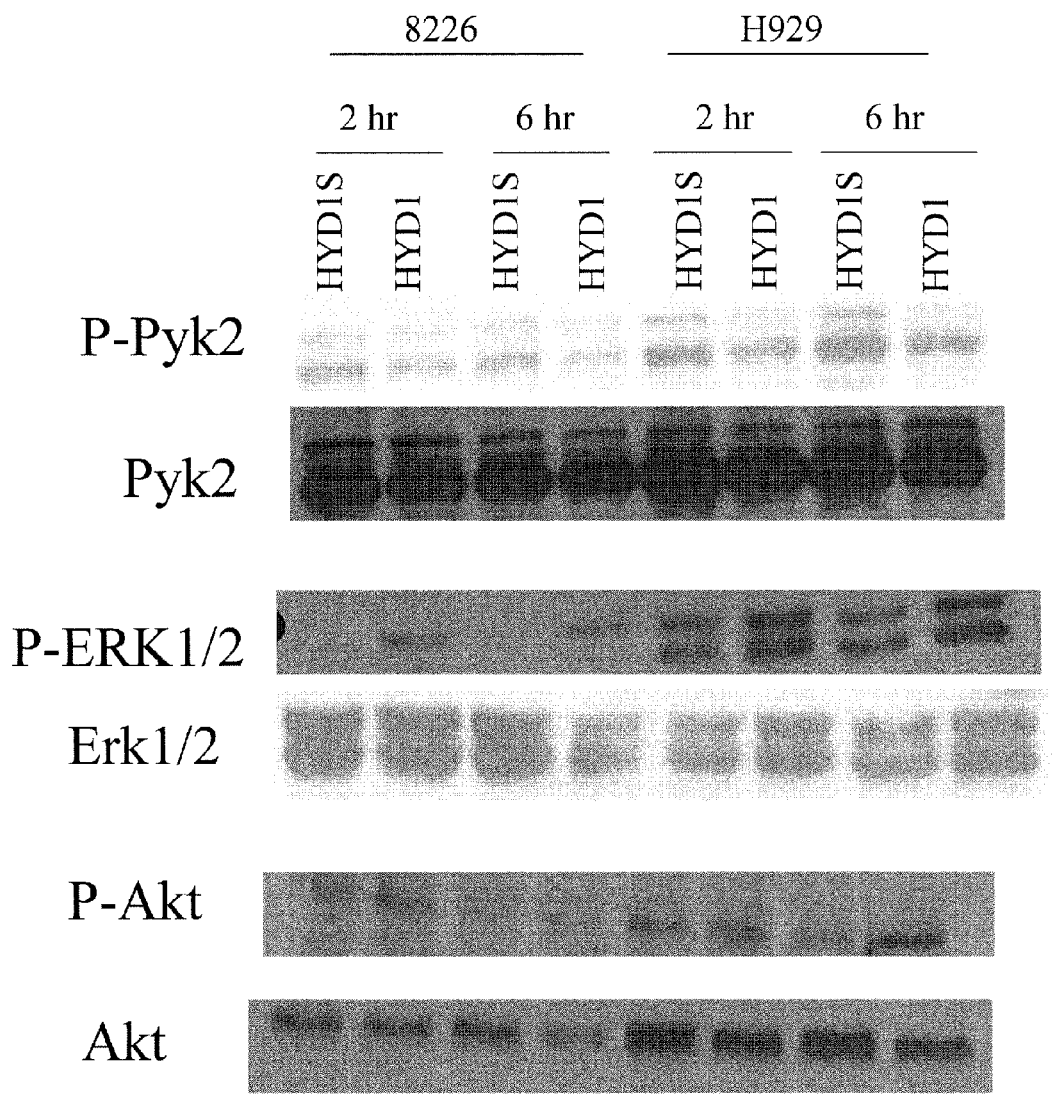
FIG. 19 are immunoblots showing that HYD1 treatment results in decreased levels of phospho-Pyk2 in both 8226 and H929 cells.

It was hypothesized that HYD1 would reverse drug resistance associated β1 integrin mediated with cell adhesion. Based on the initial hypothesis, it was expected that cell adhesion would be required to observe any anti-tumor activity associated with HYD1 treatment. However, surprisingly, annexin V positive cells were detected following HYD1 treatment when myeloma cells were cultured in suspension. As shown in FIG. 17, when either H929 or 8226 cells are cultured in a traditional suspension culture, HYD1 caused a dose dependent induction of annexin V positive cells. Because these cell death assays were performed in suspension cultures these data suggest that perhaps either a) myeloma cells contain a basal activation of β1 integrins prior to physical cell adhesion or b) the peptide acts as a partial agonist but in the absence of cell adhesion results in cell death. Moreover, it was observed that H929 cells are more sensitive to HYD1 treatment compared to 8226 cells, indicating that some cell lines may be more dependent on appropriate β1 integrin signaling for cell survival.

Example 13

Cell Death Pathway(s) Activated with HYD1 Treatment

Figure 21A:
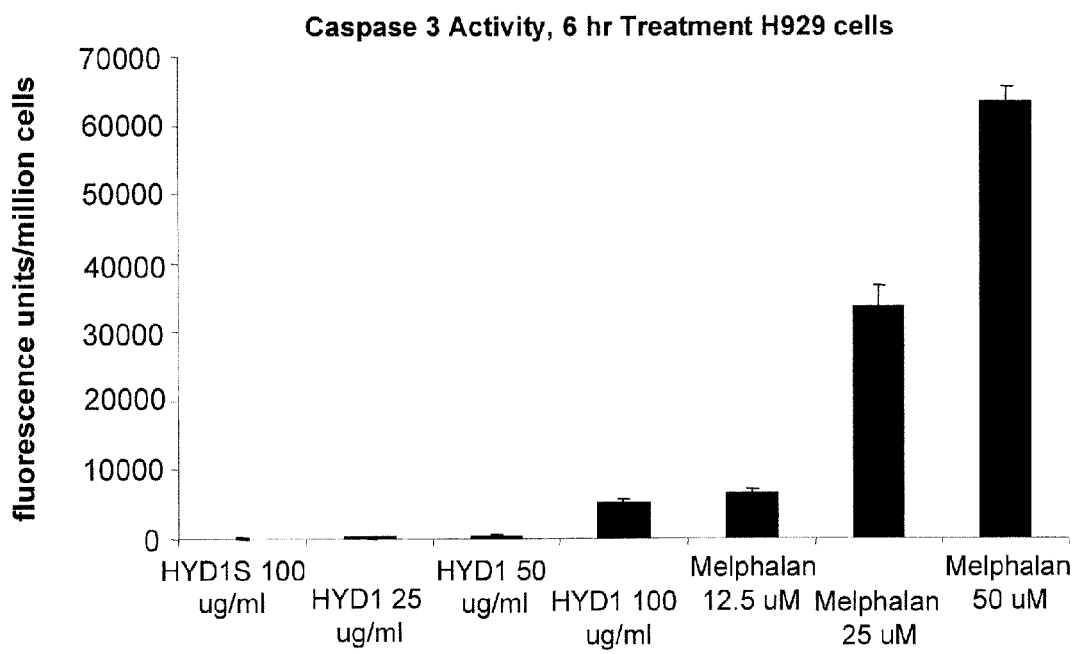
FIGS. 21A and 21B show that HYD1 induces minimal caspase 3 activity compared to melphalan treatment in H929 cells. Cells were treated for 6 hours (FIG. 21A) or 24 hours (FIG. 21B) and caspase 3 activity was measured using a fluorescent substrate. Shown is a representative experiment performed in triplicate. The experiment was repeated twice and similar results were obtained.
Figure 21B:
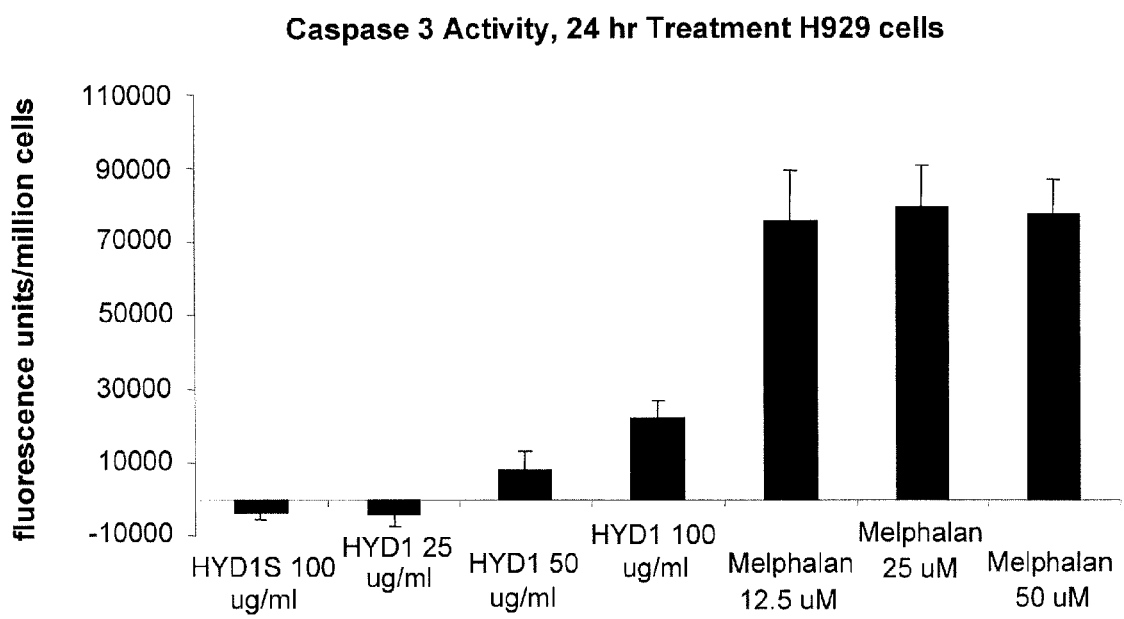
Figure 21C:
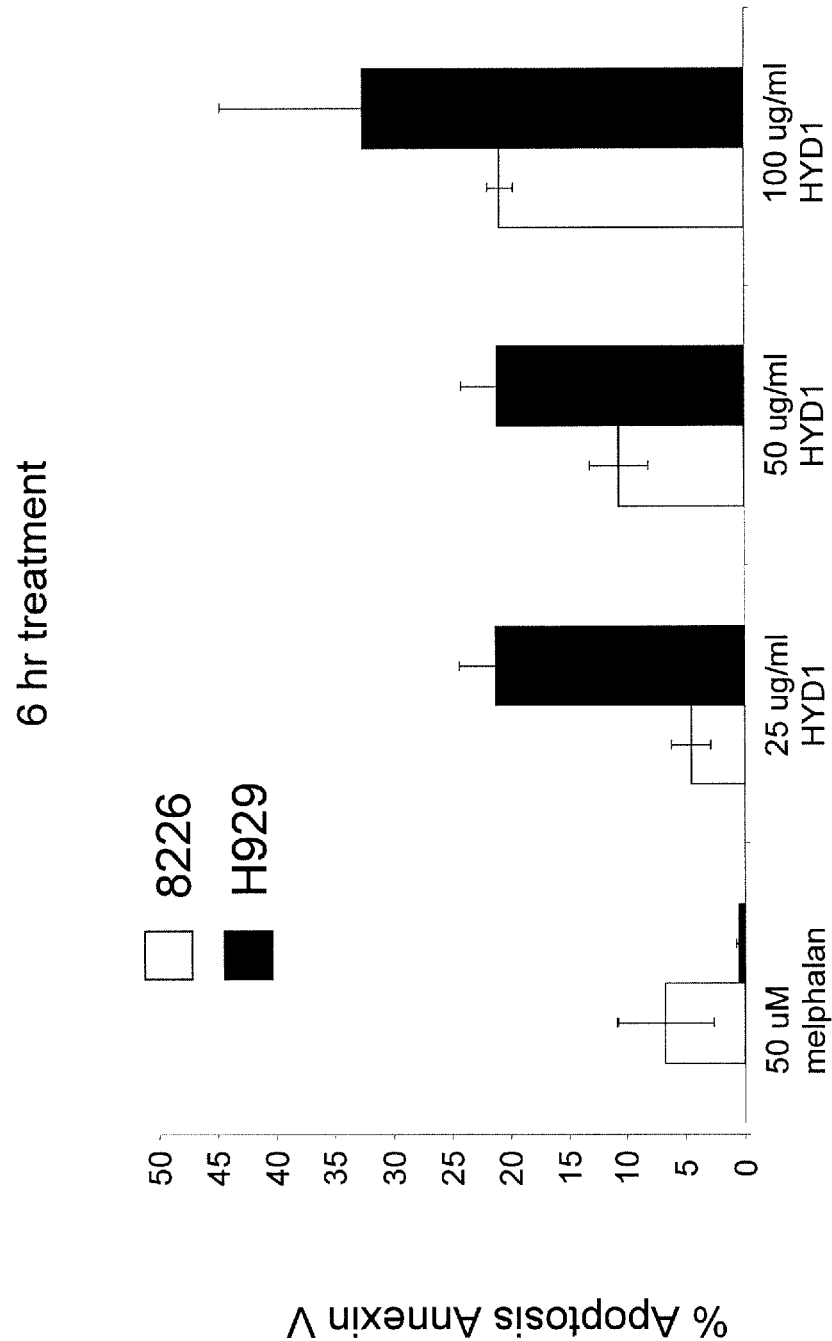
FIG. 21C shows that despite minimal caspase 3 and no caspase 8 activity, HYD1 induced annexin V positive cells can be detected following 6 hours of HYD1 treatment.
Figure 22A:
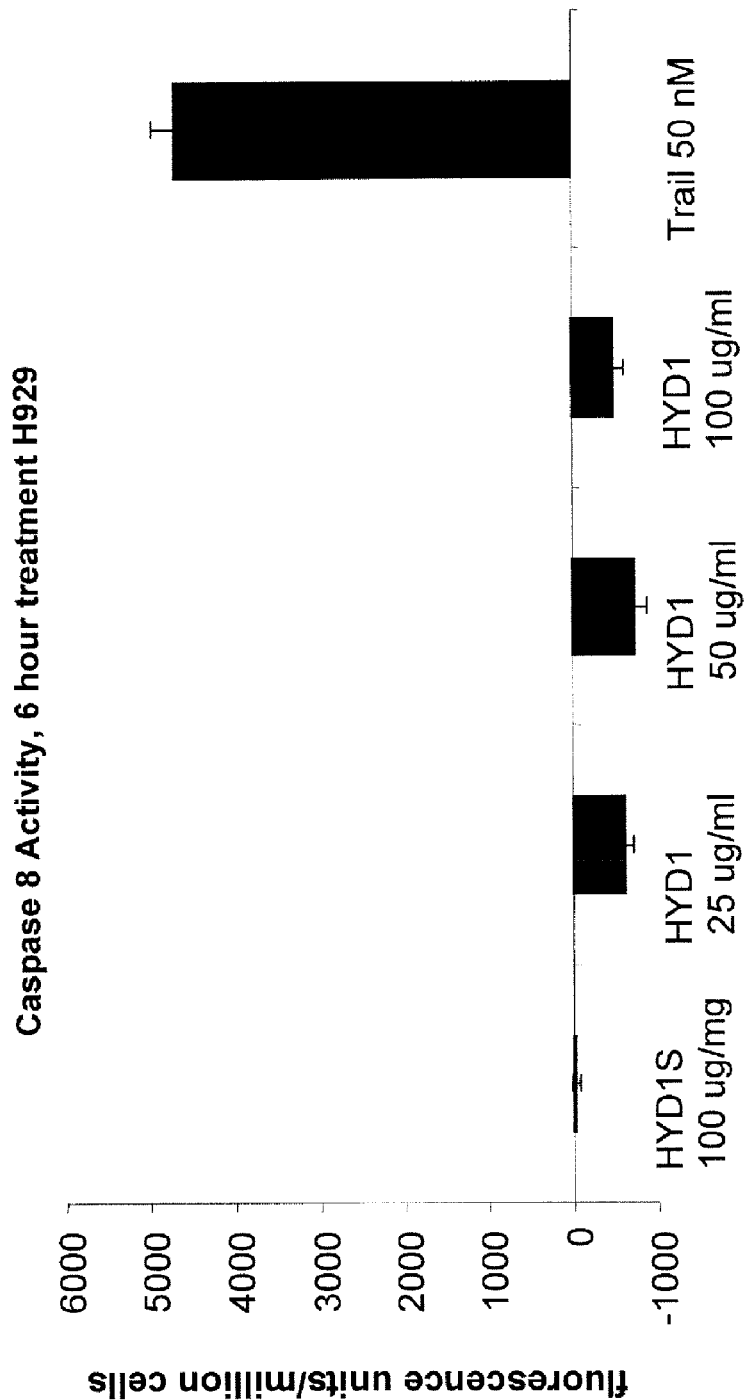
FIGS. 22A and 22B show that HYD1 induces no caspase 8 activity in H929 cells. Cells were treated for 6 hours (FIG. 22A) or 24 hours (FIG. 22B) and caspase 8 activity was measured using a fluorescent substrate. Shown is a representative experiment performed in triplicates. The experiment was repeated twice and similar results were obtained.
Figure 22B:
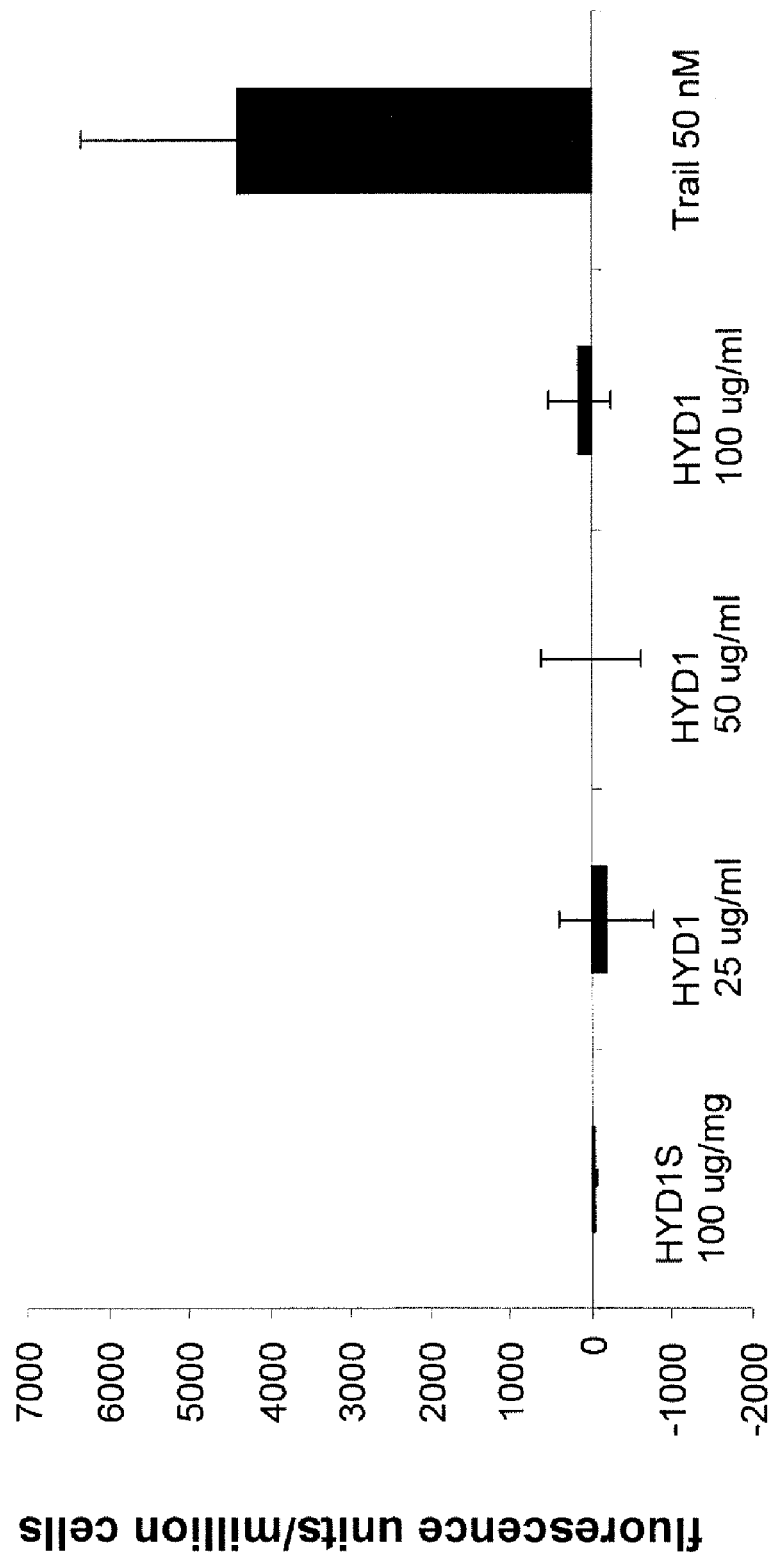
Figure 23D:
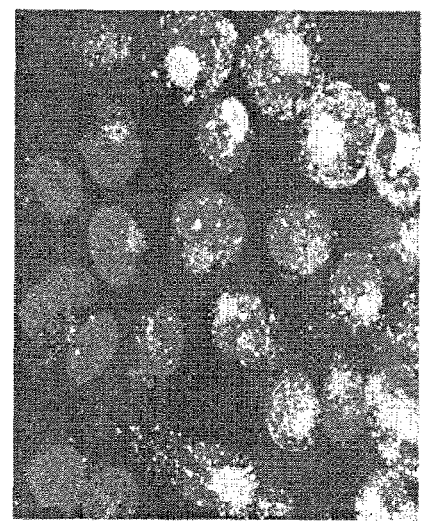
Figure 23E:
Figure 23F:
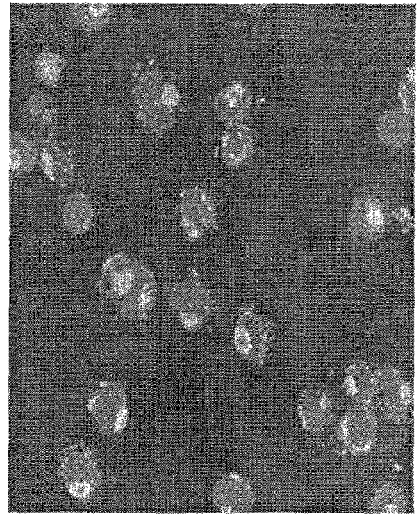

H929 cells were analyzed further to determine whether HYD1 induced cell death was caspase dependent or independent. As shown in FIGS. 20A-20F, the pan caspase inhibitor ZVAD-FMK only marginally protected H929 cells from cell death induced by HYD1. In contrast, ZVAD-FMK treatment blocked the majority of melphalan-treated annexin V positive cells (FIGS. 20A-20F). The dependence of caspase activation was examined by directly measuring caspase activity. For these studies, H929 cells were treated with HYD1 for 6 and 24 hrs and measured caspase 3 and 8 activity. HYD1 treatment induced minimal caspase 3 activity (see FIGS. 21A and 21B) relative to treatment with melphalan. In addition, no caspase 8 activity was detected at either 6 or 24 hrs treatment with HYD1 treatment (see FIGS. 22A and 22B). Together, the data indicate that HYD1 treatment induces a caspase independent mechanism of cell death.

Example 14

Effects of HYD1 on the Induction of Autophagy

Figures 24A, 24B:
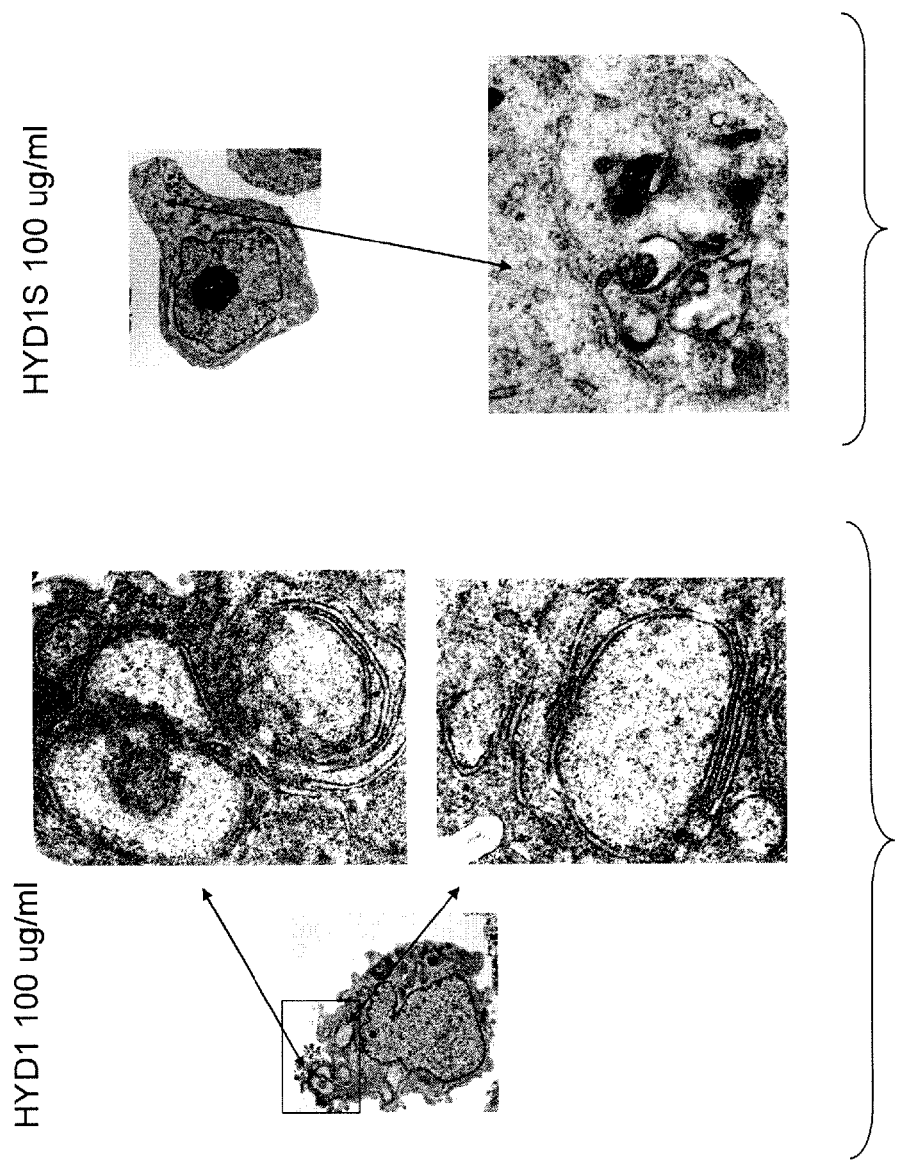
FIGS. 24A and 24B demonstrate that H929 cells show an increase in double membrane containing vesicles. H929 cells were treated with either 100 g/ml HYD1 (FIG. 24A) or HYD1S (FIG. 24B) for four hours and processed for electron microscopy as described in materials and methods.
Figure 25:
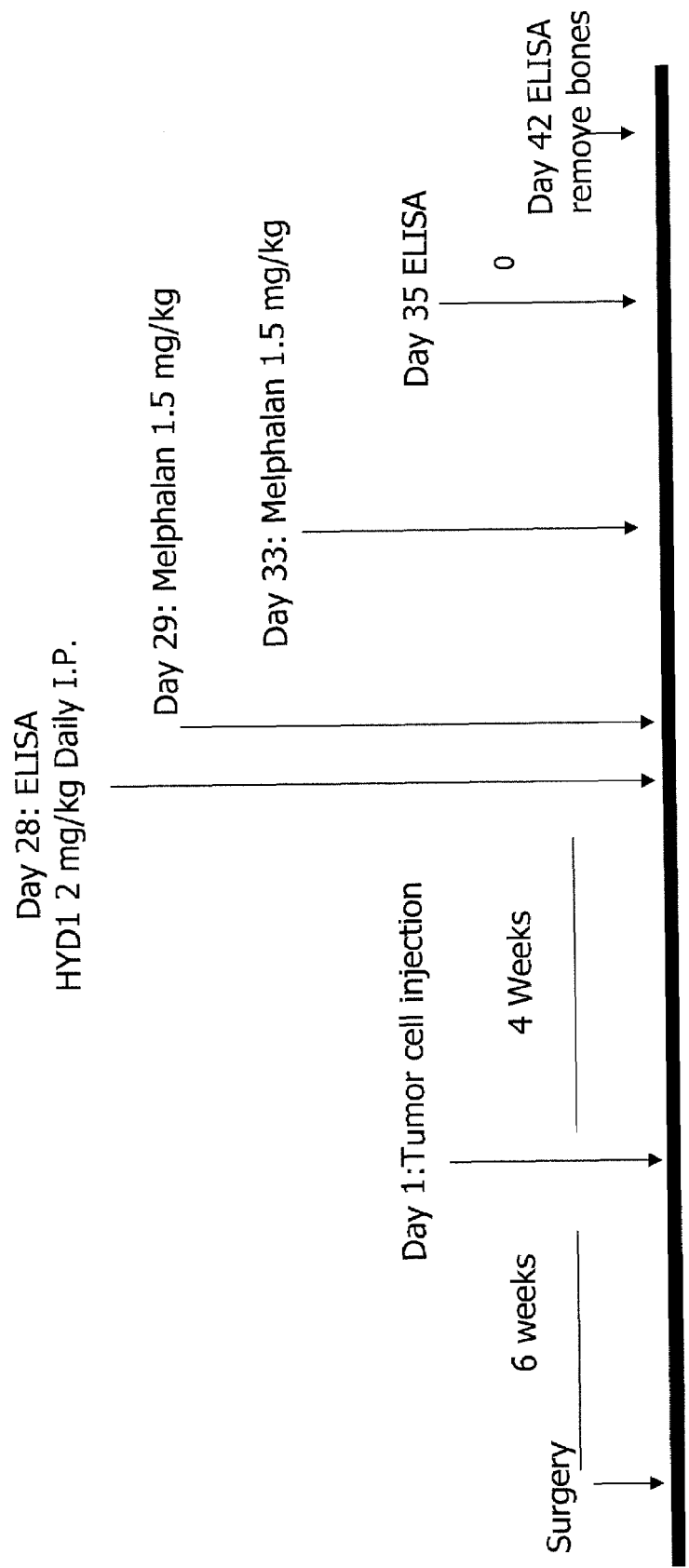
FIG. 25 shows the treatment schedule of the SCID-Hu in vivo model.

Autophagy represents one mechanism of cell death, which is reported to occur independently of caspase activation. Autophagic cell death is characterized morphologically by the appearance of double-membrane containing cytoplasmic vesicles. These vesicles typically engulf cytoplasmic content including organdies such as mitochondria and the endoplasmic reticulum. Eventually, autophagic vesicles will fuse with lysosomes resulting in degradation of the contents. Initially, lysosensor green staining and confocal microscopy were used to determine whether treatment of HYD1 resulted in an increase in the size or number of acidic vesicles. As shown in FIGS. 23A-23L, both 8236 and H929 cells treated with HYD1 for six hours caused an increase in the number and size of acidic vesicles compared to control cells. Electron microscopy (EM) was used to determine whether HYD1 treatment result an increase in the formation of double membranes. As shown in FIGS. 24A and 24B, treatment with HYD1 for 4 hours resulted in increased formation of double membranes, and morphologically is similar to reports consistent with ER-phagy. In control HYD1S treated cells, small vesicles fused with lysosomes were observed; however, the large vesicles noted with HYD1 treatment in both the lysosensor staining and EM analysis were not detected. Taken together, the data indicate that HYD1 is likely to induce an autophagic mechanism of cell death.

Example 15

Effects of HYD1 in the Co-Culture Model of MM Drug Resistance

The HS-5 co-culture model system was used to determine what effect HYD1 treatment has on drug resistance associated with the bone marrow microenvironment. Melphalan was used as the cytotoxic agent, and shown in FIGS. 11 and 12 are the levels of resistance associated with the co-culture model. In conditions where HYD1 was added, cell death due to the peptide was subtracted and thus the y-axis represents melphalan-specific apoptosis for each condition. When HYD1 was combined with melphalan treatment, a significant increase in melphalan specific apoptosis compared to cells treated with HYD1S (p<0.0125 ANOVO) in both suspension and co-culture growth was observed. Moreover, HYD1 reduced resistance associated when H929 cells were co-cultured with HS-5 cells and completely reversed resistance associated with the bone marrow stroma model in 8226 cells (see FIGS. 11 and 12).

Example 16

In Vivo Activity of HYD1

Figure 26:
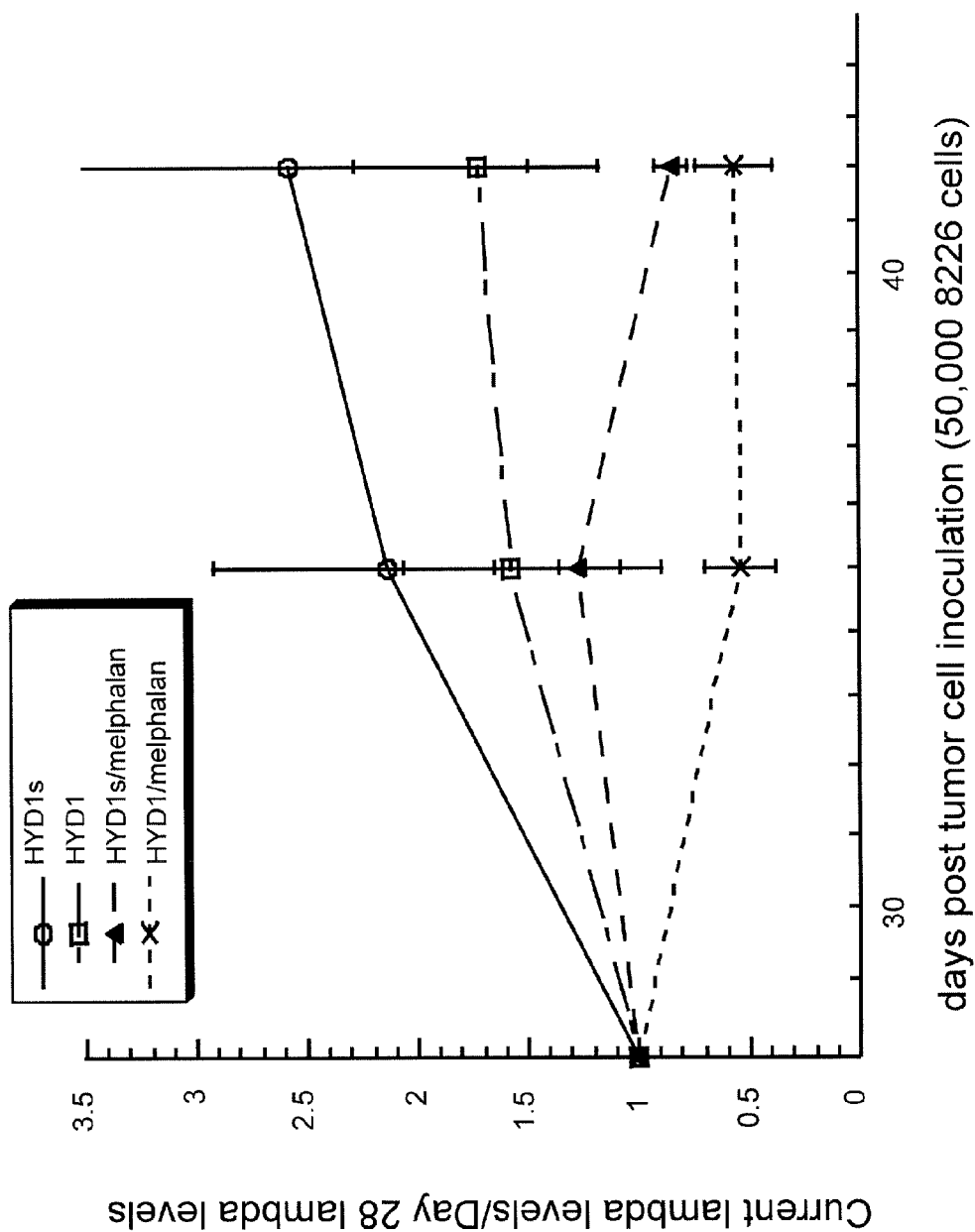
FIGS. 26 and 27 are graphs showing that HYD1 treatment reduces 8226 MM growth in vivo compared to vehicle control treatment. Tumor burden was measured by circulating lambda levels. On day 28 (before drug treatment) measurements were recorded for each individual mouse and subsequent values obtained weekly are represented as a ratio of day 28 (day X/day 28). N=4 mice per group. HYD1 was administered I.P. at 2 mg/kg daily for 14 days (starting day 28). Melphalan was administered I.P. at 1.5 mg/kg on day 29 and 32.
Figure 27:
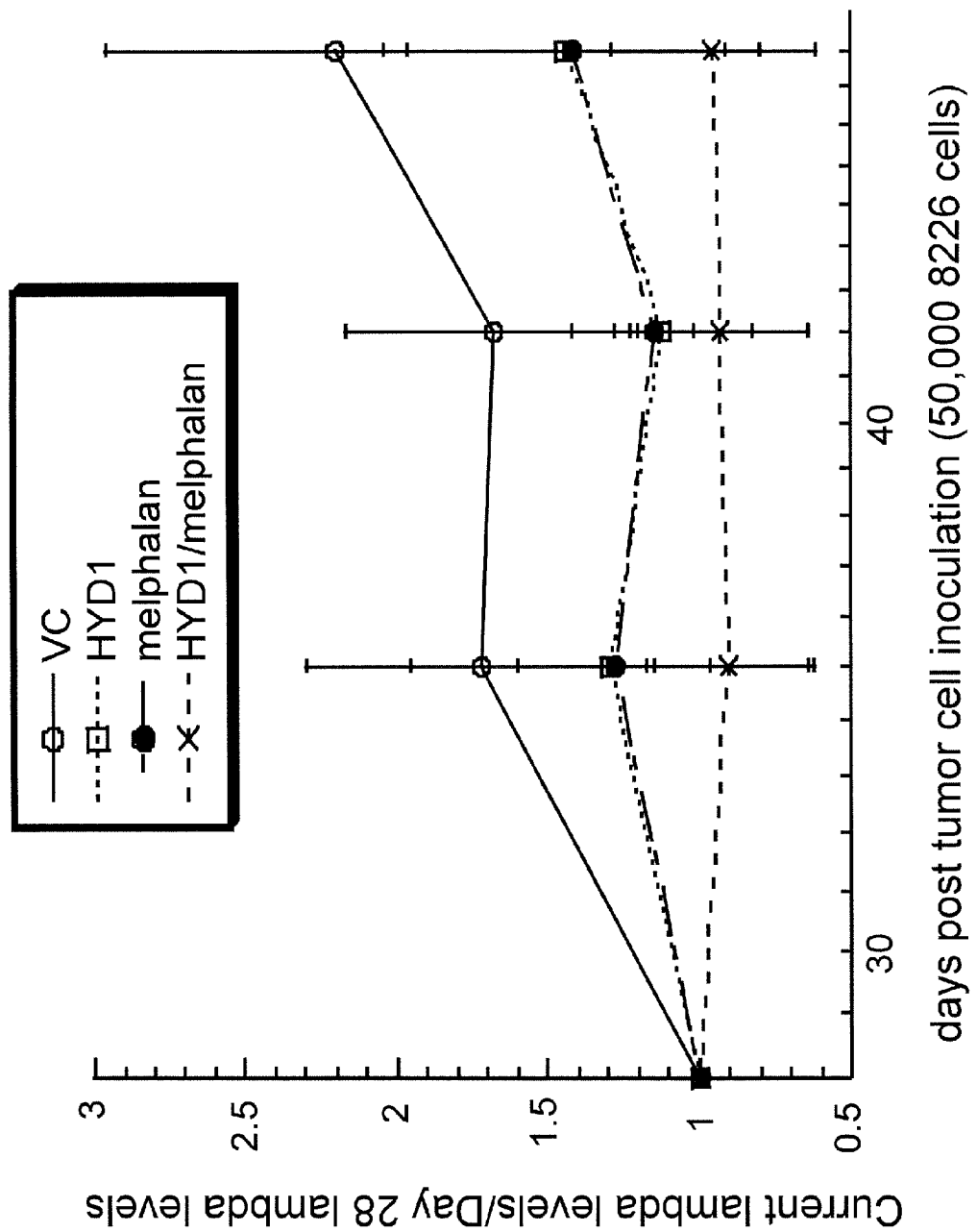
Figure 28A:
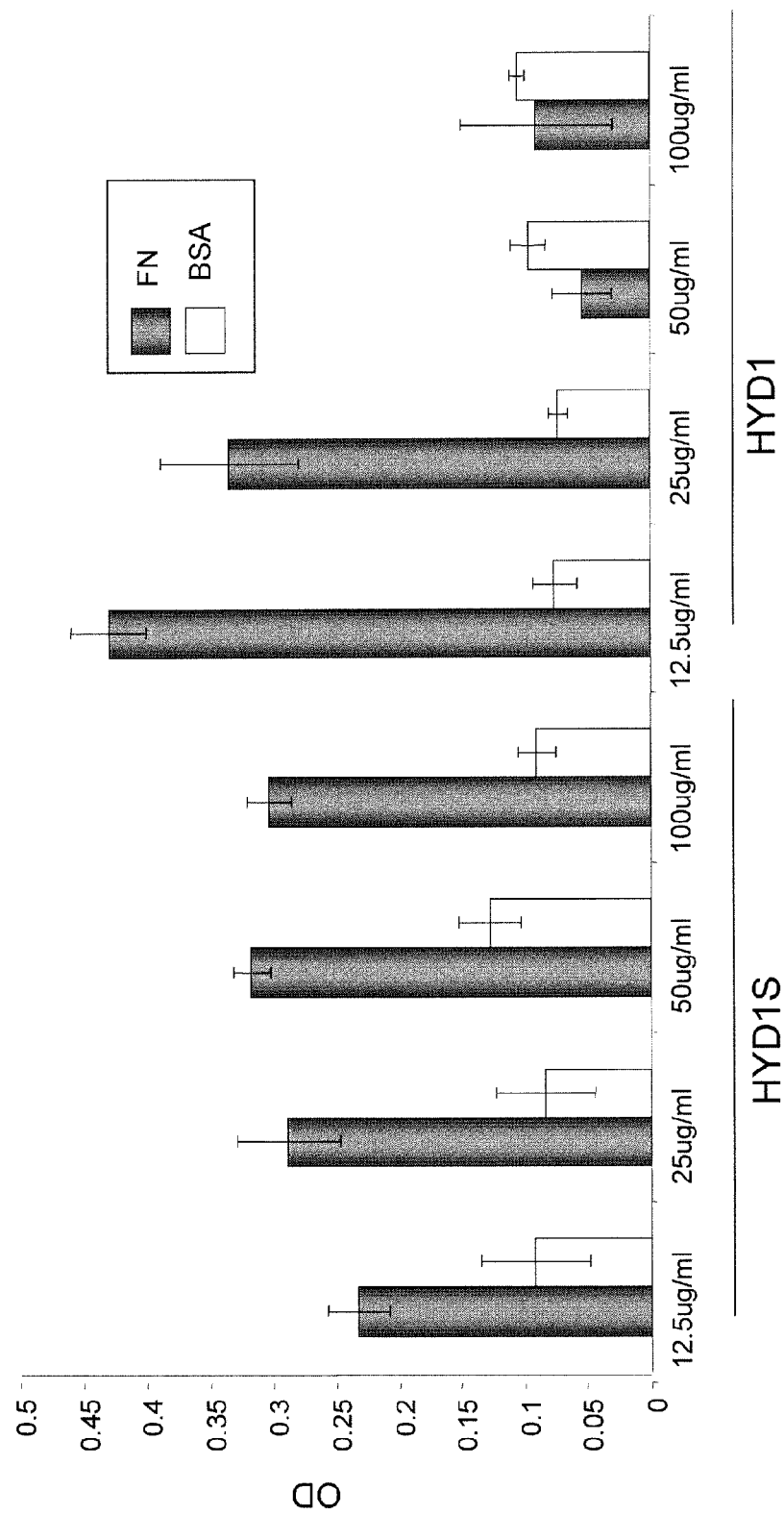
FIGS. 28A and 28B are graphs showing that HYD1 but not the scrambled peptide (HYD1S) inhibits cell adhesion of H929 myeloma cells (FIG. 28A) and 8226 cells (FIG. 28B) to FN.
Figure 28B:
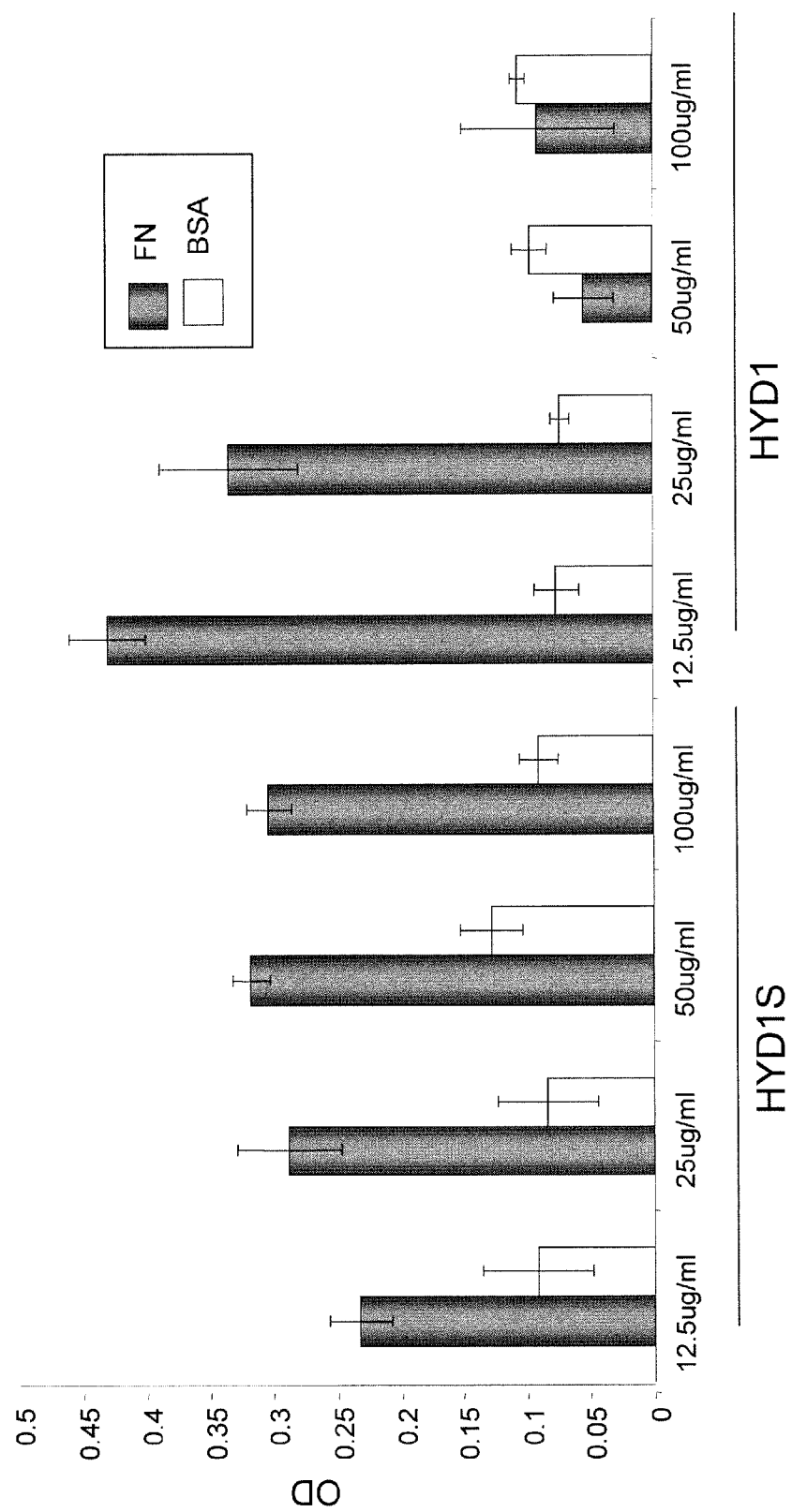
Figure 29A:
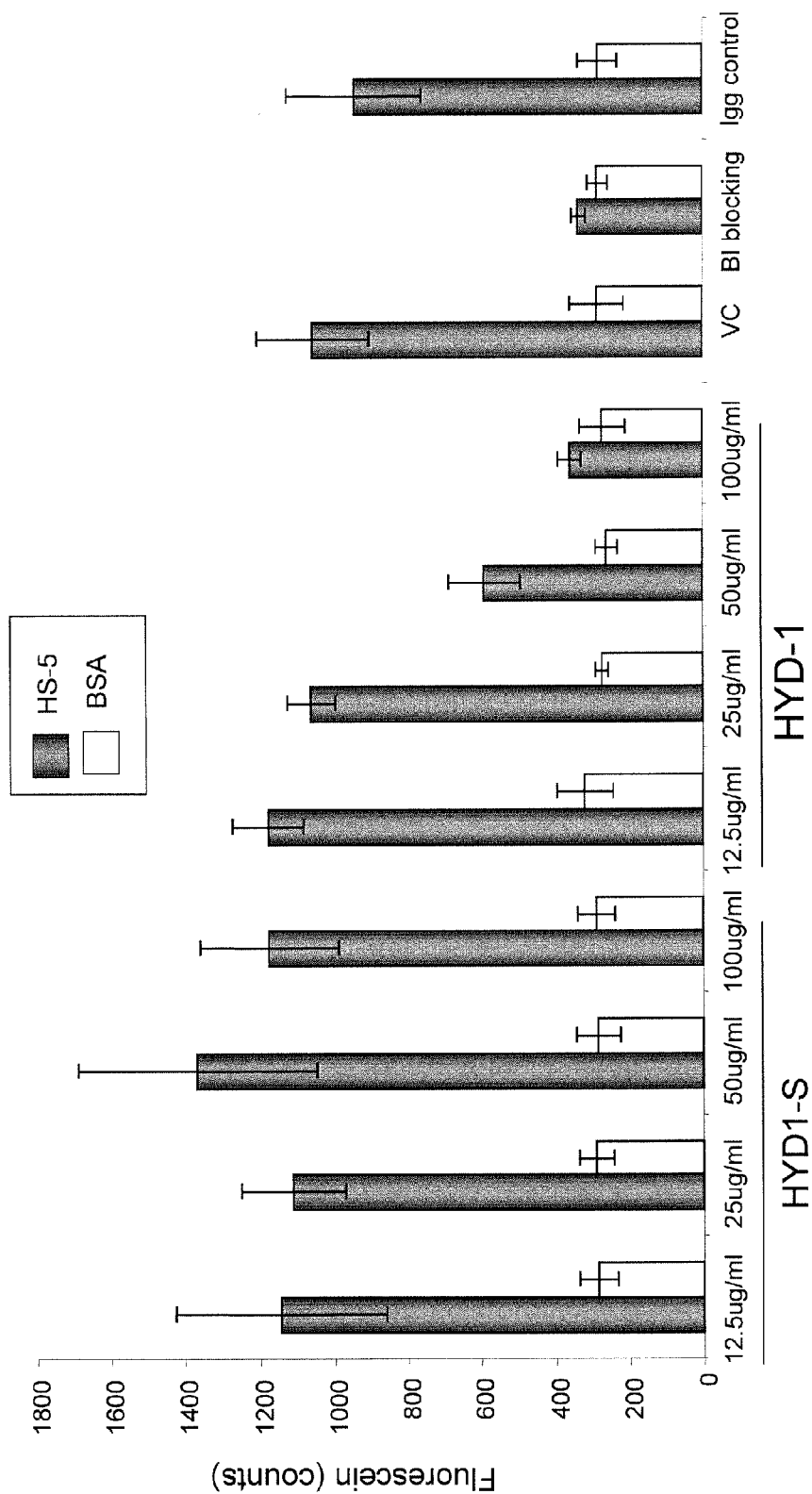
FIGS. 29A and 29B are graphs showing that HYD1 blocks adhesion of 8226 cells to the BMS HS-5 cell line (FIG. 29A) and does not inhibit adhesion of H929 cells to the BMS HS-5 cell line (FIG. 29B).
Figure 29B:
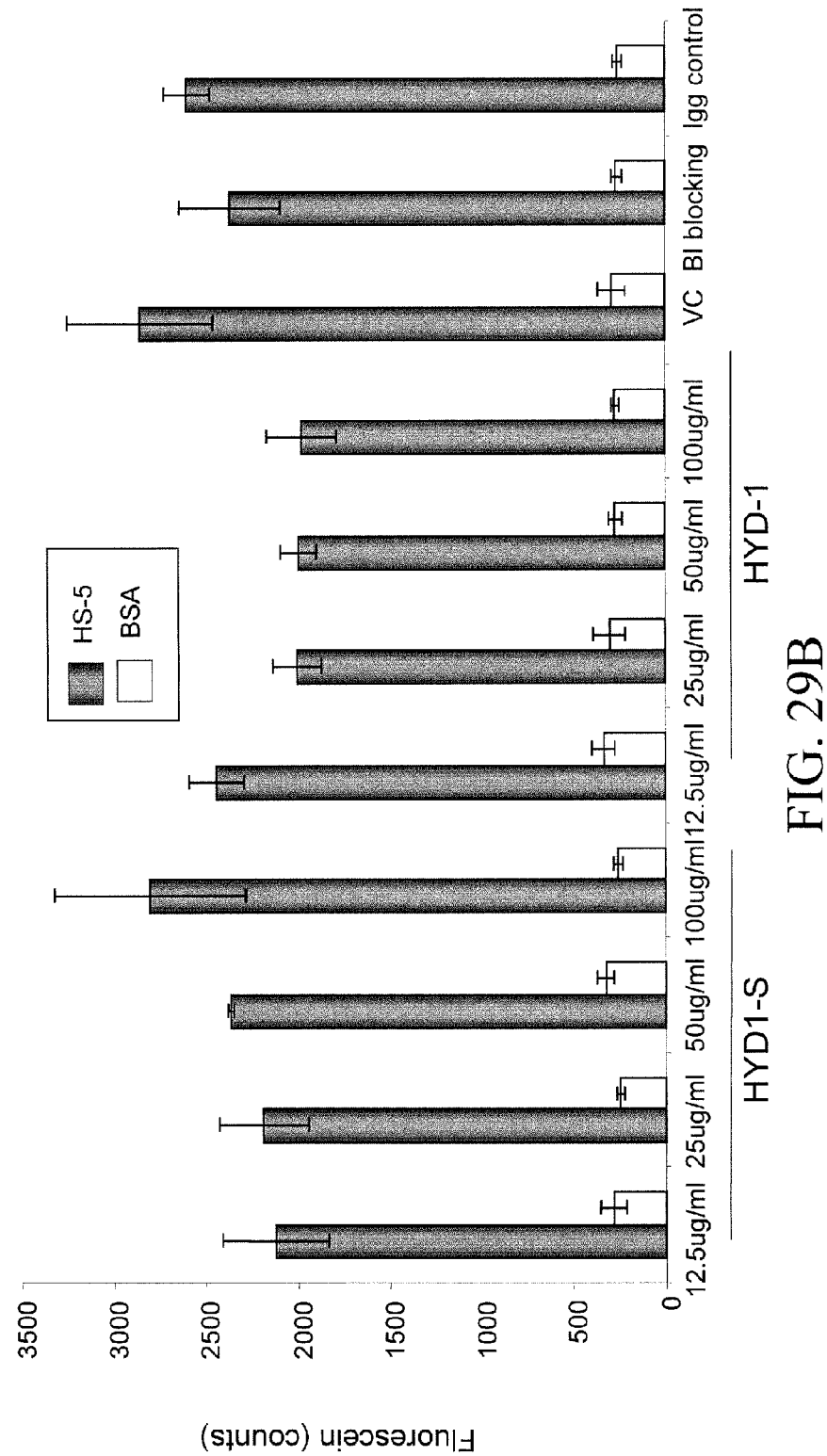
Figure 32:
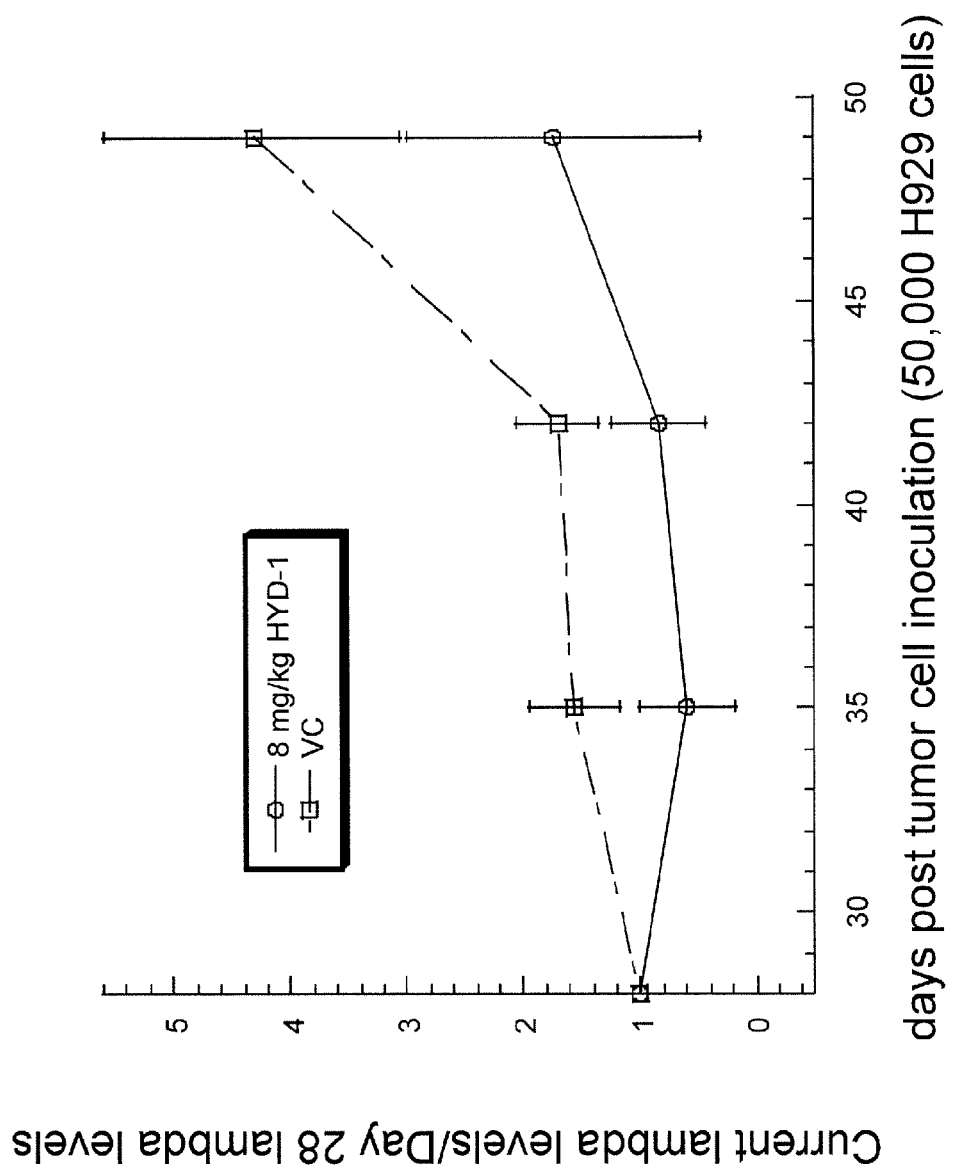
FIG. 32 is a graph showing that HYD1 treatment reduces H929 MM growth in vivo compared to vehicle control treatment. Tumor burden was measured by circulating lambda levels. On day 28 (before drug treatment), measurements were recorded for each individual mouse and subsequent values obtained weekly are represented as a ratio of day 28 (day X/day 28). N=4 mice per group. HYD1 was administered I.P. at 8 mg/kg daily for 14 days (starting day 28).
Figure 33:
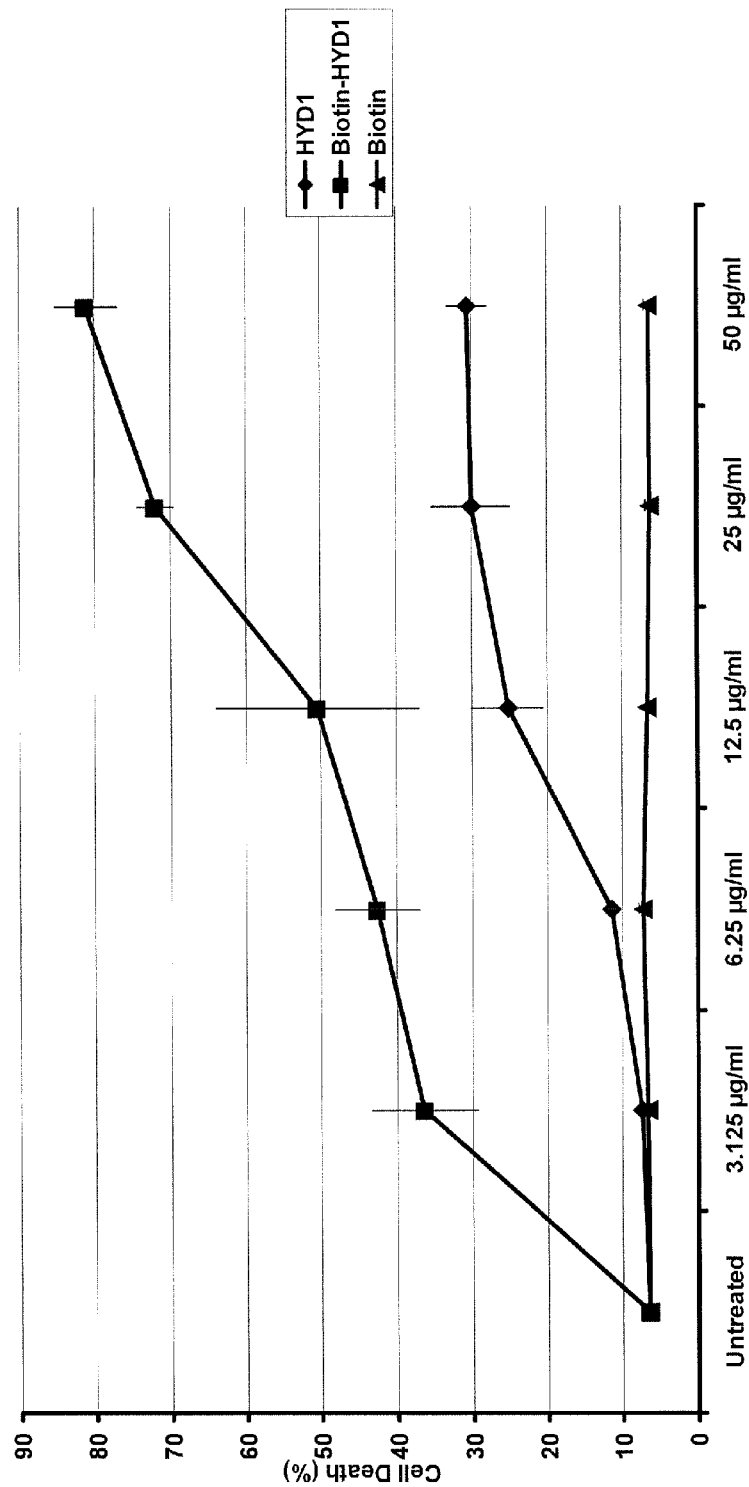
FIG. 33 is a graph showing that an HYD1 derivative (biotin-HYD1) has increased potency, compared to HYD1, in inducing H929 cell death. To produce biotin-HYD1, biotin was conjugated to the primary amine of the N-terminus of HYD1.
Figure 34:
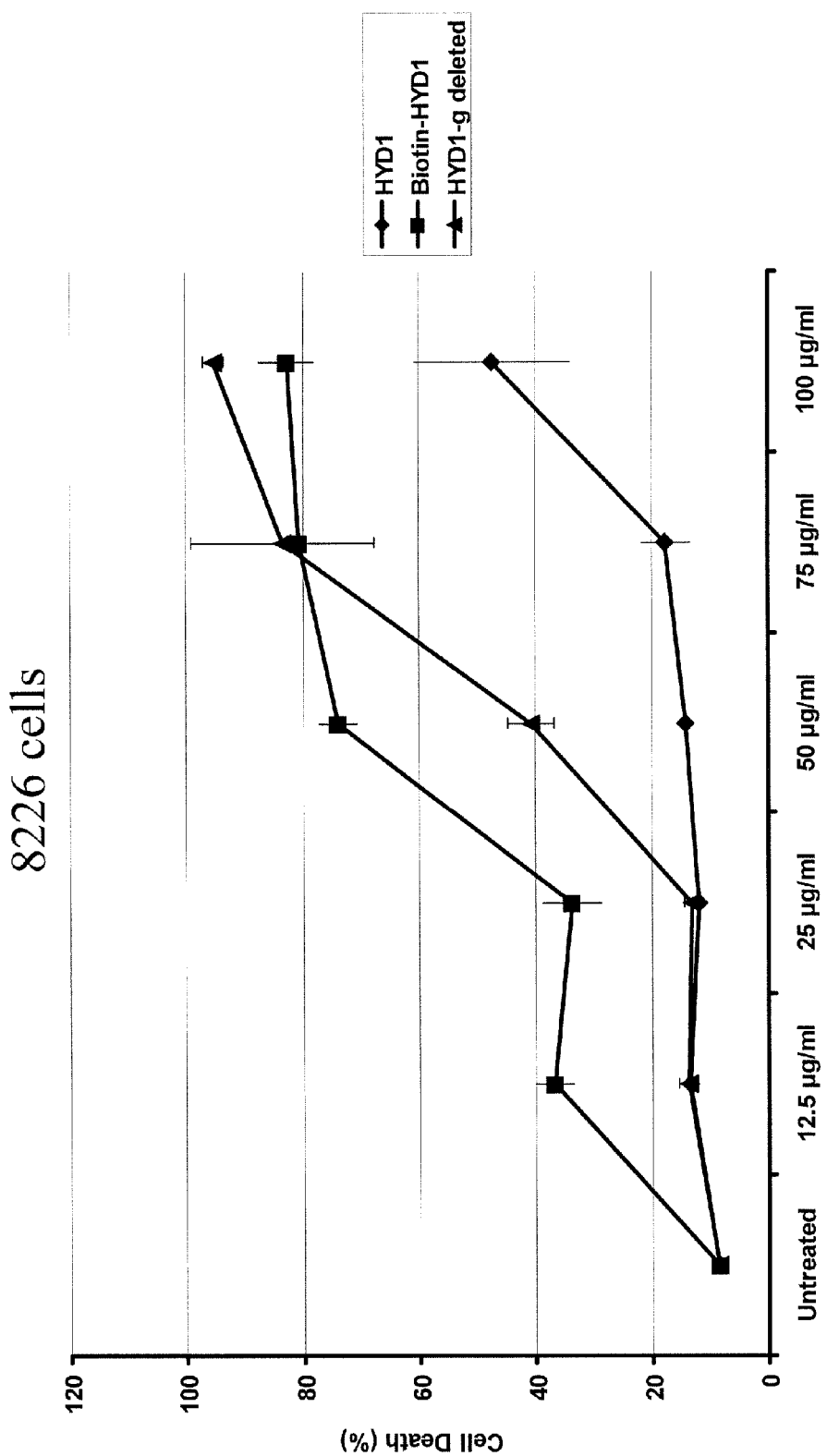
FIG. 34 is a graph showing that biotin-HYD1 and the HYD1 fragment HYD1-g each have increased potency, compared to HYD1, in inducing 8226 cell death. To produce HYD1-g, the C-terminus glycine was deleted to yield kikmviswk (SEQ ID NO:37).

The SCID-Hu model was used to determine whether HYD1 demonstrates anti-tumor activity in vivo. The SCID-Hu model consists of implanting human fetal bone into the mammary mouse fat pad of SCID mice. The myeloma cells are subsequently injected directly into the bone and myeloma cells will engraft only in the area of the human bone. Thus, the SCID-Hu model allows for the growth of the human myeloma cells in the human bone microenvironment (Yaccoby S et al. *Blood*, 1998; 92:2908-2913). Human paraprotein can be measured in the mouse sera and levels represent a good marker for evaluating tumor burden and response to chemotherapy. In summary, the SCID-Hu model is an excellent model for evaluating drug response of myeloma tumor burden in the bone marrow microenvironment without concerns of systemic disease confounding the interpretations of tumor response data. Circulating lambda levels were measured on day 28 (baseline reading), and 35, 42 and 49 by ELISA and for each mouse tumor burden was determined by calculating the lambda levels on day X divided by the baseline lambda levels recoded on day 28 for each mouse. Shown in FIG. 32 is the antitumor response of H929 engrafted tumor, when mice where given 8 mg/kg intraperitoneal (i.p.) injections daily for 14 days starting on day 28. Shown in FIGS. 26 and 27 are the results of a combination study, where appropriate mice were treated with 2 mg/kg HYD1 for 14 days with and without melphalan treatment. Again, antitumor activity was detected with HYD1 only group and the combination of HYD1 and melphalan showed the greatest reduction in tumor burden compared to either control or melphalan only treated mice.

Example 17

Apoptotic Activity of HYD1 Variants and Fragments

HYD1, biotinHYD1, FAMHYD, ikmviswkg (SEQ ID NO:22; HYD18), and kikmviswk (SEQ ID NO:37; HYD17) were synthesized by Global Peptides. The proteomics core at University of South Florida synthesized all other truncated and alanine substituted peptides. All peptides were HPLC purified and were established as being greater then 90% pure. In all cases Mass Spectrometry verified the peptide sequence.

Myeloma cells were plated at a density of 400,000 cells per ml in a 24 well plate. Cells were treated with the indicated dose of the peptide for 24 hours. Following 24 hrs of peptide exposure, apoptotic cells were detected using Annexin V staining and FACS analysis. Ten thousand events were analyzed by flow cytometry (Becton Dickinson, San Jose, Calif.). Experiments were performed in triplicate and repeated twice. Shown is a representative figure.

Figure 35:
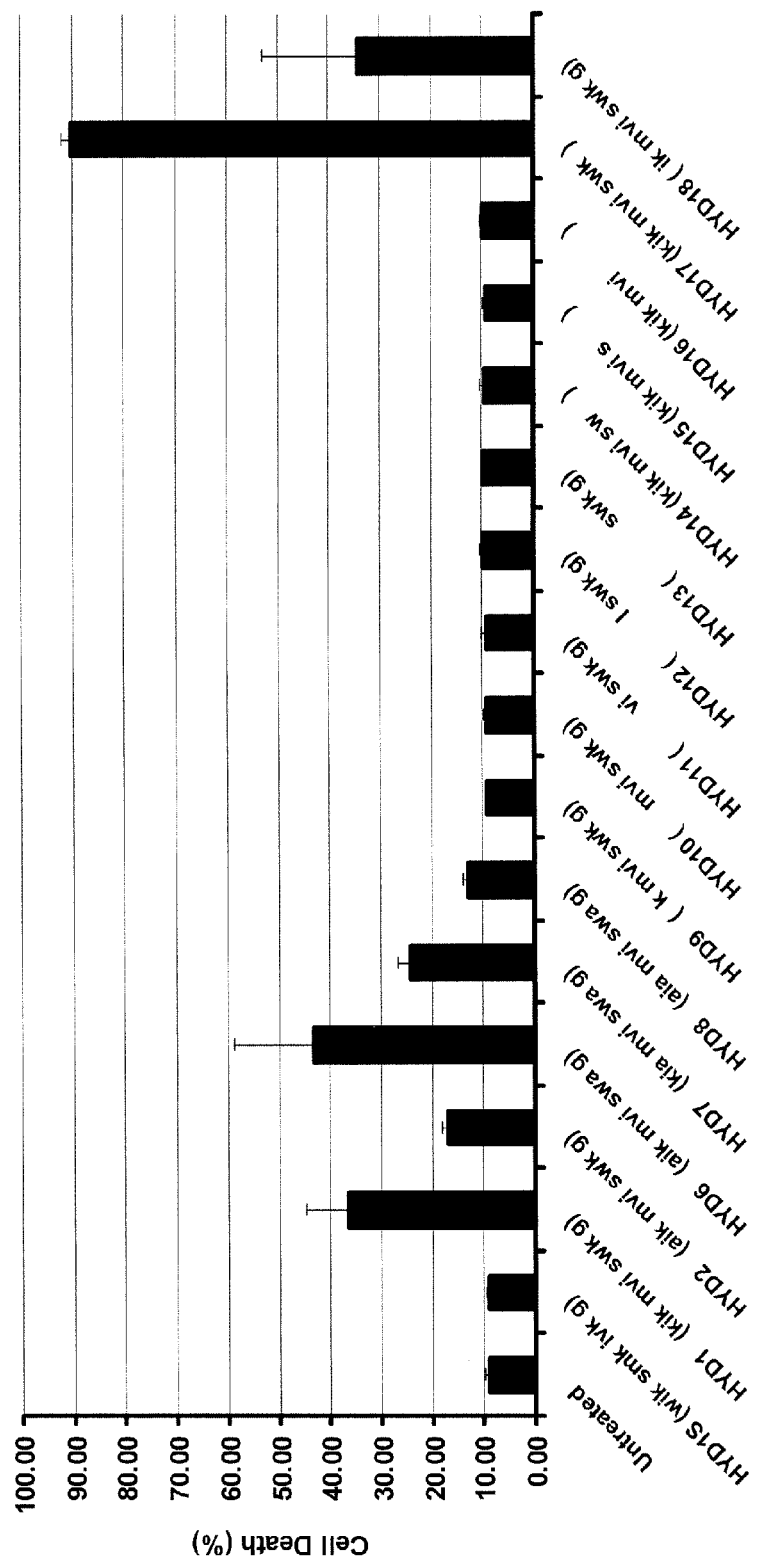
FIG. 35 is a graph showing the effect of HYD1 fragments and variants on apoptosis in 8226 cells. 8226 cells were incubated with the indicated D-amino acid peptides (100 ug/ml) for 24 hrs. Following peptide treatment, annexin V staining was used to detect apoptotic cells by FACS analysis.
Figure 36:
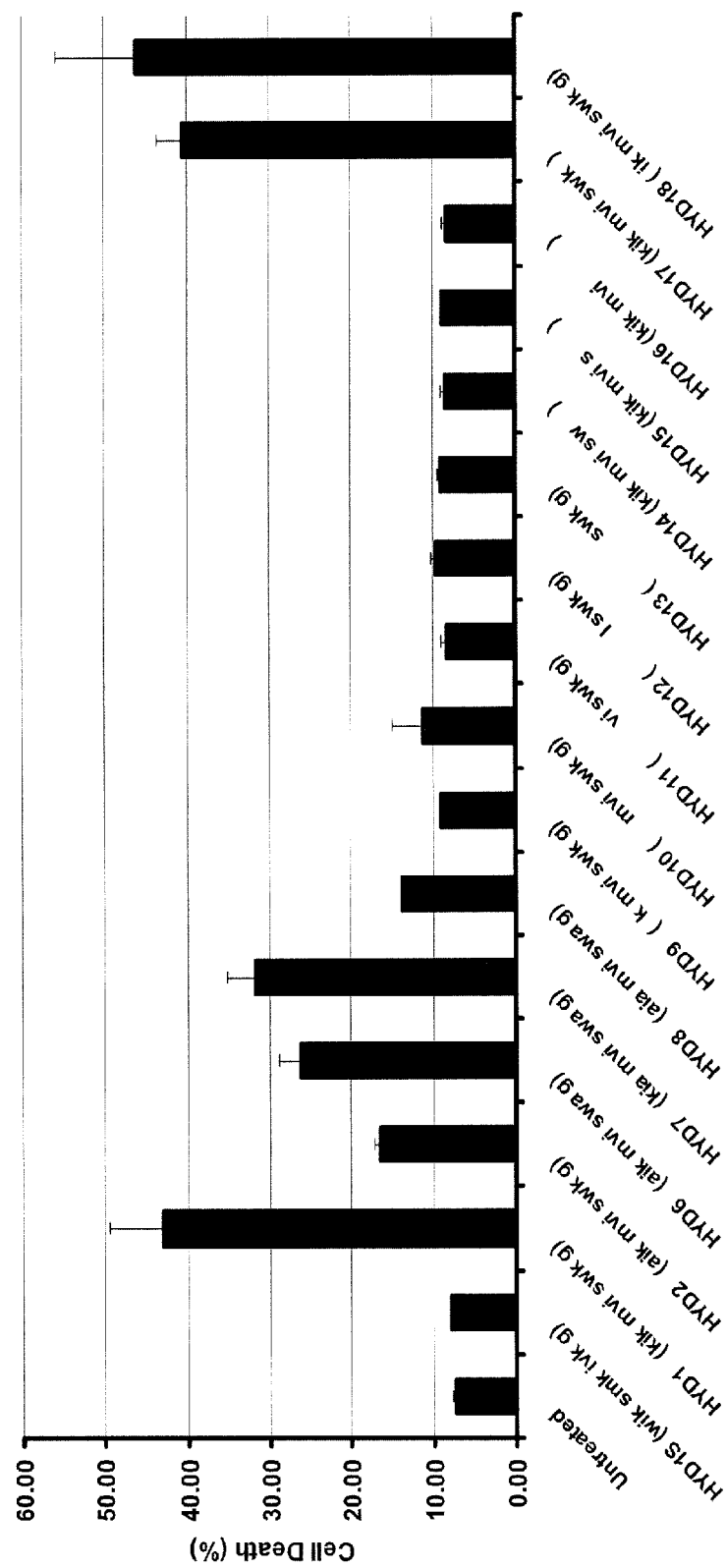
Figure 37:
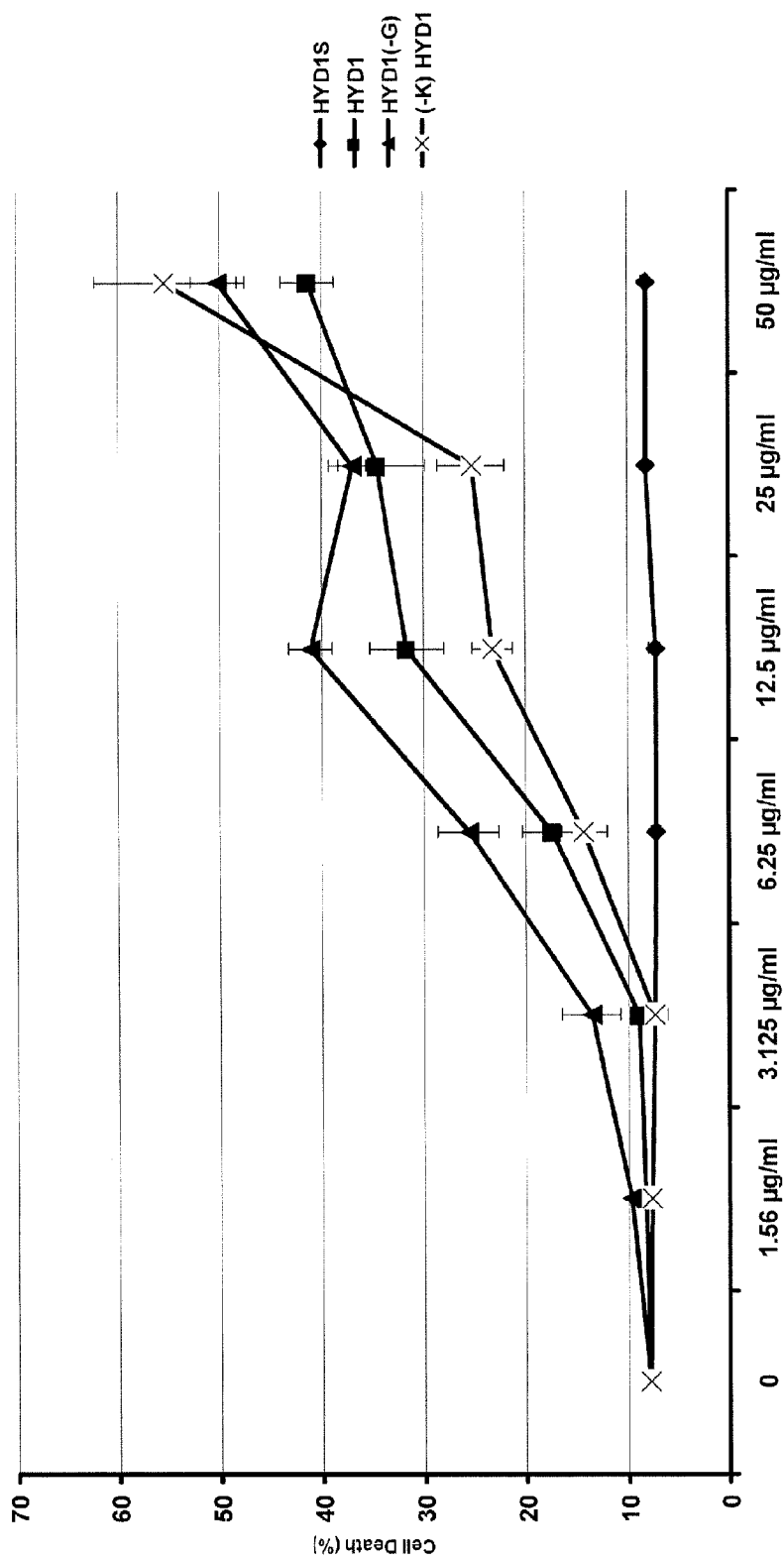
FIG. 37 is a graph showing dose response comparing HYD1, kikmviswk (SEQ ID NO:37; HYD1 g deleted) and ikmviswkg (SEQ ID NO:22; HYD1 k deleted) induced cell death in H929 cells.

HYD1 variants were designed to be progressively truncated at either the N or C terminus. In addition, the inventors sought to define whether lysine residues, which are protonated at physiological pH, were critical for biological activity. Thus, full-length HYD1 variants were also constructed in which the lysine residue was substituted with alanine. As shown in FIG. 35, deleting the C-terminus glycine residue increased the potency of HYD1. However, deleting the C terminus lysine and glycine amino acid completely abolished biological activity. Moreover, substituting all three lysine within HYD1 abolished biological activity. Finally, removing the lysine and the isoleucine residues from the N-terminus abolished activity. As shown in FIG. 36, and consistent with previous results, H929 cells are more sensitive to HYD1 treatment compared to 8226 cells. The structure-activity relationship was similar in H929 cells with the exception that deleting the terminal glycine did not substantially increase potency (see FIGS. 36 and 37) compared to HYD1 treatment.

Figure 38:
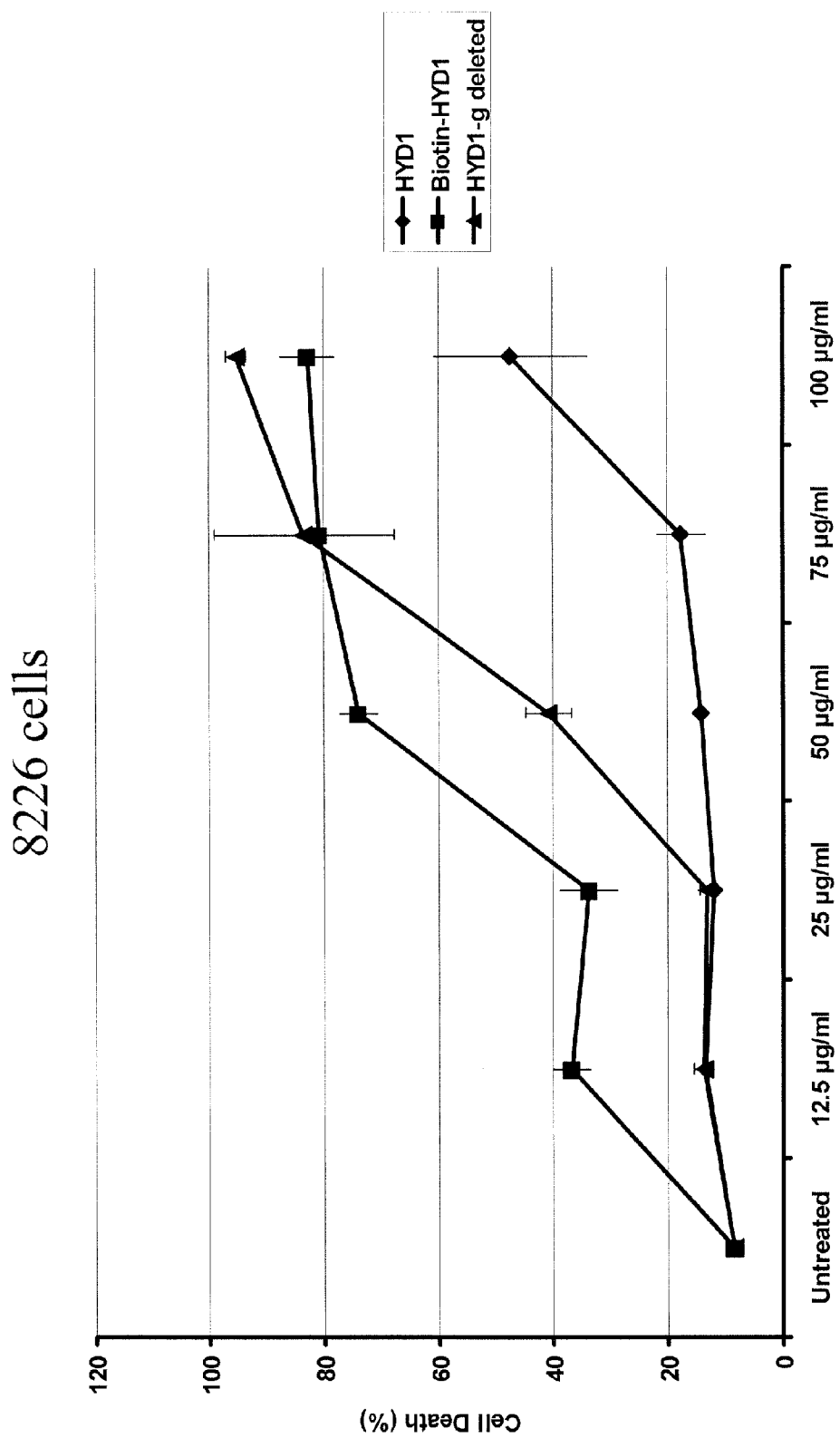
Figure 39:
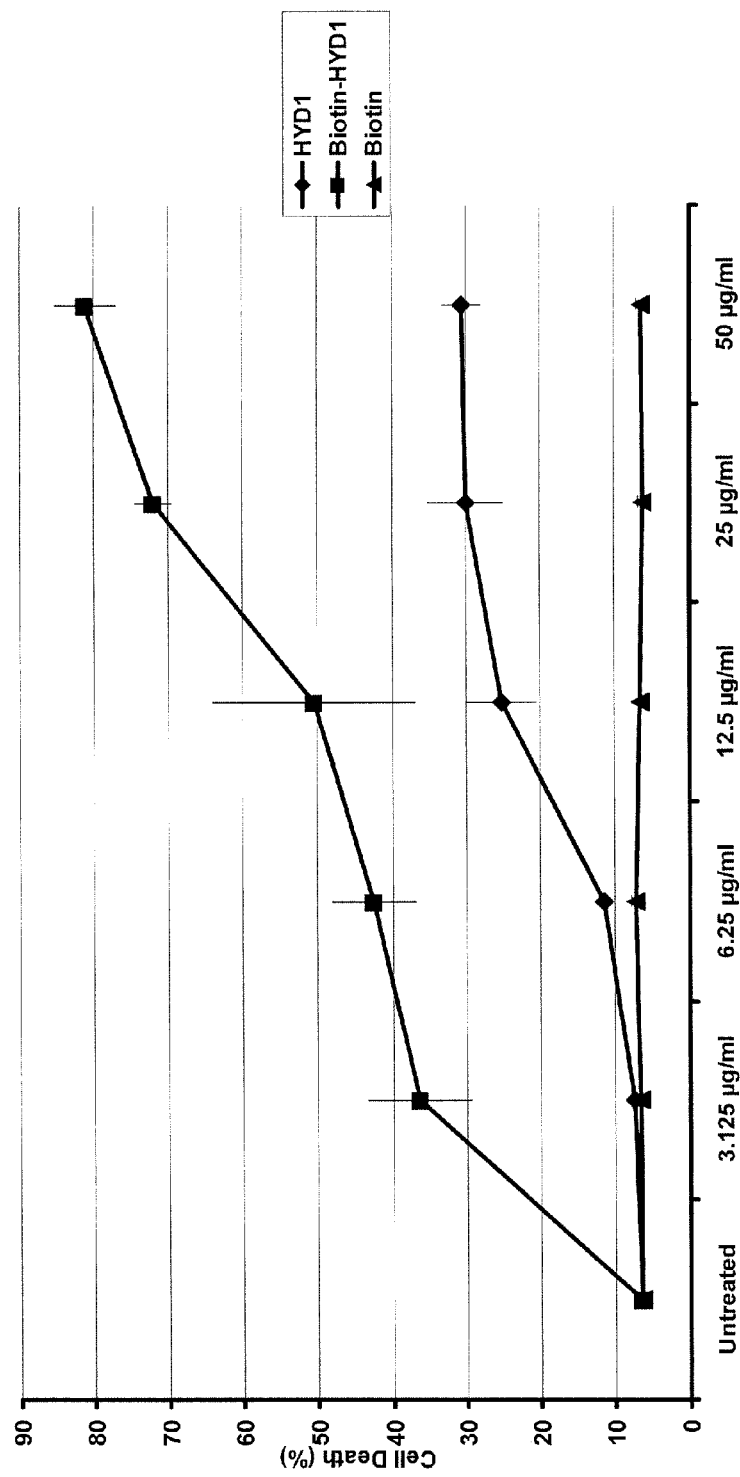
FIG. 39 is a graph showing that biotin-HYD1 demonstrates increased potency, compared to HYD1 treatment, in 8226 cells. Similarly, HYD1 C-terminus deleted glycine (kikmviswk; SEQ ID NO:37) demonstrates greater potency compared to HYD1 (kikmviswkg; SEQ ID NO:1) in 8226 cells.
Figure 40:
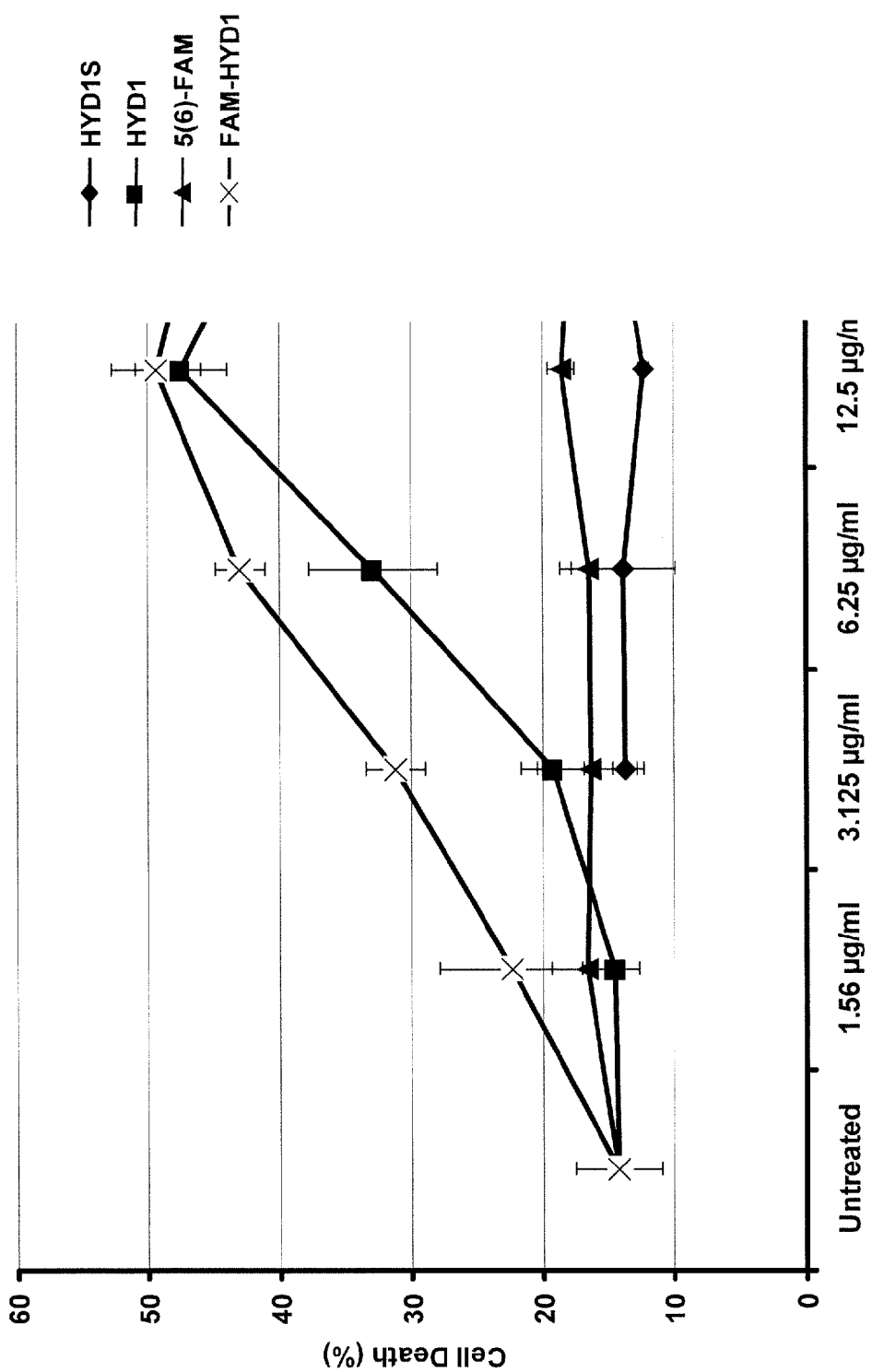
FIG. 40 is a graph showing that biotin-HYD1 demonstrates increased potency compared to HYD1 treatment in H929 cells.
Figure 41B:
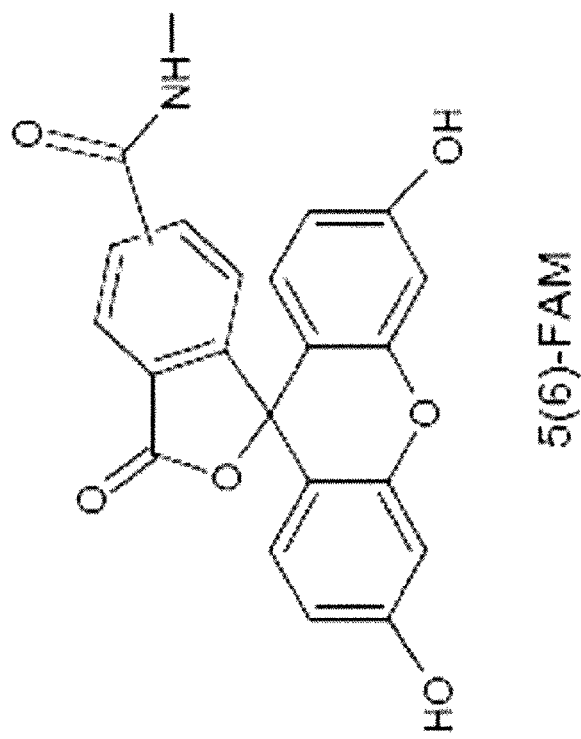
FIG. 41B shows the chemical structure of 5(6)-FAM.
Figure 41A:
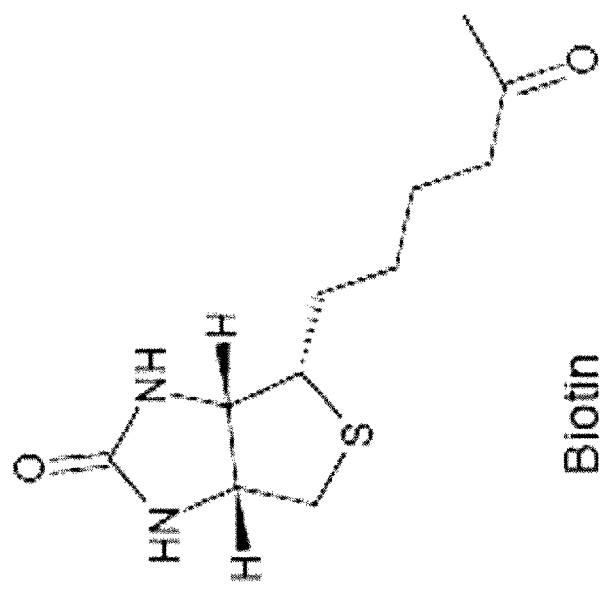
FIG. 41A shows the chemical structure of biotin.
Figure 41C:
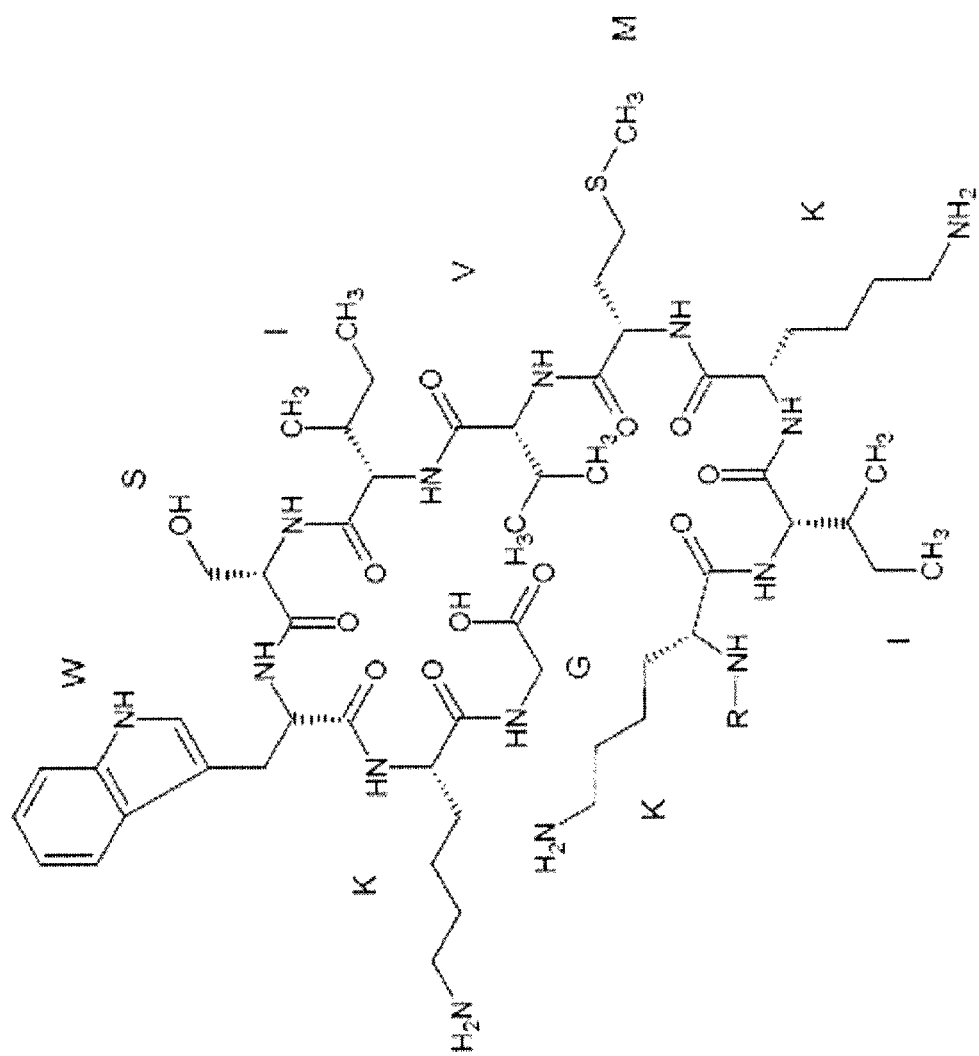
FIG. 41C shows the chemical structure of both biotin-HYD1 and FAM-HYD1, wherein R=biotin (FIG. 41A), or R=5(6)-FAM (FIG. 41B), respectively.

Shown in FIG. 41A is a biotin derivative of HYD1 (biotin-HYD1), which has increased potency compared to HYD1 in both 8226 and H929 cells (see FIGS. 38 and 39). Moreover, FAM-conjugated HYD1 retains biological activity. These data indicate that conjugation of the N terminus lysine residue can be accomplished without ablating biological activity and can be used to design compounds with greater activity and/or more favorable pharmacokinetics.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of treating a proliferation disorder in a subject, comprising administering an effective amount of at least one isolated peptide, or a polynucleotide encoding the at least one peptide, to the subject, wherein the at least one peptide is KIKMVISWKG (HYD1; SEQ ID NO:1) AIAMVISWAG (SEQ ID NO:2; HYD8); AIKMVISWAG (SEQ ID NO:3; HYD6); AIKMVISWKG (SEQ ID NO:4; HYD2); AKMVISW (SEQ ID NO:5); AKMVISWKG (SEQ ID NO:6); IAMVISW (SEQ ID NO:7); IAMVISWKG (SEQ ID NO:8); IKAVISW (SEQ ID NO:9); IKAVISWKG (SEQ ID NO:10); IKMAISW (SEQ ID NO:11); IKMAISWKG (SEQ ID NO:12); IKMVASW (SEQ ID NO:13); IKMVASWKG (SEQ ID NO:14); IKMVIAW (SEQ ID NO:15); IKMVIAWKG (SEQ ID NO:16); IKMVISA (SEQ ED NO:17); IKMVISAKG (SEQ ID NO:18); IKMVISW (SEQ ID NO:19); IKMVISWAG (SEQ ID NO:20); KMVISWKA (SEQ ID NO:21); IKMVISWKG (SEQ ID NO:22; HYD18; (-K)HYD1); ISWKG (SEQ ID NO:23); KAKMVISWKG (SEQ ID NO:24); KIAMVISWAG (SEQ ID NO:25; HYD7); KIAMVISWKG (SEQ ID NO:26); KIKAVISWKG (SEQ ID NO:27); KIKMAISWKG (SEQ ID NO:28); KIKMV (SEQ ID NO:29); KIKMVASWKG (SEQ ID NO:30); KIKMVI (SEQ ID NO:31; HYD16); KIKMVIAWKG (SEQ ID NO:32); KIKMVIS (SEQ ID NO:33; HYD15): KIKMVISAKG (SEQ ID NO:34); KIKMVISW (SEQ ID NO:35; HYD14); KIKMVISWAG (SEQ ID NO:36); KIKMVISWK (SEQ ID NO:37; HYD17; HYD1(-G)); KIKMVISWKA (SEQ ID NO:38); KMVISWKG (SEQ ID NO:39; HYD9); LSWKG (SEQ ID NO:40; HYD12); MVISWKG (SEQ ID NO:41; HYD10); SWKG (SEQ ID NO:42: HYD13); VISWKG (SEQ ID NO:43; HYD11); WIKSMKIVKG (SEQ ID NO:44); KMVIXW (SEQ ID NO:46); IKMVISWXX (SEQ ID NO:48); or KMVISWXX (SEQ ID NO:49); wherein X is any amino acid.

2. The method of claim 1, wherein the at least one peptide is modified by the addition of biotin, cystein, or carboxyfluorescein (FAM) to the C-terminus or N-terminus of the peptide.

3. The method of claim 1, wherein the at least one peptide comprises at least one D-ammo acid.

4. The method of claim 1, wherein the proliferation disorder is cancer.

5. The method of claim 1, wherein the at least one peptide is administered locally at the site of the proliferation disorder.

6. The method of claim 1, wherein the proliferation disorder is cancer, and wherein the at least one peptide induces cell death in circulating tumor cells.

7. The method of claim 1, wherein the proliferation disorder is cancer, and wherein the at least one peptide prevents or delays onset of metastasis to bone.

8. The method of claim 1, wherein the subject is not suffering from the proliferation disorder, and wherein the at least one peptide is administered to delay onset of the proliferation disorder.

9. The method of claim 1, wherein the subject is human.

10. The method of claim 1, wherein the proliferation disorder is a drug resistant cancer.

11. The method of claim 1, further comprising administering at least one anti-cancer agent to the subject before, during, or after said administering of the at least one peptide.

12. The method of claim 1, wherein the proliferation disorder is a cancer characterized by $\beta 1$ integrin signaling or $\beta 1$ integrin mediated adhesion.

13. The method of claim 1, wherein the proliferation disorder is characterized by a proliferation of T cells.

14. The method of claim 1, wherein the subject is also treated with chemotherapy or radiation therapy.

15. The method of claim 1, wherein the at least one peptide is provided in a composition comprising at least one pharmaceutically acceptable carrier.

16. The method of claim 1, wherein the at least one peptide is provided as a pharmaceutically acceptable salt.

* * * * *

UNITED STATES PATENT AND TRADEMARK OFFICE
CERTIFICATE OF CORRECTION

PATENT NO.        : 7,632,814 B2                                     Page 1 of 1
APPLICATION NO.   : 11/852177
DATED             : December 15, 2009
INVENTOR(S)       : Lori Anne Hazlehurst et al.

It is certified that error appears in the above-identified patent and that said Letters Patent is hereby corrected as shown below:

Title page,
Section (73) Assignees,

"University of South Florida, Tampa, FL (US); H. Lee Moffitt Cancer Center & Research Institute, Tampa, FL (US); The Arizona Board of Regents, Tucson, AZ (US); The Regents of the University of California, Oakland, CA (US)"

should read

--University of South Florida, Tampa, FL (US); H. Lee Moffitt Cancer Center & Research Institute, Tampa, FL (US); The Arizona Board of Regents on Behalf of the University of Arizona, Tucson, AZ (US); The Regents of the University of California, Oakland, CA (US)--.

Column 10,
Line 38, "100 g/ml" should read --100 µg/ml--.

Column 54,
Line 19, "200,000H929" should read --200,000 H929--.
Lines 51-52, "200,000H929" should read --200,000 H929--.

Column 55,
Line 37, "300xG" should read --3000xG--.

Column 58,
Line 26, "S-5 culture dish" should read --HS-5 culture dish--.

Column 62,
Line 47, "organdies such as" should read --organelles such as--.

Column 81,
Line 43, "SEQ ED NO: 17" should read --SEQ ID NO: 17--.

Signed and Sealed this

Thirtieth Day of March, 2010

David J. Kappos
*Director of the United States Patent and Trademark Office*